(12) United States Patent
Jha et al.

(10) Patent No.: US 11,739,318 B1
(45) Date of Patent: Aug. 29, 2023

(54) MODIFIED BIOSENSORS AND BIOCATALYSTS AND METHODS OF USE

(71) Applicant: Triad National Security, LLC, Los Alamos, NM (US)

(72) Inventors: Ramesh K. Jha, Los Alamos, NM (US); Charlie E. Strauss, Los Alamos, NM (US); Taraka Dale, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 987 days.

(21) Appl. No.: 16/226,474

(22) Filed: Dec. 19, 2018

Related U.S. Application Data

(60) Provisional application No. 62/607,697, filed on Dec. 19, 2017.

(51) Int. Cl.
  *C12N 15/10* (2006.01)
  *C12N 9/88* (2006.01)
  (Continued)

(52) U.S. Cl.
  CPC .......... *C12N 15/1086* (2013.01); *C12N 9/88* (2013.01); *C12N 15/52* (2013.01); *C12N 15/74* (2013.01); *G01N 33/573* (2013.01); *G01N 33/581* (2013.01); *C12Y 401/0304* (2013.01); *G01N 2333/952* (2013.01); *G01N 2333/988* (2013.01)

(58) Field of Classification Search
  CPC ...... C12N 9/88; C12N 15/1086; C12N 15/52; C12N 15/74; C12Y 401/0304; G01N 33/573; G01N 33/581; G01N 2333/952; G01N 2333/988
  See application file for complete search history.

(56) References Cited

U.S. PATENT DOCUMENTS

| | | | |
|---|---|---|---|
| 6,562,958 B1 * | 5/2003 | Breton | C07K 14/22 536/23.7 |
| 8,735,124 B2 * | 5/2014 | Tawfik | C12N 9/18 435/196 |

(Continued)

OTHER PUBLICATIONS

Parkhill et al. (Nature, 2001,413:848-852) (Year: 2001).*

(Continued)

*Primary Examiner* — Jeremy C Flinders
(74) *Attorney, Agent, or Firm* — Klarquist Sparkman, LLP

(57) ABSTRACT

Biosensors including a nucleic acid encoding a PcaU protein, a PobR protein, a CatM protein, a PcaR protein, or a TphR protein are provided. In some examples, the biosensors include a promoter regulated by the sensed molecule operably linked to a reporter gene. The biosensors may be included in a vector or in cells including one or more of the biosensors or vectors. Modified chorismate pyruvate lyase (UbiC) and modified paraoxonase (PON1) proteins including one or more amino acid substitutions are provided. Finally, methods of selecting biocatalysts with increased activity including transforming a library of cells expressing a biosensor with one or more nucleic acids encoding one or more mutations in a gene involved in a biosynthesis pathway, determining activity of the reporter protein; and selecting a cell with increased reporter protein activity as expressing a biocatalyst with increased activity are provided.

11 Claims, 22 Drawing Sheets
Specification includes a Sequence Listing.

(51) Int. Cl.
*C12N 15/52* (2006.01)
*G01N 33/58* (2006.01)
*G01N 33/573* (2006.01)
*C12N 15/74* (2006.01)

(56) References Cited

U.S. PATENT DOCUMENTS

2012/0213834 A1    8/2012  Tawfik et al.
2012/0219971 A1*   8/2012  Dietrich .................. C12N 9/12
                                                    435/7.37

OTHER PUBLICATIONS

Zhang et al. (ACS Synth. Biol., 2012, 1:274-283) (Year: 2012).*
Amitai et al., "Enhanced stereoselective hydrolysis of toxic organophosphates by directly evolved variants of mammalian serum paraoxonase," *FEBS J.* vol. 273, pp. 1906-1919, 2006.
Aharoni et al., "Directed evolution of mammalian paraoxonases PON1 and PON3 for bacterial expression and catalytic specialization," *PNAS,* vol. 101, No. 2, pp. 482-487, 2004.
Jha et al., "Engineering an *Acinetobacter* regulon for biosensing and high-throughput enzyme screening in *E. coli* via flow cytometry," *Nucleic Acids Research,* vol. 42, No. 12, pp. 8150-8160, 2014.
Jha et al., "Rosetta comparative modeling for library design: Engineering alternative inducer specificity in a transcription factor," *Proteins,* vol. 83, No. 7, pp. 1327-1340, 2015.
Jha et al., "A microbial sensor for organophosphate hydrolysis exploiting an engineered specificity switch in a transcription factor," *Nucleic Acids Research,* doi: 10.1093/nar/gkw687, 2016 (11 pages).
Jha, et al., "Whole Cell Biosensing in *Pseudomonas putida* KT2440," *Agile BioFoundry Annual All Hands Meeting,* Aug. 28-29, 2017 (1 page).
Jha, "A High Throughput Platform for Enzyme Evolution," *TechConnect World Innovation,* Anaheim, California, May 14, 2018 (41 pages).
Jha, "Better Enzymes for a Sustainable World," *DisrupTECH,* Los Alamos National Laboratory, New Mexico, Jul. 12, 2018 (16 pages).
Jha, "Biosensors and Flow Cytometry," *Agile BioFoundry Annual All Hands Meeting,* Emeryville, CA, Sep. 10, 2018 (23 pages).
Jha, "Biosensor Mediated P. putida Strain Development for Biomanufacturing," *Agile BioFoundry Annual All Hands Meeting,* Emeryville, CA, Sep. 11, 2018 (27 pages).
McDonald, "The Perfect Fit," *National Security Science,* Los Alamos National Laboratory, vol. 1663, pp. 2-7, 2015.
Raman et al., "Evolution-guided optimization of biosynthetic pathways," *PNAS,* vol. 111, No. 50, pp. 17803-17808, 2014.
Rogers et al., "Biosensor-based engineering of biosynthetic pathways," *Current Opinion in Biotechnology,* vol. 42, pp. 84-91, 2016.

* cited by examiner

Positive feedback regulation

FIG. 3
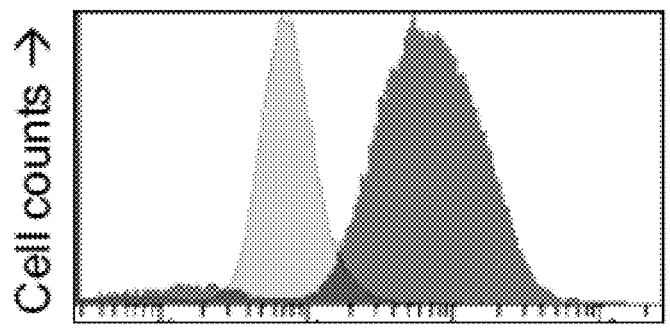
FIG. 4A  FIG. 4B
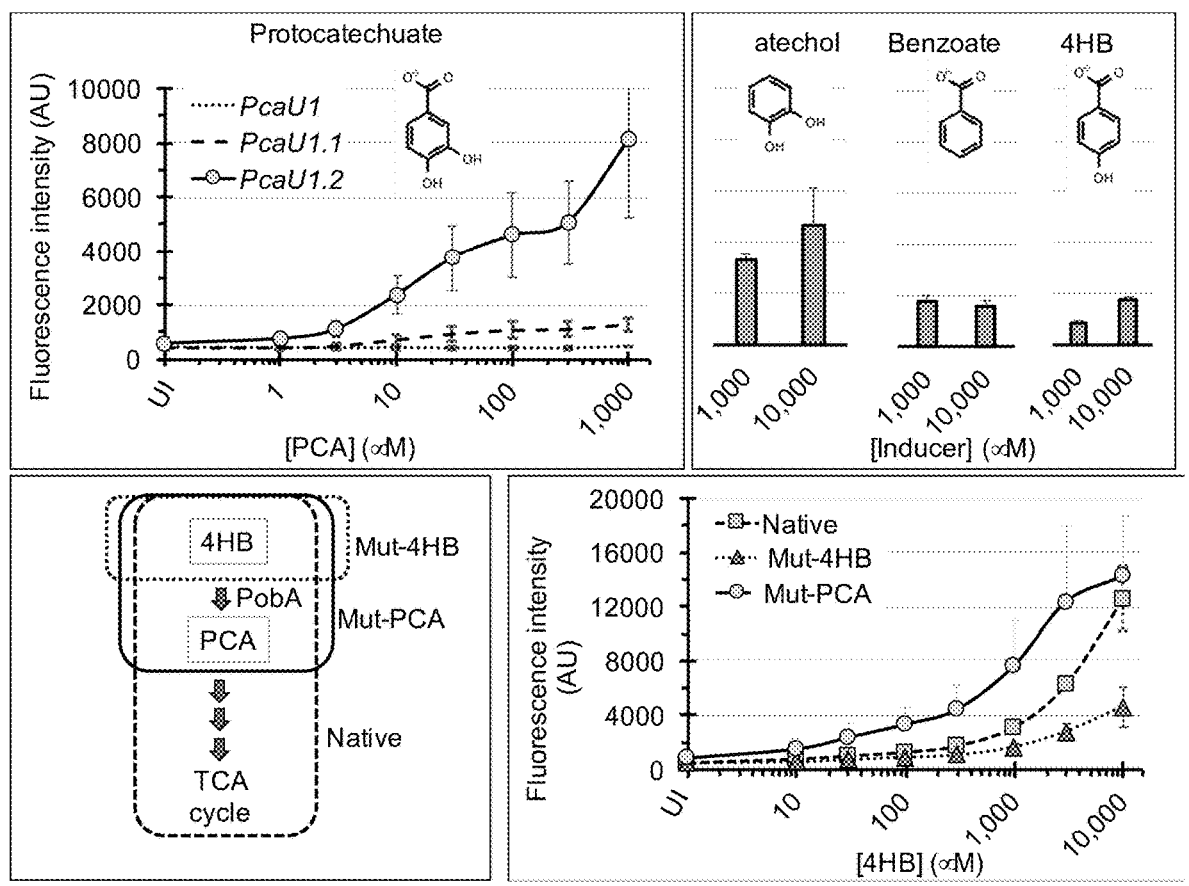
FIG. 4C  FIG. 4D

No supplement | 10 mM Benzoate | 10 mM Benzoate 100 µM 4HB

UbiC library screen

Round 1

Round 3

PobA-wt

US 11,739,318 B1

MODIFIED BIOSENSORS AND BIOCATALYSTS AND METHODS OF USE

CROSS REFERENCE TO RELATED APPLICATION

This claims the benefit of U.S. Provisional Application No. 62/607,697, filed Dec. 19, 2017, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration and awards from the U.S. Department of Energy BioEnergy Technologies Office (Agile BioFoundry). The government has certain rights in the invention.

FIELD

This disclosure relates to biosynthesis of compounds in prokaryotic organisms, in particular biosensors and biocatalysts for compounds of interest and methods of developing biosensors and biocatalysts for use in prokaryotic organisms.

BACKGROUND

Biomanufacturing is a sustainable route towards "drop in" and "replacement" chemicals which currently are produced from petroleum-based products. Biomanufacturing utilizes renewable feedstocks and microbial cell factories and/or enzymatic reactions to produce chemicals that are industrial precursors and building blocks of a variety of polymers. Among them, adipic acid (ADA) and terephthalic acid (TPA) are polymer precursors with high global demand that are currently made via chemical processes with adverse environmental impact. β-ketoadipic acid (BKA) is another "replacement" polymer precursor with a high global demand. The biotransformation routes for these chemicals can be achieved via one or more of 4-hydroxybenzoic acid (4HB), protocatechuic acid (PCA), catechol, and cis,cis-muconic acid (ccMA).

For example, PCA is an important central intermediate in aromatic catabolism and siderophore biosynthesis, as well as an important hub molecule in conversion of sugars to ccMA and other shikimate-derived products. These products are currently produced on an industrial scale via chemical processes, which are frequently environmentally harmful and expensive. Biomanufacturing could provide renewable production of commodity chemicals that reduces energy consumption and environmental impact.

SUMMARY

For the development of robust industrial strains, model organisms such as *E. coli* that already have well developed synthetic biology tools, including multiple biosensors for molecules of interest, may offer only limited advantages for a given target. Instead, the use of diverse range of organisms that exhibit beneficial phenotypes (e.g., high flux through target pathways, thermal or pH tolerance, etc.) often enables more efficient and cost effective process design. However, the deployment of biosensor-based screening in such organisms commonly does not necessarily directly transfer from model organisms (e.g., *E. coli*), and loss of sensitivity and dynamic range can occur. *Pseudomonas putida* KT2440 is one such strain that has increasingly been investigated as a potential microbial cell factory for producing target chemicals due to its high toxicity tolerance and high natural flux in aromatic-catabolic pathways.

Biosensors for polymer precursors via one or more of 4-hydroxybenzoic acid (4HB), protocatechuic acid (PCA), catechol, and cis,cis-muconic acid (ccMA) are disclosed herein. In addition, methods to improve biosynthetic routes utilizing a product- or an intermediate-specific biosensor and targeting key bottleneck enzymes for a gain-of function are disclosed. The present disclosure includes: (i) gene circuits that consist of DNA sequences, which code for proteins (e.g., biosensors) that can interact with metabolites and regulate the expression of a reporter (for example, gfp encoding green fluorescent protein); (ii) establishment of the sensor-reporter system in industrially relevant organisms, for example *Pseudomonas putida*; (iii) use of a sensor-reporter system to optimize a metabolic pathway by evolving key bottleneck enzymes; and (iv) introducing modified or improved enzymes into production strains for enhanced biomanufacturing. The sensor-reporter system for modification (e.g., "evolution") of an enzyme or a pathway or a strain addresses a "needle-in-a-haystack" problem, since a library of variants can be conveniently screened using methods such as flow cytometry or visualizing colonies (e.g., on a petri dish). Introduction of the sensor-reporter system in non-model organisms with beneficial phenotypes, enabling effective process design for bio-based products is described.

Disclosed herein are biosensors for PCA, 4HB, ccMA, BKA, and TPA. In some examples, the biosensors further include a promoter (e.g., a promoter regulated by the sensed molecule) operably linked to a reporter protein. In some examples, the biosensor includes a nucleic acid encoding a PcaU protein (such as a modified PcaU protein), a PobR protein (such as a PobR-DM protein), a CatM protein, a PcaR protein, or a TphR protein.

Also disclosed are vectors including the disclosed biosensors and cells (such as transformed cells) including one or more of the disclosed biosensors or vectors. In some embodiments, the vectors include SEQ ID NOs: 2, 3, 6, 7, 21, 22, 29, 30, and 31. In some examples, the cells are *Pseudomonas putida, Escherichia coli*, or *Acinetobacter baylyi* cells.

Disclosed herein is a modified biocatalyst for producing 4HB. The modified catalyst is a chorismate pyruvate lyase (UbiC) that includes one or more (such as 1, 2, 3, or more) amino acid substitutions at amino acid positions corresponding to amino acids 31, 34, 78, 80, 92, and 114 of SEQ ID NO: 18.

Finally, methods of selecting biocatalysts with increased activity or gain-of-function using the disclosed biosensors are provided. The methods include transforming a library of cells expressing a disclosed biosensor with one or more nucleic acids encoding one or more mutations in a gene involved in a biosynthesis pathway, determining the activity of the reporter protein; and selecting a microbial cell with increased reporter protein activity as expressing a biocatalyst with increased activity or gain-of-function. In some examples, the methods further include isolating a nucleic acid encoding the biocatalyst from the selected cell.

The foregoing and other features of the disclosure will become more apparent from the following detailed description, which proceeds with reference to the accompanying figures.

BRIEF DESCRIPTION OF THE DRAWINGS

In FIG. 1B, the biocatalyst is under a positive feedback regulation. Based on the biocatalyst activity, an intracellular substrate or exogenously provided substrate is converted to a product (molecule of interest or a suitable intermediate), which activates a transcription factor (TF) on the biosensor or biosensor/biocatalyst plasmid resulting in expression of the reporter gene (exemplified by gfp). This results in gain of fluorescence in the microbial cells. These exemplary schemes can be utilized to select for gene variants that encode for an improved activity in a biocatalyst (e.g., enzyme).

FIG. 2A shows alignment of the evolved PcaU promoter (pPcaU1.1; SEQ ID NO: 11) with *E. coli* functional promoter (pPcaU1; SEQ ID NO: 10). Positions randomized to create the library are shown below the alignment. The PcaU operator is only partially shown. FIG. 2B is a homology model of PcaU inducer binding domain as a dimer and docked with protocatechuate (spheres), showing spatial position of T147 and D148 (sticks), which were randomized.

FIG. 3 is a graph showing fluorescence signal measured using flow cytometry (ex/em 488/530) in *P. putida* KT2440 mutant strain with an evolved sensor plasmid pPcaU1.2. Cells grown in the absence of PCA (uninduced) are shown in light gray and cells grown in the presence of 1 mM PCA (induced) are shown in dark gray.

FIGS. 4A-4D are a series of panels showing whole cell biosensing of PCA in *P. putida*. FIG. 4A is a response plot of different generations of a PcaU-based sensor in *P. putida* strain when exogenously dosed with PCA. FIG. 4B is a set of plots showing specificity evaluation of the evolved sensor pPcaU1.2, against similar aromatic molecules. FIG. 4C is a diagram showing the ability of 4-hydroxybenzoate to be metabolized to PCA and beyond, depending on the genotype of *P. putida* strains. FIG. 4D is a graph showing intracellular production of PCA and sensor response in *P. putida* strains. Error bars are standard deviations from two or more experiments. Only positive or negative error bars shown in some cases for clarity.

FIG. 6A shows that the natural PobR activates a promoter for expression of PobA that converts 4HB to PCA (top panel). A synthetic construct was designed for 4HB sensing consisting of a double mutant of PobR (PobR-DM) that has a stronger activation of the promoter than the natural TF (depicted by a thick arrow), which results in a high expression of sfGFP (reporter) (middle panel). The Sensor+Enzyme is a synthetic construct for 4HB conversion and sensing consisting of the same PobR-DM sensor and promoter but resulting in an expression of sfGFP fused UbiC (reporter). Hence, the promoter is under positive feedback regulation of the UbiC activity, which catalyzes the conversion of chorismate into 4HB and pyruvate (bottom panel). FIG. 6B is the plasmid construct for Sensor. FIG. 6C is the plasmid construct for Sensor+Enzyme.

FIG. 7A is a graph showing a dose-response plot of *P. putida* KT2440 strains (wild-type KT2440 and CJ182) transformed with the PobR-DM sensor plasmid (pPobR). Error bars are standard deviations from duplicate experiments. FIG. 7B shows colonies of CJ182, with the plasmid pPobR (Sensor), or with the UbiC plasmid pPobR_ubiC-wt (Sensor+Enzyme), grown in the presence or absence of 100 µM 4HB and/or 10 mM benzoate inhibitor.

FIG. 8A shows the pathway from chorismate to 4HB and pyruvate. Chorismate pyruvate lyase (UbiC from *E. coli* (ecUbiC)) can convert chorismate (an intermediate in the shikimate pathway) to 4-hydroxybenzoate (4HB) and pyruvate. 4HB is a value-added chemical that can be converted PCA via an endogenous PobA enzyme in *P. putida* KT2440. FIG. 8B is a schematic of the crystal structure of product-inhibited state of ecUbiC (PDB Code 1JD3). FIG. 8C shows a plasmid construct for UbiC evolution. UbiC gene is in-frame with reporter gene sfGFP which is under the control of PobR-DM (the 4HB sensor). FIG. 8D is a schematic illustrating a flow scheme for screening of ecUbiC library in *P. putida*.

FIG. 10A shows structure-based selection of mutational positions in UbiC based on the product-bound structure from X-ray crystallography (PDB code 1JD3). Whole protein (left) and targeted residues (right). Residues R116 and R126 were not mutated but neighboring residues were mutated to make the "flap" (Res 29-34) flexible, promoting exit of the product. M34 interacts with L30 and E31 interacts with R116 and R126. The residue numbers are based in the numbering in the published UbiC structure. Protein structures were created using PyMOL (The PyMOL Molecular Graphics System, Version 2.2, Schrödinger, LLC). FIG. 10B shows the UbiC library plated on LB agar petri dishes with different supplementations. The colonies that were picked based on the fluorescence intensity in the presence of 10 mM benzoate are marked with white arrows. Only a small portion of petri dish is shown here for clarity. Colonies from crowded regions were avoided since *P. putida* is capable of metabolizing benzoate, which would decrease the local concentration, and artificially relieve the UbiC inhibition. FIG. 10C shows quantitative evaluation of selected clones in liquid culture supplemented with different concentrations of benzoate (0, 10, and 20 mM). Error bars are standard deviations from three independent experiments.

FIG. 11A shows muconate production in shake flask with 50 mM glucose. FIG. 11B shows growth curves of the same strains measured on a plate reader in a 96-well plate. FIG. 11C are HPLC chromatograms for muconate CJ200 *P. putida* strain transformed with pBTL-2 derived plasmids: pBTL-2 empty vector (left); pPobR_ubiC-wt (wild-type *E. coli* UbiC; middle); pPobR_ubiC-C22 (low product inhibition variant UbiC-C22; right).

FIG. 13A is a schematic diagram of an exemplary plasmid construct for sensing PobA activity. *P. putida* PobA enzyme is expressed as sfGFP fusion and is under positive feedback regulation of PCA (scheme represented in FIG. 1B). FIG. 13B is a graph representing concentration-dependent 4HB response of *P. putida* KT2440 cells with native pobA deleted and pobA gene added to the plasmid (shown in FIG. 13A). FIG. 13C shows *P. putida* cells harboring the above plasmid construct and where pobA gene has been diversified (Theoretical library diversity>60,000). The library of cells was plated on 100 µM 4HB, scraped and analyzed using flow cytometry for fluorescence in the cells. The fluorescence distribution of the cells in the third round (middle panel) was similar to the distribution observed with cells harboring wild-type PobA (PobA-wt) (bottom panel).

FIG. 14A represents the *Acinetobacter baylyi* CatM promoter region used for selection of ccMA sensing in *P. putida* (SEQ ID NO: 12 and 13 (reverse complement). Partial amino acid sequences of CatM (SEQ ID NO: 14) and sfGFP (SEQ ID NO: 15) are also shown. Segments that were partially diversified or completely randomized are shown in red. FIG. 14B is a plot showing intracellular production and sensing of ccMA in *P. putida* using CatM transcription factor from *Acinetobacter baylyi* ADP1 and an optimal promoter sequence (CatM_C2). A strain capable of metabolizing PCA into ccMA as a final product (ccMA production strain) shows a clear dose-response with PCA. Another strain with a knockout mutation in PCA-ccMA pathway (Non-production strain) failed to show any dose-response with PCA. FIG. 14C shows the diversification of CatM inducer binding pocket. FIG. 14D shows a selected variant (CatM_C2.9) with low sensitivity for an ideal dose-response at high ccMA titer, that is >10 mM.

FIG. 15A shows the protocatechuate and catechol branches of the β-ketoadipate pathway in *P. putida* KT2440 and a heterologous shunt feed (green arrow) from shikimate pathway. Mutant *P. putida* (CJ390) consist of an added shunt (green arrow) and deleted genes of BKA metabolizing enzymes (PcaIJ) (red arrow). FIG. 15B shows low fluorescence in *P. putida* KT2440 with BKA sensor (pPcaR_promo that uses genomic PcaR expression in *P. putida*) and high fluorescence in a *P. putida* strain capable of accumulation of BKA when grown on LB medium (CJ390). FIG. 15C shows dose response of BKA sensor (pPcaR_promo) in *P. putida*. Native KT2440 cannot make BKA from glucose and BKA is transiently accumulated due to activity of PcaIJ. This results in significantly lower response compared to CJ390, which can convert glucose or spiked PCA and catechol into BKA and also accumulate BKA. FIG. 15D shows positions identified for diversification of putative BKA binding pocket in *P. putida* PcaR based on a homology model. FIG. 15E shows dose response plots of identified variants of PcaR that show low sensitivity and hence detection of high concentration of BKA titer.

FIG. 16A shows various substrates for phosphotriesterases, glucanases, esterases, and lipases with common leaving group, p-nitrophenol (pNP). FIG. 16B shows a hydrolytic reaction, breakdown of PXN to pNP. FIG. 16C shows flow cytometer histograms (y-axis population, x-axis: GFP fluorescence intensity) showing the *E. coli* cells (strain JW0451 with acrB gene deletion) (Baba et al., Mol. Syst. Biol. 2:2006.008, 2006) transformed with Biosensor/Biocatalyst plasmid (scheme shown in FIG. 1B) containing different PON1 sequences and grown under different induction conditions. UI: background fluorescence from cells without any pNP source to induce the TF; PXN: exogenous Paraoxon is converted intracellularly to pNP by the enzyme under study, activating the TF; pNP: TF induced by exogenously supplied pNP as a control/reference. FIG. 16D shows streaked LB-agar plates with *E. coli* JW0451 strain transformed with genetic sequences of PON1 variants. Relative activity levels are distinguishable by eye.

FIG. 17A shows PON1 structure with a bound competitive inhibitor 2HQ (PDB code 3SRG). Residue positions varied in library construction are indicated. FIG. 17B shows *E. coli* (DH5alpha, Thermo Fisher Scientific) cells transformed with Biosensor/Biocatalyst plasmid containing variants of PON1 gene based on Lib1 diversity and plated on LB+agar supplemented with 330 µM PXN. Several colonies (circled) showed brighter fluorescence than the surrounding colonies when visualized under an illuminator (ex/em 488/515). FIG. 17C shows Lib2 colonies showing a 'rare' bright colony in the whole population. The circled region is magnified (inset) for easy visualization of the bright colony. FIG. 17D shows total activity dose-response: Picked clones from the plates were grown in LB as liquid culture and supplemented with varying PXN concentration. The contrast ratio is defined as total fluorescence of the cells in the presence of PXN over the background fluorescence of the cells in the absence of PXN. FIG. 17E shows Specific Activity dose-response: In vitro paraoxonase spectrophotometric assay using clarified cell lysate, normalized for GFP fluorescence (equal GFP fused PON1 variant). FIG. 17F shows time accumulated activity of PON1 variant C3.3 (50 nM) and the scaffold (PON-H115W at 500 nM). For convenient illustration, the scaffold was made 10× higher in concentration to achieve a comparable timescale. The product, pNP, is measured by absorbance (410 nm). Error bars are standard deviation from two independent assays with different fractions from size exclusion chromatography. FIG. 17G shows Michaelis-Menten plot for PON1-C3.3 (50 nM) and PON1-H115W (500 nM). Error bars are the standard deviation of two independent assays using elution fractions from first half and second half of the chromatogram peak from size exclusion chromatography.

SEQUENCE LISTING

Figure 1A:
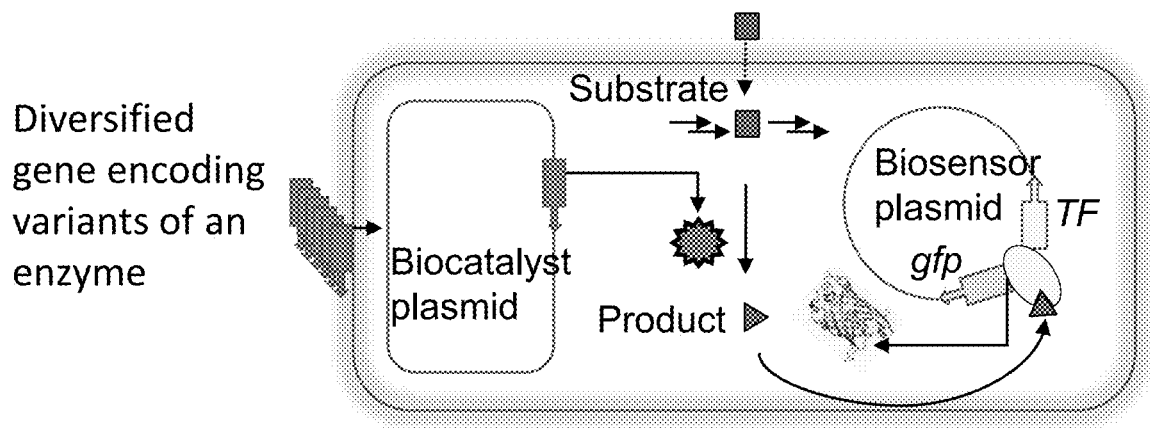
FIGS. 1A and 1B are schematics illustrating a "smart" microbial cell in two alternate exemplary schemes utilizing genetic sequences of a biocatalyst and a biosensor on two different plasmids (FIG. 1A) or on the same plasmid (FIG. 1B).

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 13, 2021, and is 103,248 bytes, which is incorporated by reference herein.

SEQ ID NO: 1 is the nucleic acid sequence of pPcaU1. Nucleotides 990-1823, pcaU gene; 1824-2105, promoter sequence; 2106-2822, sfGFP gene.

SEQ ID NO: 2 is the nucleic acid sequence of pPcaU1.1. Nucleotides 990-1823, pcaU gene; 1824-2104, promoter sequence; 2105-2821, sfGFP gene.

SEQ ID NO: 3 is the nucleic acid sequence of pPcaU1.2. Nucleotides 990-1823, pcaU gene; 1824-2104, promoter sequence; 2105-2821, sfGFP gene.

SEQ ID NO: 4 is the nucleic acid sequence of PcaU1.2.

SEQ ID NO: 5 is the amino acid sequence of PcaU1.2.

SEQ ID NO: 6 is the nucleic acid sequence of an exemplary 4HB sensor plasmid with PobR-DM (pBTL2_PobR-DM or pPobR). Nucleotides 990-1799, PobR-DM gene; 1800-1935, promoter sequence; 1936-2652, sfGFP gene.

SEQ ID NO: 7 is the nucleic acid sequence of an exemplary cis,cis-muconic acid sensor plasmid with CatM_C2 (pBTL2_CatM_C2 or pCatM_C2). Nucleotides 990-1898, CatM gene; 1899-2021, promoter sequence; 2022-2738, sfGFP gene.

SEQ ID NO: 8 is the nucleic acid sequence of a PcaR-regulated promoter for β-ketoadipic sensing.

SEQ ID NO: 9 is the nucleic acid sequence for a terephthalic acid sensor using TphR transcription factor from *Comamonas*.

SEQ ID NO: 10 is a partial nucleic acid sequence of a PcaU1 promoter region.

SEQ ID NO: 11 is a partial nucleic acid sequence of a PcaU1.1 promoter region.

SEQ ID NOs: 12 and 13 are the nucleic acid sequence and reverse complement, respectively of a CatM promoter and partial catM and sfGFP coding regions.

SEQ ID NO: 14 is the amino acid sequence of a portion of a CatM protein.

SEQ ID NO: 15 is the amino acid sequence of a portion of a sfGFP protein.

SEQ ID NO: 16 is the amino acid sequence of an exemplary PobR double mutant protein.

SEQ ID NOs: 17 and 18 are the nucleic acid and amino acid sequences, respectively, of an exemplary wild type UbiC protein.

SEQ ID NO: 19 is the amino acid sequence of an exemplary PcaR protein.

SEQ ID NO: 20 is the nucleic acid sequence of a TphR promoter.

SEQ ID NO: 21 is the nucleic acid sequence of a β-ketoadipate sensor that utilizes genomic PcaR expression and an optimal promoter sequence with sfGFP as a reporter. Nucleotides 987-1211, PcaR-regulated promoter sequence; 1212-1928, sfGFP gene.

SEQ ID NO: 22 is the nucleic acid sequence of an exemplary β-ketoadipate sensor plasmid with PcaR sensor and sfGFP reporter (pBTL2_PcaR_sfGFP or pPcaR). Nucleotides 990-1862, PcaR sensor; 1863-2157, PcaR-regulated promoter; 2158-2874, sfGFP gene.

SEQ ID NO: 23 is the nucleic acid sequence of an exemplary CatM regulated promoter in ccMA sensor for reduced signal output to prevent saturation of fluorescence. The promoter (CatM_A9) can replace nucleotides 1899-2021 in CatM_C2 (SEQ ID NO: 7).

SEQ ID NO: 24 the nucleic acid sequence of CatM_C2.9 in ccMA sensor with weaker inducer sensitivity than the native sequence. The nucleotide sequence can replace nucleotides 990-1898 for CatM gene in SEQ ID NO: 7.

SEQ ID NO: 25 is the amino acid sequence of CatM_C2.9 which shows weaker inducer sensitivity to ccMA compared to native CatM.

SEQ ID NO: 26 is the amino acid sequence of PcaR-G5 for a low sensitivity BKA sensor.

SEQ ID NO: 27 is the amino acid sequence of PcaR-F6 for a low sensitivity BKA sensor.

SEQ ID NO: 28 is the amino acid sequence of PcaR-H6 for a low sensitivity BKA sensor.

SEQ ID NO: 29 is the nucleic acid sequence of an exemplary sensor+enzyme consisting of pPobR as the backbone and ubiC-wt gene in the same reading frame as the sfGFP reporter gene (pPobR_ubiC-wt). Nucleotides 990-1799, PobR-DM gene; 1800-1935, promoter sequence; 1936-2652, sfGFP gene; 2672-3162, ubiC-wt gene.

SEQ ID NO: 30 is the nucleic acid sequence of an exemplary sensor+enzyme plasmid consisting of pPcaU1.2 as the backbone and pobA-wt gene in the same reading frame as the sfGFP reporter gene (pPcaU1.2_pobA-wt). Nucleotides 990-1823, PcaU1.2 gene; 1824-2104, promoter sequence; 2105-2821, sfGFP gene; 2840-4024, pobA-wt gene.

SEQ ID NO: 31 is the nucleic acid sequence of an exemplary sensor+enzyme consisting of PobR-DM derived pNP sensor with PON1 enzyme gene in the same reading frame as the sfGFP reporter gene. Nucleotides 98-907, pNPmut1.1 gene; 908-1043, promoter region; 1044-1760, sfGFP gene; 1779-2840, PON1-G3C9 gene.

SEQ ID NO: 32 is the amino acid sequence of an exemplary PON1-G3C9.

SEQ ID NOs: 33-50 are nucleic acid sequences of oligonucleotide primers.

SEQ ID NOs: 51-55 are amino acid sequences of mutational library peptides.

DETAILED DESCRIPTION

Disclosed herein is development and improvement of biosensors for biocommodities, which in some examples, are useful for development of industrially relevant organisms such as *P. putida*. In one embodiment, a PcaU-based sensor optimized in *P. putida* KT2440 was developed that senses both PCA and catechol (with an appreciable contrast ratio), which are the key intermediates in the carbon flow via PCA or catechol branches of the β-ketoadipate pathway.

In another embodiment, a PobR-based sensitive and specific sensor for 4HB was established in *P. putida*. 4HB is an important intermediate in the metabolic pathways for production of industrially important aromatic compounds in the manufacturing of bioplastics. The chorismate lyase UbiC that produces 4HB (e.g., *E. coli* UbiC) suffers from product inhibition and is a significant bottleneck in the shikimate pathway. Instead of the traditional methodology of site directed mutations in the product binding site to alleviate production inhibition, disclosed herein is use of a 4HB-binding PobR transcription factor to identify UbiC variants with reduced product inhibition. For this, the structurally similar benzoate that binds to UbiC was used as a surrogate product molecule to generate a high throughput library that was screened by fluorescence output from the 4HB biosensor. The enzyme kinetic parameters of the best selected variant had higher $K_p$, indicating lower product binding affinity, and increased $k_{cat}$ indicating higher turnover number. When the UbiC variant with reduced product inhibition was expressed in a muconate production strain, the product yield was improved by 50-200% (e.g., 130% when expressed on plasmid or 60% when genomically integrated).

In a further embodiment, a CatM regulon from *Acinetobacter baylyi* APD1 was optimized in the promoter for muconate sensing in *P. putida*. The sensor detected intracellular muconate production from glucose, PCA, benzoate and catechol. In a still further embodiment, the endogenous PcaR in *P. putida* was utilized for sensing β-ketoadipic acid (BKA) production inside a cell. In another embodiment, PcaR from *P. putida* was expressed via a plasmid and intracellular BKA production from glucose, PCA and catechol was detected in a PcaR 'knock out' *P. putida* strain.

With only a few examples of established sensor-reporter systems in *P. putida* (Garmendia et al., *Microb. Biotechnol.* 1:236-246, 2008), and limited efforts to establish sensor-reporter systems in non-model organisms (DeLorenzo et al., *ACS Synth. Biol.* doi:10.1021/acssynbio.7b00192), the present disclosure demonstrates detection of industrially important aromatic compounds and compounds from aromatic catabolic pathway in *P. putida*.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. All database accession numbers (such as GenBank or UniProt accession numbers) are incorporated herein by reference in their entirety, as present in the database on Dec. 19, 2017. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

4-hydroxybenzoic acid (4HB): A value-added chemical with the structure:

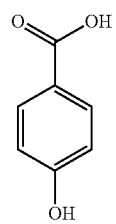

β-ketoadipic acid (BKA): A polymer precursor with the structure:

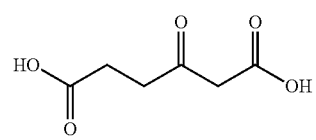 [SMILES: O=C(O)CCC(=O)CC(=O)O]

Biocatalyst: A biological molecule (such as a protein) that initiates a biochemical reaction and/or increases the rate of a biochemical reaction. In some examples, a biocatalyst is an enzyme.

Biomanufacturing: A process to convert renewable feedstocks into value-added chemicals using microbial cells and/or enzymes.

Biosensor: A biological molecule (such as a nucleic acid, peptide, or protein) that can detect a change in environment, for example, in a dose-dependent manner. In some examples, a biosensor is a protein (such as a transcription factor) that can sense a change in concentration of a small molecule in or around a cell. The biosensor may be coupled (directly or indirectly) to a reporter, including but not limited to an antibiotic resistance gene, a gene encoding a fluorescent protein (such as a green fluorescent protein), or a metabolic gene (such as lacZ). The reporter then indicates the presence and/or amount of the detected molecule, for example, by antibiotic resistance, fluorescence, or color change.

CatM: A transcription factor belonging to LysR family from *Acinetobacter baylyi* (e.g., *A. baylyi* ADP1). CatM binds to cis,cis-muconic acid and regulates the metabolism of the molecule by activating the cat gene expression. The GenBank Accession number P07774 is an exemplary wild-type CatM amino acid sequence.

Chorismate pyruvate lyase (UbiC): An enzyme that catalyzes removal of the pyruvyl group from chorismate, producing 4-hydroxybenzoate (4HB).

cis,cis-muconic acid (ccMA): Also referred to as muconate. A precursor of adipic acid, which is utilized for nylon 6,6 production. ccMA has the structure:

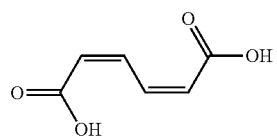

Expression control element: One or more sequences that control or regulate transcription and/or translation of a nucleic acid, such as operators, promoters, enhancers, leader sequences, transcription terminators, start and/or stop codons, internal ribosome entry sites (IRES), splicing signals, and polyadenylation signals.

Heterologous: Originating from a different genetic source or species. A gene that is heterologous to a prokaryotic cell originates from an organism or species other than the prokaryotic cell in which it is expressed. Methods for introducing a heterologous gene in a cell or organism are well known in the art, for example transformation with a nucleic acid, including electroporation, lipofection, particle gun acceleration, and homologous recombination.

Hydrolase: An enzyme that uses water molecule to catalyze the breakdown of substrates into smaller products. A labile chemical bond attaching the head group with a leaving group undergoes breaking when attacked by a water molecule to release the leaving group. Surrogate substrates for various hydrolases consist of p-nitrophenol (pNP) as a leaving group. A few anthropogenic molecules used as pesticides (for example Paraoxon) have pNP as a leaving group and can undergo hydrolysis in the presence of a hydrolase (for example a phosphotriesterase).

Isolated: An "isolated" biological component (such as a nucleic acid molecule, protein, or cell) has been substantially separated or purified away from other biological components in the cell of the organism, or the organism itself, in which the component occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

It is understood that the term "isolated" does not imply that the component is free of trace contamination, and can include molecules that are at least 50% isolated, such as at least 50%, 55%, 60%, 65%, 70%, 75%, 80%, 85%, 90%, 95%, 98%, 99%, or even 100% isolated.

Modified: A "modified" nucleic acid or polypeptide is one that has a sequence that is not naturally occurring or has a sequence that is made by an artificial combination of two or more otherwise separated segments of sequence. A modified nucleic acid or polypeptide is often produced by chemical synthesis or, more commonly, by the artificial manipulation of isolated segments of nucleic acids, e.g., by genetic engineering techniques.

Operably linked: A first nucleic acid is operably linked with a second nucleic acid when the first nucleic acid is placed in a functional relationship with the second nucleic acid. For instance, a regulatory region is operably linked to a coding sequence if the regulatory region affects the transcription or expression of the coding sequence. Generally, operably linked DNA sequences are contiguous and, where necessary to join two protein-coding regions, in the same reading frame.

PcaR: A transcription factor belonging to the IclR family from *Pseudomonas putida* KT2440. PcaR binds to β-ketoadipic acid (BKA) and regulates the expression of pca genes that divert BKA to TCA cycle. GenBank Accession No. Q88N41 is an exemplary amino acid sequence of PcaR.

PobR: A transcription factor involved in regulation of enzymes for catabolism of 4HB. PobR is a member of the IclR family. It binds to 4HB and regulates the expression of PobA enzyme that metabolizes 4HB into PCA. GenBank Accession No. Q43992 is an exemplary wild type (unmodified) PobR amino acid sequence. A double mutation version including deletion of L141 and L220V mutation has enhanced sensitivity and response to 4HB.

Production strain: Organisms that can be used for production of value-added chemicals from renewable feedstocks in a laboratory or an industrial environment. In some examples, a production strain is a model microbial strain such *Escherichia coli* or *Saccharomyces cerevisiae*. In other examples, a production strain is a non-model organism such as *Pseudomonas putida* or *Acinetobacter baylyi*.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element.

Protocatechuate (PCA): Also known as 3,4-dihydroxybenzoate (3,4-DHB) or protocatechuic acid (CAS Reg. No. 99-50-3). A compound having the structure:

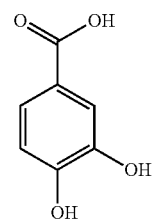 [SMILES: O=C(O)c1ccc(O)c(O)c1]

PCA is utilized commercially in the production of food preservatives and pharmaceutical intermediates.

PcaU: A transcription factor belonging to the IclR family of transcription factors and involved in regulation of enzymes for catabolism of PCA. PcaU is a member of the Icl family that binds to a consensus operator sequence in the pca regulon. It binds PCA and activates the expression of pca genes. GenBank Accession No. O83046 is an exemplary wild type (unmodified) PcaU amino acid sequence.

Recombinant: A nucleic acid or protein that is not naturally occurring or has a sequence that is made by an artificial combination of two otherwise separated segments of nucleotides or amino acids. This artificial combination is often accomplished by chemical synthesis or, more commonly, by the artificial manipulation of isolated segments of nucleic acids, e.g., by genetic engineering techniques such as those described in Sambrook et al. *Molecular Cloning: A Laboratory Manual*, 3$^{rd}$ ed., Cold Spring Harbor Laboratory Press, N Y, 2001. The term recombinant includes nucleic acids or proteins that have been altered solely by addition, substitution, or deletion of a portion of the nucleic acid sequence or amino acid sequence, respectively.

Terephthalic acid (TPA): A commodity chemical and polymer precursor with the structure:

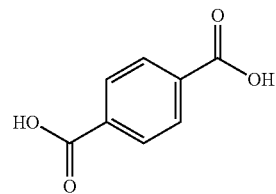 [SMILES: O=C(O)c1ccc(C(=O)O)cc1]

TphR: A transcription factor belonging to the IclR family from *Comamonas* genus. TphR binds to terephthalic acid (TPA) to express downstream genes involved in transport of TPA into the cell. GenBank reference sequence WP_012837656.1 is an exemplary amino acid sequence of TphR.

Transduced and Transformed: A vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule is introduced into such a cell, including transformation with plasmid vectors, and introduction of naked DNA by electroporation, lipofection, and particle gun acceleration.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and gram positive bacterial cells. Exemplary vectors include those for use in *E. coli* or *P. putida*.

II. Biosensors

Disclosed herein are biosensors for use in industrially relevant organisms (e.g., *P. putida*). In some examples, the biosensor is modified from a naturally occurring biosensor (e.g., transcription factor) and exhibits improved sensitivity and/or specificity or reduced sensitivity with broader applicability in a new host organism compared to the unmodified biosensor (such as a biosensor from a model organism, for example, from *E. coli*).

In particular embodiments disclosed herein a biosensor includes a transcription factor that is regulated by a molecule of interest "sensed" by the biosensor (such as PCA, 4HB, ccMA, BKA, TPA, or pNP). In some examples, the molecule of interest alters the activity of the transcription factor and alters metabolism or production of the sensed molecule. In some examples, the biosensor participates in positive or negative feedback regulation of the sensed molecule (see, e.g., FIG. 1B). Exemplary sensor/sensed molecule pairs are shown in Table 1.

Table 1. Exemplary biosensors and "sensed" molecules

TABLE 1

Exemplary biosensors and "sensed" molecules

| Sensor (Transcription factor) | Sensed molecule |
|---|---|
| PcaU | PCA |
| PobR | 4HB |
| CatM | ccMA |
| PcaR | BKA |
| TphR | TPA |
| PobR-derived pNPmut | pNP |

In one embodiment, the biosensor is a biosensor for PCA that is modified for use in *P. putida*. The biosensor may further include one or more expression control elements operably linked to a nucleic acid encoding a reporter (such as an antibiotic resistance gene, a fluorescent protein-encoding gene, or a metabolic gene). In some examples, the biosensor for PCA encodes a PcaU protein with one or more amino acid changes compared to a wild type PcaU protein (such as a PcaU protein from *Acinetobacter* baylyi, e.g., GenBank Accession No. 083046: SEQ ID NO: 56). For example, a modified PCA biosensor may include a nucleic acid encoding a PcaU protein with an amino acid substitution at amino acid position 147 and/or amino acid position 148 compared to the wild type PcaU protein. In non-limiting examples, the modified PCA biosensor encodes a PcaU protein with the amino acid glycine, serine, or proline at position 147 and/or the amino acid tyrosine or phenylalanine at position 148. Exemplary PcaU amino acid substitutions include T147G/D148Y, T147S/D148F or T147P/D148F.

In some examples, the PcaU protein is encoded by a nucleic acid sequence comprising or consisting of SEQ ID NO: 4 and comprises or consists of the amino acid sequence of SEQ ID NO: 5. In other examples, the PcaU protein is encoded by a nucleic acid sequence with at least about 85% sequence identity (such as at least about 86%, 87%, 88%, 89%, 90%, 91%, 92%, 93%, 94%, 95%, 96%, 97%, 98%, 99%, or 100% identity) to SEQ ID NO: 4, wherein the nucleic acid encodes a PcaU protein with an amino acid substitution at amino acid position 147 and/or amino acid position 148 compared to the wild type PcaU protein. In other examples, the PcaU protein has at least about 90% sequence identity (such as at least about 91%, 92%, 93%, 94%, 95%, 96%, 97%, 98%, 99%, or 100% identity) to SEQ ID NO: 5, wherein the PcaU protein has an amino acid substitution at amino acid position 147 and/or amino acid position 148 compared to the wild type PcaU protein.

In some embodiments, the modified PCA biosensor includes one or more modifications to expression control sequences operably linked to the nucleic acid encoding the reporter protein. In some examples, the modifications include one or more of those shown in FIG. 2A, for example, a one base deletion between the operator and the promoter, one or more nucleic acid changes in the −35 region (such as 1, 2, or more changes), and/or one or more nucleic acid changes in the −10 region (such as 1, 2, or more changes). In one non-limiting embodiment, the expression control sequence has the nucleic acid sequence shown in FIG. 2A (pPcaU1.1), such as the sequence of nucleotides 1930-1988 of SEQ ID NO: 2.

In additional embodiments, the modified PCA biosensor includes one or more modifications to expression control sequences (such as one or more of the changes shown in FIG. 2A) and a nucleic acid encoding a PcaU protein with an amino acid substitution at amino acid position 147 and/or amino acid position 148 compared to the wild-type PcaU protein. In a particular example, the modified PCA biosensor includes the sequence of nucleotides 1930-1988 of SEQ ID NO: 2 and the PcaU protein is encoded by a nucleic acid sequence comprising or consisting of SEQ ID NO: 4, wherein the nucleic acid encodes a PcaU protein with an amino acid substitution at amino acid position 147 and/or amino acid position 148 compared to the wild type PcaU protein (such as those described above). In further embodiments, the modified PCA biosensor includes a nucleic acid encoding a fluorescent protein reporter molecule. In some examples, the fluorescent protein is a green fluorescent protein (GFP), for example, a superfolder GFP (sfGFP).

In additional embodiments, the modified PCA biosensor is incorporated in a vector. The vector can be a plasmid vector for replication and/or expression in a bacterial cell. In one example, the vector is for expression in *P. putida*. In one non-limiting example, the vector includes or consists of the nucleic acid sequence of SEQ ID NO: 1 (pPcaU1.1), or a nucleic acid sequence with at least 90% sequence identity (such as 91%, 92%, 93%, 94%, 95%, 96%, 97%, 98%, 99%, or 100% identity) with SEQ ID NO: 2. In further examples, the vector includes or consists of the nucleic acid sequence of SEQ ID NO: 3 (pPcaU1.2), or a nucleic acid sequence with at least 90% sequence identity (such as 91%, 92%, 93%, 94%, 95%, 96%, 97%, 98%, 99%, or 100% identity) with SEQ ID NO: 3.

In other embodiments, the biosensor is a biosensor for 4HB, such as PobR. In some examples, the biosensor includes a nucleic acid encoding a PobR DoubleMut (PobR-DM) protein (Jha et al., *Proteins Struct. Funct. Bioinforma* 83:1327-1340, 2015) that carries two mutations (deletion of L141 and L220V mutation) on the wild-type sequence (GenBank Accession No. Q43992), along with the wild-type promoter region from *Acinetobacter baylyi* (such as *A. baylyi* ADP1). In some examples, the PobR-DM protein includes or consists of the amino acid sequence of SEQ ID NO: 16. In one embodiment, the reporter gene sequence (e.g., sfgfp) is added downstream of the promoter and the whole cassette is inserted in a vector (such as a pBTL-2 vector). In some examples, the promoter includes or consists of nucleotides 1800-1935 of SEQ ID NO: 6. The vector can be a plasmid vector for replication and/or expression in a bacterial cell. In one example, the vector is for expression in *P. putida*. In one non-limiting example, the vector includes or consists of the nucleic acid sequence of SEQ ID NO: 6, or a nucleic acid sequence with at least 90% sequence identity (such as 91%, 92%, 93%, 94%, 95%, 96%, 97%, 98%, 99%, or 100% identity) with SEQ ID NO: 6.

Figure 13A:
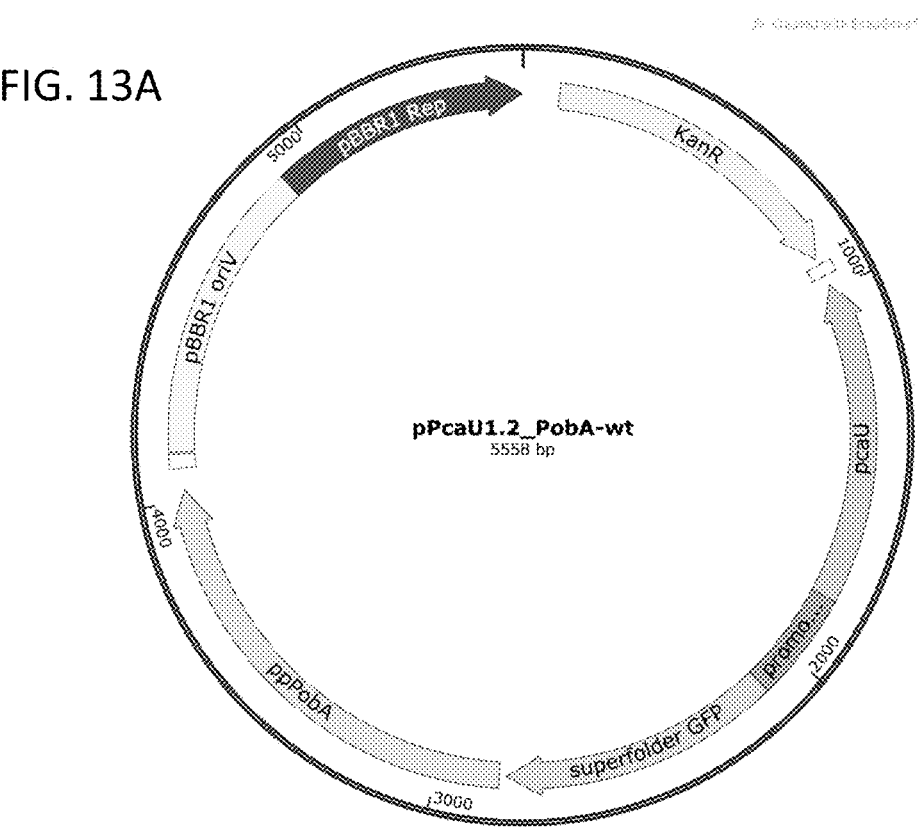
FIGS. 13A-13C are a series of panels showing 4HB monooxygenase (PobA) activity sensing and library screening.

In additional embodiments, the biosensor includes a transcription factor for cis,cis-muconic acid (ccMA), such as CatM. In some examples, the biosensor includes a nucleic acid encoding a CatM polypeptide and may further include a wild-type CatM promoter optimized for activity in *P. putida*. The CatM promoter region includes the Shine Dalgarno RBS sequence AAGGAG and three mutations in −35 region (AGA 4 CCA) and two mutations in the −10 promoter proximal CatM operator region (TA 4 AC) (FIG. 13A). CatM which is a repressor, upon binding to ccMA regulates the expression of a downstream reporter gene (such as sfgfp). In some examples, a sensor plasmid for ccMA includes a pBTL-2 plasmid backbone and a nucleic acid encoding wild-type CatM from *Acinetobacter baylyi* (e.g., GenBank Accession No. P07774 or nucleotides 990-1898 of SEQ ID NO: 7). In one non-limiting example, the vector includes or consists of the nucleic acid sequence of SEQ ID NO: 7, or a nucleic acid sequence with at least 90% sequence identity (such as 91%, 92%, 93%, 94%, 95%, 96%, 97%, 98%, 99%, or 100% identity) with SEQ ID NO: 7.

In another embodiment, the biosensor is a biosensor for BKA, such as a PcaR operator region and −35/−10 regions based on PcaI promoter in *P. putida* and inclusion of *P. putida* compatible RBS sequence AAGGAG (same as *E. coli* Shine Dalgarno sequence). In some examples, a sensor plasmid for BKA includes a pBTL-2 plasmid backbone and a nucleic acid encoding wild-type PcaR from *P. putida* (e.g., UniProtKB Accession No. Q88N41; SEQ ID NO: 19). In some examples, the biosensor encodes an amino acid sequence with at least 90% (such as at least 95%) sequence identity with SEQ ID NO: 19 or including or consisting of the sequence of SEQ ID NO: 19, or nucleotides 990-1862 in SEQ ID NO: 22. In one non-limiting example, the promoter is a PcaR promoter that includes or consists of the nucleic acid sequence of SEQ ID NO: 8, or a nucleic acid sequence with at least 90% sequence identity (such as 91%, 92%, 93%, 94%, 95%, 96%, 97%, 98%, 99%, or 100% identity) with SEQ ID NO: 8 or nucleotides 1863-2157 of SEQ ID NO: 22.

In other embodiments, the biosensor is a biosensor for TPA. A sensor plasmid for terephthalic acid (TPA) includes the nucleotide sequence of TphR transcription factor and an optimized intergenic sequence from tphR-tphC regulon from *Comamonas testosteroni*. In the sensor plasmid, tphC promoter regulates the expression of a reporter gene (such as a sfgfp gene), which is also preceded by an optimal *P. putida* RBS site (AAGGAG). In one non-limiting example, the biosensor includes or consists of the nucleic acid sequence of SEQ ID NO: 9, or a nucleic acid sequence with at least 90% sequence identity (such as 91%, 92%, 93%, 94%, 95%, 96%, 97%, 98%, 99%, or 100% identity) with SEQ ID NO: 9. In some examples, the TphR promoter includes or consists of the nucleic acid sequence of SEQ ID NO: 20.

III. Modified Biocatalysts

Disclosed herein are biocatalysts modified for use in industrially relevant organisms (e.g., *P. putida*). In some examples, the modified biocatalyst exhibits improved activity in the organism compared to the unmodified biocatalyst (such as a native biocatalyst, for example, from *E. coli*).

In one embodiment, the modified biocatalyst is a modified chorismate pyruvate-lyase (UbiC) from *E. coli* that is modified for use in *P. putida*, for example, for enhanced productivity. A novel screening approach for relieved product inhibition included utilizing the product sensor with the product surrogate benzoate as an inhibitor. In some examples, the product surrogate at a concentration of 3 mM is capable of inhibiting the biocatalyst by 50% but at that concentration, it does not show any activation of the 4HB sensor.

In some embodiments, the modified UbiC includes of one or more (such as 1, 2, 3, or more) mutations at amino acid positions 31, 34, 76, 78, 80, 90, 92, and/or 114 of SEQ ID NO: 18. In some examples, combination of 2 or 3 mutations result in decreased product inhibition, which also contributes to enhanced enzyme turnover or $k_{cat}$. Exemplary substitutions in UbiC include E31Q, M34V, I78V, L80V and T92A. In some examples, combinations of the substitutions, for example, E31Q/T92A, E31Q/I78V/L80V, E31Q/I78V/T92A, M34V/I78V, E31Q/M34V, show a gain-of-function.

In some examples, the UbiC protein is encoded by a nucleic acid sequence comprising or consisting of SEQ ID NO: 17 and comprises or consists of the amino acid sequence of SEQ ID NO: 18. In other examples, the UbiC protein is encoded by a nucleic acid sequence with at least about 85% sequence identity (such as at least about 86%, 87%, 88%, 89%, 90%, 91%, 92%, 93%, 94%, 95%, 96%, 97%, 98%, 99%, or 100% identity) to SEQ ID NO: 17, wherein the nucleic acid encodes one or more substitutions at amino acid positions 31, 34, 76, 78, 80, 90, 92, and/or 114 compared to the wild type UbiC protein. In other examples, the UbiC protein has at least about 90% sequence identity (such as at least about 91%, 92%, 93%, 94%, 95%, 96%, 97%, 98%, 99%, or 100% identity) to SEQ ID NO: 18, wherein the UbiC protein one or more substitutions at amino acid positions 31, 34, 76, 78, 80, 90, 92, and/or 114 compared to the wild type UbiC protein.

In another embodiment, the modified biocatalyst is a modified CatM polypeptide. In some embodiments, the modified CatM includes a mutation at one or more (such as 1, 2, 3, or more) of amino acid positions 97, 127, 128, and/or 147 of SEQ ID NO: 25. In some examples, the variant CatM_C2.9 includes the following mutations in the inducer binding pocket: V97I, G127A, T128A and L147V (SEQ ID NO 25).

In another embodiment, the modified biocatalyst is a modified PcaR polypeptide. Exemplary modified PcaR polypeptides include or consist of the amino acid sequences of PcaR-G5 (SEQ ID NO: 26), PcaR-F6 (SEQ ID NO: 27) and PcaR-H6 (SEQ ID NO: 28).

In another embodiment, the modified biocatalyst is a modified paraoxonase (PON1). In some embodiments, the modified PON1 includes a mutation at amino acid 115 and one or more (such as 1, 2, 3, or more) mutations at amino acid positions 69, 70, 71, and/or 73 of SEQ ID NO: 32. In some examples, combination of 2, 3, or 4 mutations in combination with H115W result in enhanced enzyme activity. Exemplary substitutions in PON1 include L69V, K70Y/Q/L/H/F, Y71V/I/L, G73/S/A. In some examples, combinations of the substitutions, for example, H115W/L69V/K70Y/Y71V; H115W/L69V/K70Q/Y71I; H115W/L69V/K70L/G73S; H115W/L69V/K70Q/Y71I/G73A; H115W/L69V/K70H/Y71V/G73S; H115W/L69V/K70L; H115W/L69V/K70Q/Y71V/G73A; H115W/L69V/K70Q/Y71L/G73A; and H115W/L69V/K70F/Y73V show enhanced activity.

In some examples, the PON1 protein is encoded by a nucleic acid sequence comprising or consisting of nucleotides 1779-2840 of SEQ ID NO: 31 and/or comprises or consists of the amino acid sequence of SEQ ID NO: 32. In other examples, the PON1 protein is encoded by a nucleic acid sequence with at least about 85% sequence identity (such as at least about 86%, 87%, 88%, 89%, 90%, 91%, 92%, 93%, 94%, 95%, 96%, 97%, 98%, 99%, or 100% identity) to SEQ ID NO:32, wherein the nucleic acid encodes an amino acid substitution at amino acid position 115 and one or more substitutions at amino acid positions 69, 70, 71, and/or 73 compared to the wild type PON1 protein. In other examples, the PON1 protein has at least about 90% sequence identity (such as at least about 91%, 92%, 93%, 94%, 95%, 96%, 97%, 98%, 99%, or 100% identity) to SEQ ID NO: 32, wherein the PON1 protein includes an amino acid substitution at amino acid position 115 and one or more substitutions at amino acid positions 69, 70, 71, and/or 73 compared to the wild type PON1 protein.

IV. Methods of Using Biosensors

Figure 1B:
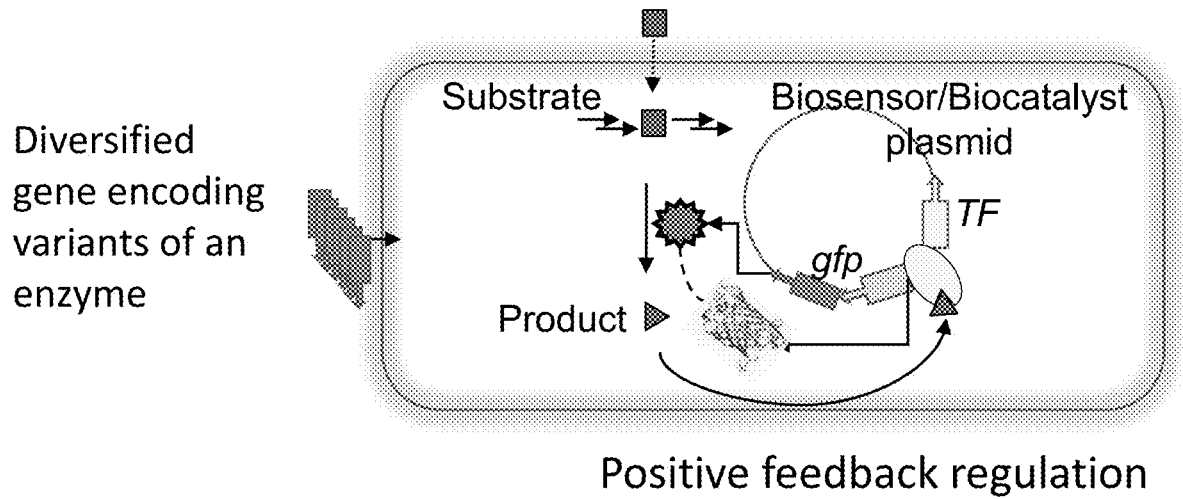

Also disclosed herein are methods of utilizing biosensors (e.g., a modified or improved biosensor) to identify and/or select for biocatalysts (e.g., enzymes) with improved activity or strains with gain-of-function. FIGS. 1A and 1B show two exemplary alternate methods to set up microbial cells for biocatalysis and biosensing. In the two plasmid system (FIG. 1A), a nucleic acid encoding the biocatalyst and the genetic sequences of sensor-reporter are on separate plasmids. A single plasmid system where the biocatalyst expression is under positive feedback regulation (FIG. 1B) offers convenience during transformation in microbial cells and can amplify the output signal difference (e.g., fluorescence or other visually detectable signal) in two microbial cells with differential activities (e.g., via positive feedback).

The sensor plasmid (FIG. 1A) can also be used alone in microbial cells where targeted or random mutations are performed for strain evolution. The optimization of a strain for increased product titer involves hundreds of mutagenesis loci, and the efficiency of the variant is coupled to the activation of the sensor in a correlated increase in fluorescence of the cell.

The screening of the microbial library (each cell containing certain variations at the genetic level) is possible via both flow cytometry (Jha et al., *Nucl. Acids Res.* 428150-8160, 2014) or on a solid growth media (e.g., petri dish) and selection based on the fluorescence of the individual cell (for flow cytometry) or fluorescence (or other visually detectable signal) of the colonies on a solid growth media. If the reporter gene in the sensor plasmid is a survival enhancing gene (for example the protein product of the gene provides resistance to a suitable antibiotic or the protein product of the gene provides a suitable nutrient to the auxotroph), the screening can be carried out based on the growth rate.

Exemplary methods of utilizing the disclosed biosensors are described in Examples 1-7. In some examples, bacterial cells (e.g., *P. putida*) are transformed with a plasmid encoding a disclosed biosensor and a reporter (such as a fluorescent protein). The cells can be transformed with variants of the biosensor (such as a library encoding variants of the biosensor). The cells can be screened for biosensors with improved function, such as increased sensitivity or specificity for the sensed molecule. In other examples, bacterial cells (e.g., *P. putida*) are transformed with a plasmid encoding a disclosed biosensor and a reporter (such as a fluorescent protein). The cells are also transformed with a nucleic acid encoding a biocatalyst, which may be on the same or a different plasmid (e.g., FIG. 1A or 1B). Exemplary biosensor/biocatalyst pairs are shown in Table 1. The cells can be transformed with variants of the biocatalyst and can be screened for biocatalysts with improved function, such as increased production of the product of the biocatalyst.

V. Bacterial Strains

Bacteria including nucleic acids for one or more biosensors (such as a PCA biosensor, 4HB biosensor, cis,cis muconic acid biosensor, β-ketoadipic acid sensor, terephthalic acid sensor, and/or pNP biosensor) and/or one or more improved enzymes (such as ecUbiC or PON1) are disclosed. In some examples, the bacteria are *P. putida* or *E. coli*.

In one embodiment, a bacterial strain disclosed herein is a population of *P. putida* cells including a PCA biosensor or a vector including a PCA biosensor disclosed herein. In some non-limiting examples, the bacterial strain is *P. putida* including a pPcaU1.1 (SEQ ID NO: 2) or pPcaU1.2 plasmid (SEQ ID NO: 3). In other embodiments, a bacterial strain is a population of *P. putida* cells including 4HB biosensor or a vector including a 4HB biosensor disclosed herein, such as a plasmid including PobR-DM (e.g., pBTL2_PobR-DM, such as SEQ ID NO: 6). In further embodiments, a bacterial strain is a population of *P. putida* cells including a ccMA biosensor or a vector including a ccMA biosensor disclosed herein, such as a plasmid including CatM_C2 (e.g., pBTL2_CatM_C2, such as SEQ ID NO: 7) or wherein the promoter sequence is replaced by CatM_A9 (SEQ ID NO: 23) or CatM gene is replaced by CatM_C2.9 (SEQ ID NO: 24). In another embodiment, a bacterial strain is a population of *P. putida* cells including a BKA biosensor or a vector including a BKA biosensor disclosed herein, such as a plasmid including a modified PcaR promoter that uses endogenous PcaR expression in *P. putida* (e.g., SEQ ID NO: 8) or a plasmid including a PcaR gene, and modified promoter (e.g., SEQ ID NO: 22). In a further embodiment, a bacterial strain is a population of *P. putida* cells including a TPA biosensor or a vector including a TPA biosensor disclosed herein, such as a plasmid including a TphR from *Comamonas* (e.g., SEQ ID NO: 9). In another embodiment, a bacterial strain is a population of *P. putida* cells including a PobR-derived pNP mutant or a vector including a PobR-derived pNP mutant disclosed herein (e.g., SEQ ID NO: 31).

Exemplary bacterial strains include a biosensor (such as one of the modified biosensors disclosed herein) and one or more molecules involved in the pathway of interest for the biosensor. Thus, in some examples, the bacterial strains include one or more of the biocatalysts listed in Table 2 for each biosensor. In some examples, the one or more biocatalysts included in the bacterial strain with the biosensor are naturally occurring, modified (e.g., by introduction of one or more amino acid substitutions, deletions, and or insertions), heterologous (e.g., introduced from another strain or another species), or a combination of two or more thereof.

Table 2. Exemplary biosensor/biocatalysts combinations in bacterial strains Biosensor Biocatalyst(s)

TABLE 2

Exemplary biosensor/biocatalysts combinations in bacterial strains

| Biosensor | Biocatalyst(s) |
|---|---|
| PCA (PcaU) | AsbF, PobA, 3-deoxy-D-arabino-heptulosonate-7-phosphate synthase (DAHP synthase isozymes aroG, aroF, aroH), VanAB, Fcs, Ech, Vdh |
| 4HB (PobR-DM) | DAHP synthases, UbiC, Fcs, Ech, Vdh, |
| cis,cis-muconic acid (CatM) | DAHP synthases, AroY (ecdD, ecdB), PobA, AsbF, VanAB, CatA, BenABC, BenD, Dmp KMLNOP, Fcs, Ech, Vdh |
| β-ketoadipic acid (PcaR) | PobA, VanAB, CatA, BenABC, BenD, Dmp KMLNOP, Fcs, Ech, Vdh, PcaHG, PcaBCD, CatBC |
| Terephthalic acid (TphR) | DAHP synthases, UbiC, Fcs, Ech, Vdh, PHA2, BsdBCD |
| p-nitrophenol (PobR derived pNPmut) | Hydrolases (glucanase, xylanase, lipase, esterase, phosphodiesterase, phosphotriesterase) |

Bacterial cells are available from numerous sources, including commercial sources known to those skilled in the art, such as the American Type Culture Collection (ATCC; Manassas, Va.). Commercial sources of cells used for recombinant protein expression also provide instructions for usage of such cells. Suitable bacteria for use in the methods disclosed herein include but are not limited to *Pseudomonas* (e.g., *P. putida*) or *Escherichia* (e.g., *E. coli*). The modified biosensors can also be used to modify biocatalysts in other genera, including but not limited to *Acinetobacter* (e.g., *Acinetobacter baylyi*) and *Rhodococcus*. Bacterial cells are available commercially, for example from American Type Culture Collection (Manassas, Va.).

One representative bacterial system for replication and/or expression of one or more of the disclosed biosensors or biocatalysts is *P. putida*. In some examples, the vector is a broad host range vector, such as pBTBX vectors (Prior et al., *Biotechnol. Bioeng.* 106:326-332, 2010) or pBTL vectors (Lynch et al., *Biotechnol. Bioeng.* 94:151-158, 2006). In one non-limiting example, the vector is based on vector pBTL-2 (Addgene plasmid #22806).

In some examples, the plasmid introduced is extrachromosomally and replicated within the host. In other examples, after introduction of the plasmid, a double homologous recombination event occurs and the one or more genes are inserted into the genome.

Transformation of a bacterial cell with recombinant DNA can be carried out by conventional techniques as are well known to those skilled in the art. Where the host is bacterial, such as, but not limited to, *P. putida*, competent cells which are capable of DNA uptake can be prepared from cells harvested after exponential growth phase and subsequently treated by the $CaCl_2$) method using procedures well known in the art. Alternatively, $MgCl_2$ or RbCl can be used. Bacteria can also be transformed by electroporation, conjugation, or transduction.

EXAMPLES

The following examples are provided to illustrate certain particular features and/or embodiments. These examples should not be construed to limit the disclosure to the particular features or embodiments described.

Example 1

Evolution of PCA Sensor in *Pseudomonas putida*

A plasmid construct was created using a broad host range vector, pBTL-2 (Addgene plasmid #22806), genetic sequences encoding the transcription factor based sensor, PcaU, and a reporter, superfolder GFP (sfGFP). The regulatory region from a previously constructed *E. coli*-specific sensor-reporter system (Jha et al., *Nucl. Acids Res.* 42:8150-8160, 2014) was incorporated between the sensor and reporter genetic sequences, and the whole cassette was assembled between two bidirectional transcriptional terminators using NEBuilder Hi-Fi assembly kit (New England Biolabs). The new plasmid construct, pPcaU1 (SEQ ID NO: 1) was transformed into *P. putida* and grown to a mid-log phase at 30° C. before induction with 10 mM or lower PCA, and further grown overnight at 30° C. Cell fluorescence measurements using flow cytometry (ex/em 488/530) failed to show any dose-dependent response.

Figures 2A, 2B:
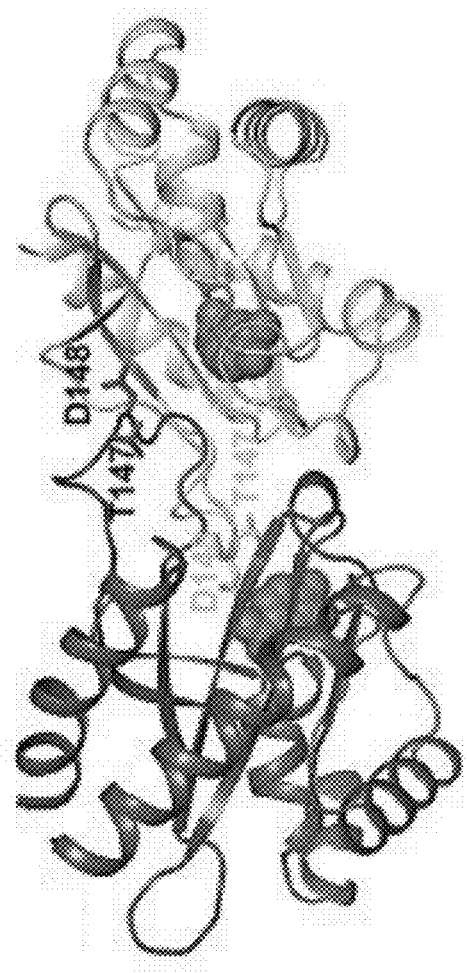
FIGS. 2A and 2B show an example for promoter and protein evolution in *P. putida*.

Four rounds of sorting using a FACSAria III flow cytometer (BD Biosciences) were performed, with one round of negative selection (bottom 50% population of culture grown in the absence of PCA or uninduced) to eliminate constitutively active variants after two rounds of sorting out the top 5% of induced population (grown in 10 mM PCA). The fourth round of sorting of top 1% population grown in 10 mM PCA, and subsequent plating and testing monoclonal isolates resulted in identification of a variant that showed a distinct response when dosed with 1 mM PCA. The isolated variant showed mutations in both −35 and −10 sites along with the intended deletion between the promoter and the operator (FIG. 2A). This version of sensor plasmid was named pPcaU1.1 (SEQ ID NO: 2).

Example 2

Further Evolution of PCA Sensor in *Pseudomonas putida*

Figure 5:
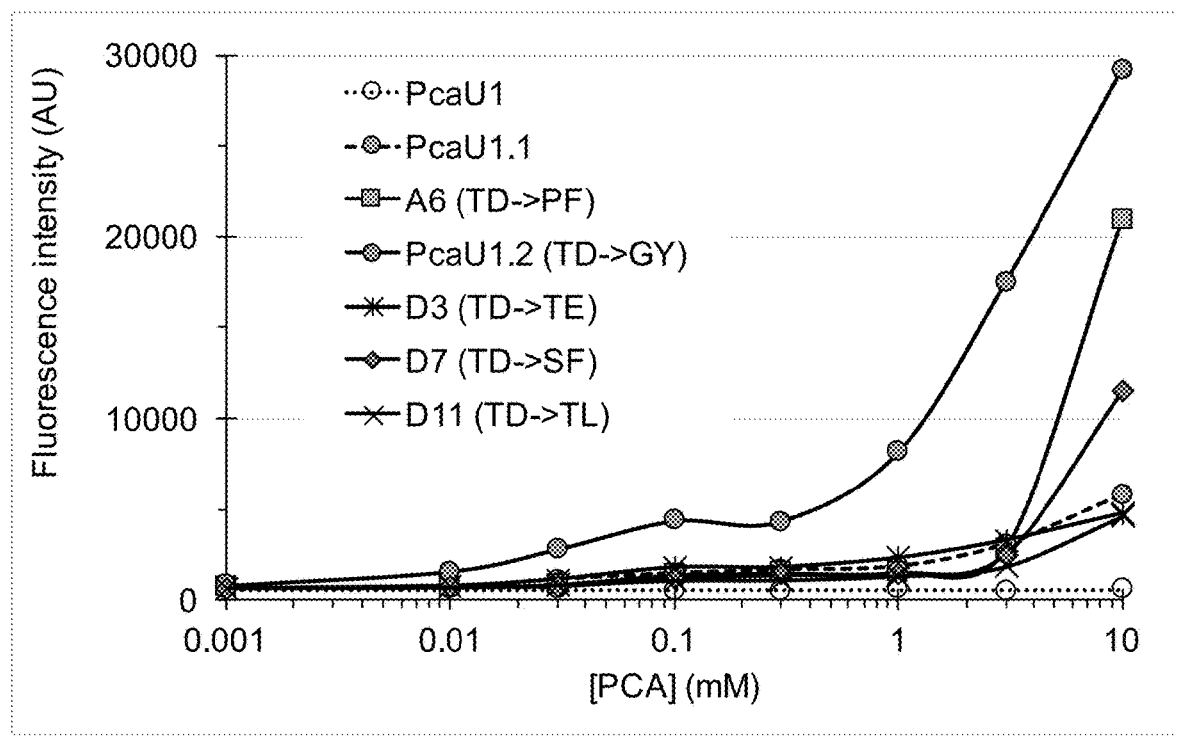
FIG. 5 is a graph showing PCA dose-response measured using flow cytometry with the indicated sensor plasmids. T147/D148 on PcaU dimer interface were mutated on PcaU1.1 sensor background. The legend shows the identified mutations in parentheses.

To achieve further enhancement of sensitivity and amplitude in a dose-response curve, saturation mutagenesis was carried out at the putative dimer interface as predicted from symmetric homology modeling (FIG. 2B) (Raman et al., *Proteins Struct. Funct. Bioinforma* 77:89-99, 2009; Jha et al., *Proteins Struct. Funct. Bioinforma* 83:1327-1340, 2015). Complete randomization of the PcaU sequence positions 147 and 148 using 'NNK' codons that code for all twenty amino acids and a stop codon, yielded a library with a theoretical diversity of approximately 440. *P. putida* strain CJ072 was transformed with the library and grown (uninduced) and sorted for the bottom 40% of the population to eliminate high background and constitutive variants. Subsequently, the sorted population was grown in 0.01-10 mM PCA, and the top 1% of the population was collected from the 0.01 mM induction based on fluorescence intensity. The second round of sorted populations yielded several monoclonal isolates that showed comparable dynamic range with the E. coli protocatechuate biosensor (Jha et al., Nucl. Acids Res. 42:8150-8160, 2014). The most sensitive and responsive variant with T147G/D148Y mutations was named pPcaU1.2 (SEQ ID NO: 3) and is able to detect exogenously supplemented PCA at concentrations below 0.003 mM and a contrast ratio [(Induced signal)/(Uninduced fluorescence signal)] of over twelve-fold (FIG. 3 and FIG. 4A). Other variants in the second round of sorting, for example T147S/D148F or T147P/D148F, showed reduced sensitivity but a sharp gain in signal beyond 1 mM exogenous PCA concentration (FIG. 5).

For specificity evaluation of the biosensor, PcaU1.2 was tested against molecules with similar functional groups, namely benzoate, 4-hydroxybenzoate (4HB), and catechol. The tested molecules were relatively smaller than PCA, to eliminate any rejection of the molecule from the binding pocket due to steric hindrance.

Low but measurable activation of the sensor was observed with benzoate and 4HB (FIG. 4B), while catechol showed a signal that was an appreciable fraction of PCA response (FIG. 4B).

In addition, the PcaU1.2 sensor was tested in a dynamic environment with different knockout strains of P. putida (FIG. 4C). Depending on the mutations in the strain, 4HB would either accumulate or be converted to PCA as an end product, or be further metabolized via the β-ketoadipate pathway (native P. putida KT2440) (FIG. 4C). The response to 4HB feeding in different strains harboring the sensor was consistent with the expected PCA level in the cell. The PcaU1.2 response was highest in CJ072 (due to PCA accumulation), followed by native (PCA metabolized into β-carboxymuconate) with the lowest response observed in CJ182 (where 4HB is not converted into PCA) (FIG. 4D).

Example 3

Alleviation of Enzyme Product Inhibition by Transcription Factor Based 4-Hydroxybenzoate Biosensor for Muconate Production Materials and Methods Growth medium, conditions, small molecules: Unless specified, all cultures of P. putida were grown in Lysogeny Broth (LB) medium and supplemented with 50 g/mL kanamycin (Kan$_{50}$) when necessary to maintain plasmids. LB agar plates were prepared with 1-1.5% agar. The cultures were grown in 14 mL round bottom culture tubes (BD falcon) in a volume of 3-5 mL at 30° C. with shaking at 225-250 rpm. 4-HB (Acros), benzoic acid (Fluka), and cis,cis-muconic acid (Acros) were prepared as sodium salts by dissolving in an equimolar amount of sodium hydroxide. Hence, the actual forms of 4HB, benzoate, and muconate will be interchangeably used for their respective acid forms.

Plasmids and strains: Tables 3 and 4 summarize the oligonucleotides, plasmids, and strains used in this study. P. putida KT2440 (ATCC #47054) derivatives were used for cloning, for whole cell biosensing, UbiC library preparation, and screening of various UbiC constructs. P. putida KT2440 and the engineered derivative CJ182 (Jha et al., Metab. Eng. Commun. 6:33-38, 2018) were used to test the 4HB biosensor construct. CJ182 was used for screening of the UbiC library. P. putida KT2440 derivative CJ200 (Johnson et al., Metab. Eng. Commun. 3:111-119, 2016) was used for the muconate production experiments. The DNA fragment encoding PobR-DM and the native promoter were PCR amplified from a previous E. coli adapted biosensor (Jha et al., Proteins Struct. Funct. Bioinforma 83:1327-1340, 2015) using oligonucleotides described in Table 4 that amplified products to include overlap with a broad host range vector backbone and the sfgfp gene that encodes the superfolder GFP (sfGFP) reporter. For the backbone, the pBTL-2 vector (Addgene plasmid #22806), was PCR amplified using the oligonucleotides pBTL-2_Rev and pBTL-2_Fwd (Table 4). The two PCR products along with sfgfp gene were assembled using NEBuilder HiFi Assembly kit (New England Biolabs) to create the pBTL-2_PobR-DM_sfGFP plasmid (pPobR; SEQ ID NO: 6). The E. coli ubiC gene was PCR amplified from genomic DNA of E. coli type B cells (ATCC strain #11303) using oligonucleotides ecUbiC_EcoR1_f and ecUbiC_Avr2_r (Table 4), and cloned into the pPobR plasmid between EcoRI and AvrII sites, such that the ubiC gene was in frame with the sfgfp gene. The mutation corresponding to the previously published L30A UbiC mutant (Han et al., ACS Catal. 6:8440-8445, 2016) was introduced by first creating two PCR fragments using oligonucleotides ecUbiC_EcoR1_f and ecUbiC_L30A_R and ecUbiC_F1 and ecUbiC_Avr2_r and the ubiC gene as the template and then assembling them with an overlap oligonucleotide method. The mutant gene was cloned into the pPobR as described above. C-terminal 6xHistag versions of the UbiC variants were created using PCR amplification of the gene with oligonucleotides ecUbiC_EcoR1_f and ecUbiC_GGlink_6His_Avr2_r (Table 4). The PCR products were cloned into pPobR in the same way as described earlier. The new gene cassettes encode N-terminal sfGFP-fused UbiC variants with a glycine-glycine linker followed by a 6xHistag in the C-terminus. The electrocompetent cells of P. putida were prepared and transformations were performed according to an established protocol (Choi et al., J. Microbiol. Methods 64:391-397, 2006). The pBTL-2 derived plasmids were transformed in P. putida strains using electroporation (BioRad) in a 1 mm cuvette at 1.6 kV, 25 µF and 200 ohms. A typical time constant of 4.7-5.1 ms was observed for a successful transformation. The transformed cells were selected on LB agar plates with Kan$_{50}$. A small scoop of cells (using 1 µL inoculation loop) from the transformation plates was grown overnight, mixed with glycerol at a final concentration of 20%, and stored in −80° C. as glycerol stocks.

Vector construction for genomic integration: The 5' and 3' homology arms flanking the intergenic region between the genes PP_1642 and PP_1643 were PCR amplified from CJ200 strain using KOD Hot Start polymerase (Millipore). The homology arms consisted of 1009 bp of PP_1642 and 947 bp of PP_1643. The pobR-DM_ubiC-C22 gene cassette was PCR amplified from the pPobR_ubiC-C22 plasmid. The homology arms and the pobR-DM_ubiC-C22 PCR product were Gibson assembled (Merryman and Gibson, Metab. Eng. 14:196-204, 2012) into the suicide integration vector pk18mobsacB (Johnson et al., Metab. Eng. 28:250-247, 2015; Marx, BMC Res. Notes 1:1, 2008; Schafer et al., Gene 145:69-73, 1994) using the NEBuilder HiFi Assembly kit (New England Biolabs). This created the pk18mobsacB_ubiC-C22 plasmid with the PobR regulated promoter driving ubic-C22 gene expression for genomic integration.

Genomic integration: Gene integration in the P. putida KT2440-derived strain CJ200 was accomplished by electroporation of the pk18mobsacB_ubiC-C22 plasmid as described above. Briefly, chromosomal integration by homologous recombination was selected on LB agar plates supplemented with 100 µg/mL kanamycin. Colonies were then counter-selected for a second cross-over event to remove the plasmid from the genome on YT (yeast extract+ tryptone) agar plates supplemented with 25% sucrose, as described previously. Insertion was confirmed by PCR amplification using primers (F_100up_1642_UbiC and R_100up_1642_UbiC) that bind outside of the homology regions used to target integration.

Table 3. Strains and plasmids

TABLE 3

Strains and plasmids

| | Description | Reference or Source |
|---|---|---|
| Strain | | |
| *Pseudomonas putida* KT2440 | *P. putida* ATCC # 47054 | ATCC |
| CJ182 | *P. putida* KT2440 ΔpobAR | Jha et al., *Metab. Eng. Commu.* 6:33-38, 2018 |
| CJ072 | *P. putida* KT2440 ΔpcaHG | Jha et al., *Metab. Eng. Commu.* 6:33-38, 2018 |
| CJ200 | *P. putida* KT2440 ΔcatRBC::Ptac:catA ΔpcaHG::Ptac:aroY:ecdB:asbF | Johnson et al., *Metab. Eng. Commun.* 3:111-119, 2016 |
| NP015 | *P. putida* KT2440 ΔcatRBCA::Ptac:catA ΔpcaHG::Ptac:aroY:ecdB:asbF::pobR-DM-UbiC-C22 | This study |
| CJ390 | *P. putida* KT2440 ΔpcaIJ::Ptac:asbF | NREL |
| CJ184 | *P. putida* KT2440 ΔcatRBC::Ptac:catA ΔpcaHG::Ptac:aroY:ecdB:ecdD | Vardon et al., *Energy Env Sc*, 8:617-628, 2015 |
| NN7 | *P. putida* KT2440 ΔpykA::Ptac:aroGD146N:asbF ΔpykF Δppc Δpgi-1 Δpgi-2 ΔpcaIJ ΔpcaR (or SN04 ΔpcaR) | This study (SN04 received from NREL) |
| JW0451 | *E. coli* K12 F-, Δ(araD-araB)567, ΔlacZ4787(::rrnB-3), ΔacrB747::kan, λ⁻, rph-1, Δ(rhaD-rhaB)568, hsdR514 | CGSC#8609; Baba et al., *Mol. Syst. Biol.* 2:2006.008, 2006 |
| Plasmid | | |
| pBTL-2 | Kanamycin resistance, pBR322 ori, Plac promoter between soxR and tonB terminators | Lynch and Gill, *Biotechnol. Bioeng.* 94:151-158, 2006 |
| pBTL-2_pobR-DM_sfGFP (pPobR) | pobR-DM, PobR promoter, sfgfp sequences cloned between soxR and tonB terminators | This study |
| pPobR_ubiC-wt | pPobR with *E. coli* ubiC gene cloned in frame with sfgfp using EcoR1/Avr2 sites | This study |
| pPobR_ubiC-L30A | pPobR with ubiC gene containing mutations encoding L30A | This study |
| pPobR_ubiC-C2 | pPobR with ubiC gene containing mutations encoding E31Q, T92A | This study |
| pPobR_ubiC-C11 | pPobR with ubiC gene containing mutations encoding E31Q, I78V, L80V | This study |
| pPobR_ubiC-C14 | pPobR with ubiC gene containing mutations encoding E31Q, I78V, T92A | This study |
| pPobR_ubiC-C21 | pPobR with ubiC gene containing mutations encoding M34V, I78V | This study |
| pPobR_ubiC-C22 | pPobR with ubiC gene containing mutations encoding E31Q, M34V | This study |

TABLE 4

Oligonucleotides

| Primer Name | Sequence | SEQ ID NO: |
|---|---|---|
| pBTL2_pobR_overlap_F1 | TGCTATGGAGGTCAGGTATGATTTTATACCAGATTGCGCAGTTCG | 33 |
| PobRpromo_sfGFP_overlap_R1 | GTTCTTCTCCTTTGCTAGCCATATGTATATCTCCTTGCTATTTTC | 34 |
| sfGFP_Fwd | ATGGCTAGCAAAGGAGAAGAAC | 35 |

TABLE 4-continued

Oligonucleotides

| Primer Name | Sequence | SEQ ID NO: |
| --- | --- | --- |
| pBTL-2_sfGFP_overlap_Rev | GAGGCTCGTCCTGAATGATATCTTACCTAGGTGTGAATTCAGAAC | 36 |
| pBTL-2_Fwd | GATATCATTCAGGACGAGCCTCAGACTCC | 37 |
| pBTL-2_Rev | AATCATACCTGACCTCCATAGCAGAAAGTCAAAAG | 38 |
| ecUbiC_EcoR1_f | AGTCGAATTCTCACACCCCGCGTTAACGCAAC | 39 |
| ecUbiC_Avr2_r | AGTCCCTAGGTTAGTACAACGGTGACGCCGG | 40 |
| ecUbiC_F1 | ACAAAACGTTTTGAACAGCAG | 41 |
| ecUbiC_31_34_R | CTGCTGTTCAAAACGTTTTGTCAYGGAATCCTSCAGCAACAGCCAGTCGAGCAG | 42 |
| ecUbiC_L30A_R | CTGCTGTTCAAAACGTTTTGTCATGGAATCCTCCGCCAACAGCCAGTCGAGCAG | 43 |
| ecUbiC_76_78_80_R | GCCACGGTTCACCATCGGCACATAMCAAAAYTTCCHTTAACCAGTAACGAGACTCTTTCG | 44 |
| ecUbiC_90_92_F | CCGATGGTGAACCGTGGCTTGCCRGTCGTRCCGTCGTTCCTGTGTCAACGTTA | 45 |
| ecUbiC_114_R | GATGTGAACAGATAGCGTCCTAMCGGCGTTTTACCCAATTTTTG | 46 |
| ecUbiC_F2 | GGACGCTATCTGTTCACATC | 47 |
| ecUbic_GGlink_6His_Avr2_r | AGTCCCTAGGTTAGTGATGGTGATGGTGATGGCCACCGTACAACGGTGACGCCGG | 48 |
| F_100up_1642_UbiC | GGCATCATCGCGACGACATCGTCGAAA | 49 |
| R_100up_1642_UbiC | TATCGAGCTGGCCGGCATGGAGGCG | 50 |

Whole cell biosensing of 4HB and benzoate: For 4HB sensing activity of the whole cell biosensor, a small scoop of pPobR transformed *P. putida* cells from a streaked plate or a glycerol stock was grown overnight as a seed culture. The overnight saturated seed culture was then diluted 100-fold in fresh growth medium, grown for 5-6 h at 30° C. to achieve an $OD_{600}$ of ~0.6, then distributed in deep 96-well blocks in a volume of 300-500 µL and induced with varying concentrations of 4HB or benzoate. The cultures were grown overnight (14-16 h) under vigorous shaking in a deep-well shaker (Taitec BioShakerM-BR-022UP). The cultures were diluted 100-fold in phosphate-buffered saline (PBS) with 1% sucrose and analyzed using an LSR II flow cytometer (BD Biosciences) or Accuri C6 flow cytometer (BD Biosciences) with standard settings for measurement of GFP fluorescence (ex 488 nm, em ~530/30 nm). The arithmetic mean fluorescence value of ~100,000 cells tightly gated based on forward and side scatter (FSC vs SSC) was used for a dose-response plot. Same protocol was followed for comparison of UbiC clones.

Selecting mutagenesis sites in UbiC and library creation: The UbiC crystal structure with a bound 4HB molecule (PDB code 1JD3) was used for the determination of appropriate sites for mutagenesis that could weaken the 4HB/UbiC interaction. Based on the first shell amino acids (4 Å radius from 4HB ligand atoms), seven positions were identified for mutagenesis in the binding pocket. A few positions on the loop referred to as the flap (Han et al., *ACS Catal.* 6:8440-8445, 2016) were also selected for mutagenesis. Mutations were selected such that only small changes in side chain properties (hydrophobic to hydrophobic, charged to polar, polar to hydrophobic or hydrophobic to polar) were achieved. The diversified library of ubiC was constructed using the oligonucleotides with wobble at appropriate positions and PCR amplification using *E. coli* genomic DNA containing the ubiC gene as a template. The fragments were created using forward and reverse primer pairs of ecUbiC_EcoR1_f and ecUbiC_31_34_R, ecUbiC_F1 and ecUbiC_76_78_80_R, ecUbiC_90_92_F and ecUbiC_114_R and finally ecUbiC_F2 and ecUbiC_Avr2_r with the wild-type ubiC gene as the template. The fragments were assembled using overlap extension PCR. Complete ubiC gene variants were double digested with restriction enzymes EcoRI/AvrII restriction endonucleases (NEB Biolabs) and cloned into the pPobR plasmid such that the ubiC gene was in the same reading frame as sfgfp. The gene library created consisted of zero to eight mutations in any gene, since all the mutations were represented in a small set of random clones as confirmed by Sanger sequencing. Transformation in *P. putida* strain CJ182 was carried out using the electroporation method as described above. Following transformation, total number of colonies on the plate representing approximately 40-fold the library diversity, were scraped and stored as glycerol stocks. Typical $OD_{600}$ of the glycerol stock was ~1. As needed, a scoop of glycerol stock using 1 µL inoculation loop was sequentially diluted twice in 1 mL LB to reach approximately $10^4$ cells/mL and 100-400 µL of the diluted sample spread on agar plates with suitable growth conditions to get a total of 1000 to 4000 well separated colonies on a 85 mm or 125 mm diameter petri dish, respectively.

Selection of UbiC variants with relieved product inhibition: To select clones with relieved product inhibition, *P. putida* cells containing variants of ubiC were grown on LB agar plates containing high concentrations (3 mM and 10 mM) of benzoate. Benzoate works as a proxy for 4HB because the two molecules are aromatic and carry similar charge. Benzoate is capable of inhibiting the enzyme UbiC with a $K_p$ thousand-fold higher than 4HB (Holden et al., *Biochim. Biophys. Acta BBA-Protein Struct. Mol. Enzymol.* 1594:160-167, 2002), but does not activate the 4HB biosensor at those concentrations (this work). Colonies were selected visually based on the intensity of their fluorescence under an illuminator (excitation wavelength 488 nm, emission filter 515 nm). Selected colonies were grown and stored as glycerol stocks for later use. The clones were compared in liquid cultures as described above.

Enzyme expression and purification: 5 mL cultures were grown from the glycerol stocks of *P. putida* CJ182 containing plasmids encoding 6×His-tag UbiC variants. At an $OD_{600}$ of ~0.6, the cultures were induced with 1 mM 4HB and further grown for 16 h at 30° C. and 225 rpm shaking. The cultures were centrifuged at 3500×g for 10 min and the cell pellets were lysed with 500 µL BugBuster (Novagen) under slow shaking for 30 min. The cell lysates were centrifuged at 15,000×g for 15 min at 4° C. and the sfGFP-UbiC fusion proteins were purified by Affinity Chromatography using Talon beads (Clontech). For purification, the clarified supernatant for each UbiC variant was mixed with 200 µL Talon beads in an equilibration buffer (50 mM Tris-HCl, 300 mM NaCl, pH 7.5) for 30 min. The mixture was centrifuged at 2000×g, the supernatant was discarded and the pellet consisting of Talon beads with bound protein was washed two times with equilibration buffer containing 50 mM imidazole. Finally, the beads were mixed with elution buffer (50 mM Tris-HCl, 300 mM NaCl, 300 mM Imidazole, pH 7.5) and filtered through a spin column with 0.2 m filter. The enzyme concentration and purity of the protein in the eluate were determined by absorbance at 280 nm using a Nanodrop (Thermo Scientific) and SDS polyacrylamide gel electrophoresis, respectively.

Determining enzyme kinetic parameters: The production of 4HB from chorismate catalyzed by UbiC is accompanied with release of a pyruvate molecule. Hence, this activity of the purified UbiC proteins was monitored in vitro by a second reaction of NADH oxidation at 340 nm during conversion of pyruvate to lactate in a reaction mixture containing 0.5 units of lactate dehydrogenase (Sigma Aldrich) and 200 µM NADH (Sigma Aldrich) dissolved in 50 mM Tris-HCl buffer (pH 7.5), 0.5 µg of purified UbiC variants, chorismic acid (Sigma Aldrich) (30-300 µM), and 4HB (0-200 µM) in a final volume of 100 µL. The reactions were conducted in 96-well plate at 30° C. in the Synergy H4 Hybrid Microplate Reader (Biotek). The kinetic parameters and product inhibition constants were determined by measuring the initial reaction rates with respect to varying substrate and product concentrations and calculated using GraphPad Prism software.

Shake flask experiments for muconate production: *P. putida* CJ200 transformed with pPobR_ubiC plasmids or with genomically integrated ubiC-C22 under PobR regulation (NP015) were grown in 125 mL baffled shake flasks containing 25 mL of 1×M9 salts (6.78 g/L $Na_2HPO_4$, 3 g/L $KH_2PO4$, 0.5 g/L NaCl, 1 g/L $NH_4Cl$), 30-50 mM glucose, 2 mM $MgSO_4$, 100 µM $CaCl_2$), 18 µM $FeSO_4$, and 50 µg/mL kanamycin. Seed cultures were grown from glycerol stocks in LB media supplemented with 50 µg/mL kanamycin, for 16 hours, pelleted and washed with M9 growth medium and subcultured into flasks to a final $OD_{600}$ of 0.05. Cultures were incubated at 30° C. and 225 rpm for up to 2 days. Samples were taken at regular intervals to quantify cell density, glucose consumption, and muconate concentration.

Quantification of glucose and muconate concentrations using High Performance Liquid Chromatography (HPLC): To measure muconate concentration, culture samples collected at various time points were centrifuged either at 3,500 rpm for 10 min or 16,000 rpm for 1 min. The supernatants were transferred to a 0.22 µm spin column (Corning Costar Spin-X with cellulose acetate membrane), centrifuged, and the filtrates were transferred to HPLC vials for analysis by Agilent 1100 series HPLC system. The samples were analyzed for 10 min on a Fast Acid column (Phenomenex Rezex RFQ-Fast Acid H+(8%)) using 0.01 N $H_2SO_4$ at a flow rate of 0.8 mL/min as a mobile phase. A Diode Array Detector (DAD) set at 258 nm wavelength for detection was used for estimating muconate concentration. Alternatively, the samples were analyzed for 40 min on a SUPELCOGEL H Column (SUPELCO) with 0.1% $H_2SO_4$ at 0.5 mL/min. The temperature of both column and RID detector were maintained at 45° C. Glucose and muconate were quantified using a Refractive Index Detector (RID) and peaks were integrated using Agilent Chemstation software. Appropriate standards were made using commercial glucose and muconate samples.

Results

Figure 7A:
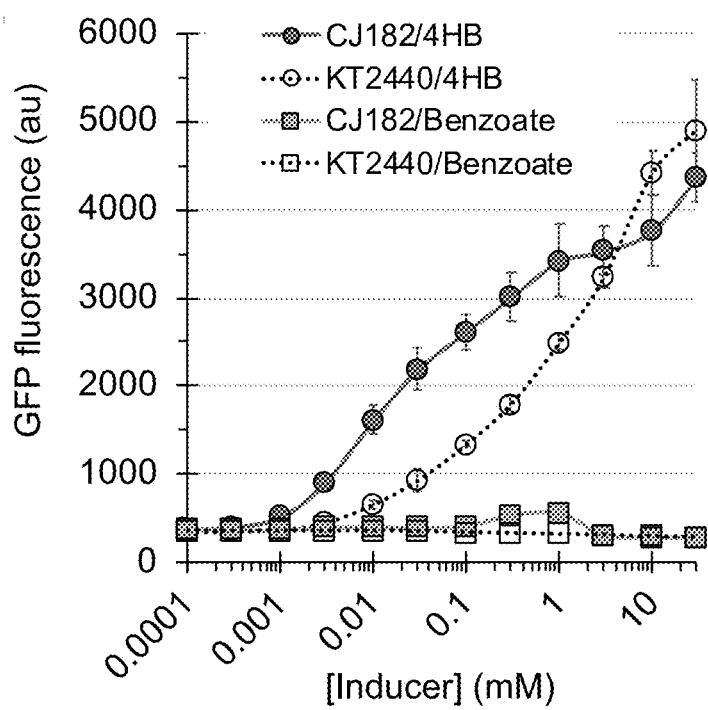
FIGS. 7A and 7B show *P. putida* transformed with pPobR (Sensor) or pPobR_ubiC (Sensor+Enzyme).

Double mutant of *Acinetobacter baylyi* ADP1 PobR and activity in *Pseudomonas putida* KT2440 for 4HB biosensing: PobR-DM is a double mutant (ΔL141, L220V) of the *Acinetobacter baylyi* ADP1 PobR transcription factor. When paired with the native promoter, the transcription factor exhibits very high sensitivity to 4HB in *E. coli* (Jha et al., *Proteins Struct. Funct. Bioinforma* 83:1327-1340, 2015; Jha et al., *Nucleic Acids Res.* 44:8490-8500, 2016). In *E. coli*, the sensor does not respond to closely related molecules like p-nitrophenol and very weakly responds to protocatechuate, but only at 1000-fold greater concentration than the native inducer, 4HB. The genetic fragment encoding PobR-DM and its promoter, along with the sfgfp (coding for superfolder GFP) reporter, were cloned into pBTL-2, a broad host vector. The resulting sensor plasmid, pPobR, was transformed into the *P. putida* strains KT2440 and CJ182, a strain incapable of metabolizing 4HB due to deletion of the native pobA. The whole cell biosensor responded in a dose-dependent manner to 4HB, showed high sensitivity (<3 µM exogenous 4HB in CJ182 and <30 µM in wild-type KT2440), and had a contrast ratio of >12-fold at 30 mM inducer concentration. In the absence of PobA activity in CJ182, the sensor would always see higher inducer concentration inside the cell compared to the native strain, resulting in the observed difference in sensitivity. Importantly, the whole cell biosensor did not show any response to benzoate, a molecule similar to 4HB but lacking the hydroxyl group (FIG. 7A). These data confirmed that the 4HB sensor is functional, sensitive, and specific for detection of 4HB in *P. putida*.

Figure 6A:
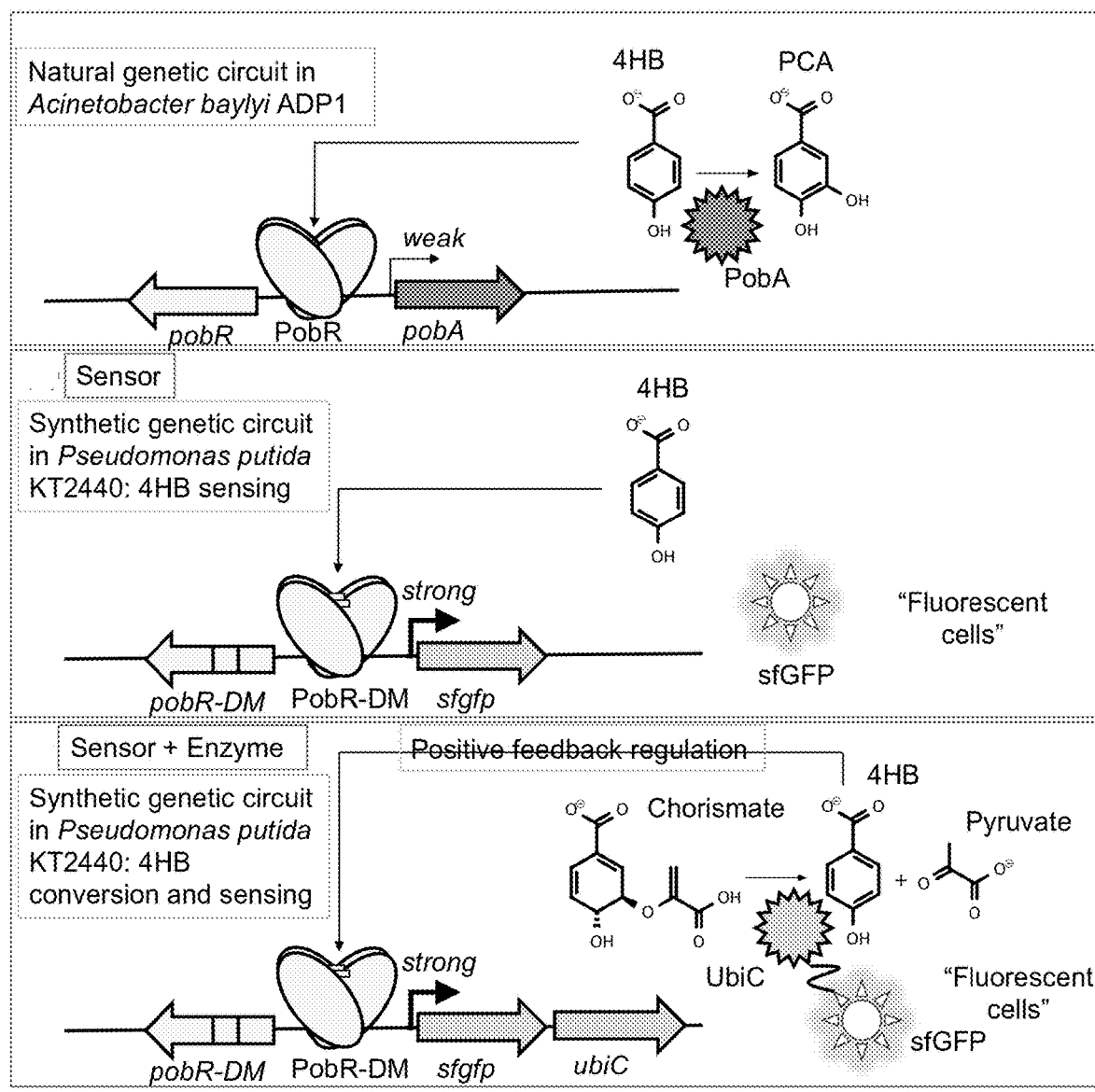
FIGS. 6A-6C are schematic diagrams showing natural and synthetic genetic circuits involving the PobR transcription factor (TF).
Figure 6C:
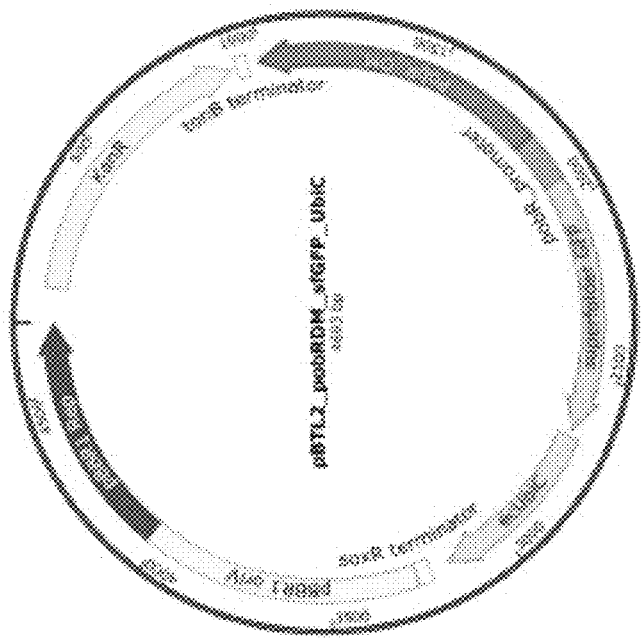
Figure 6B:
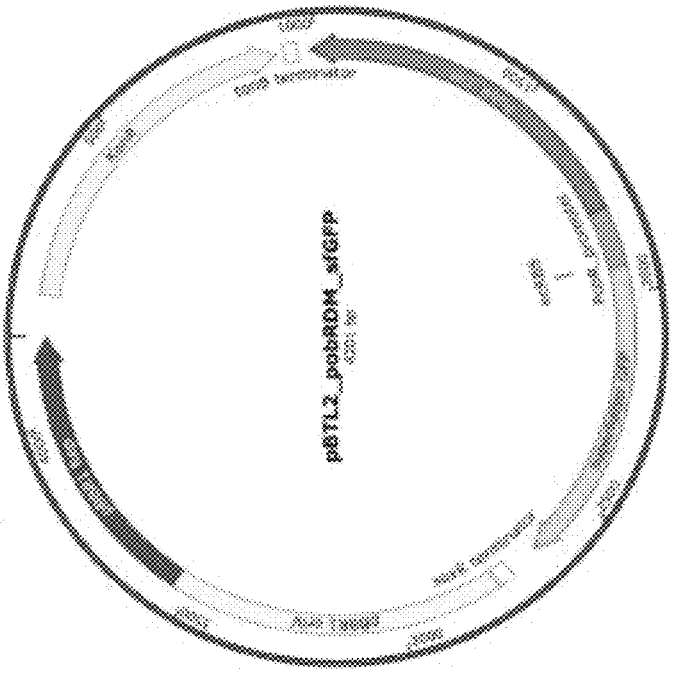
Figure 7B:
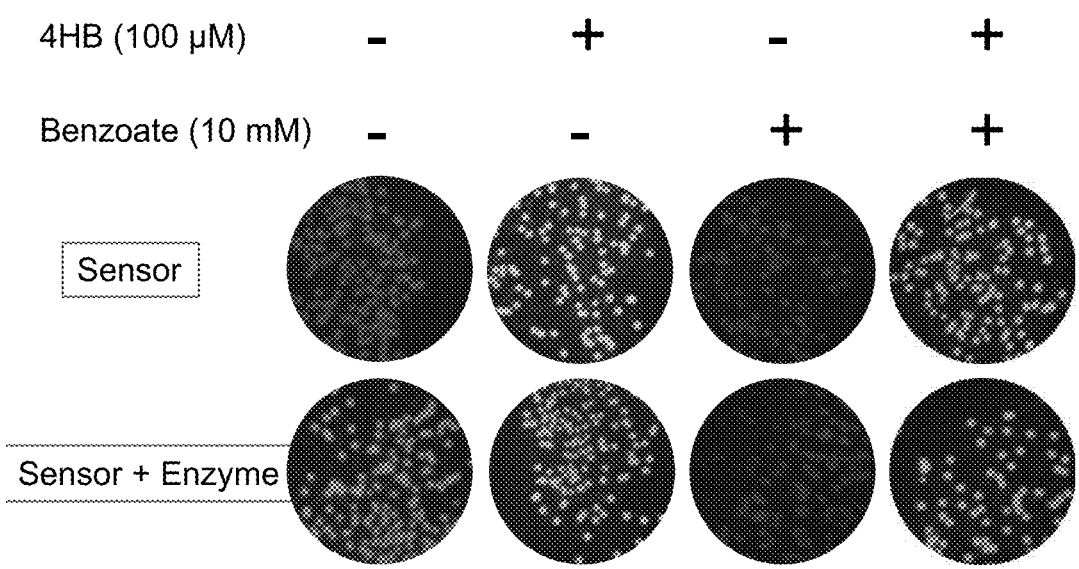
Figure 8A:
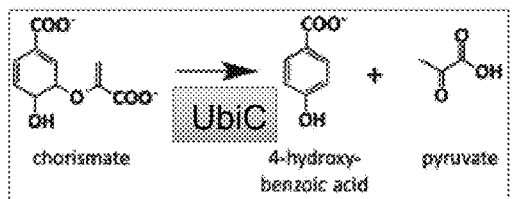
FIGS. 8A-8D are a series of panels related to improvement of an industrially relevant enzyme.
Figure 8B:
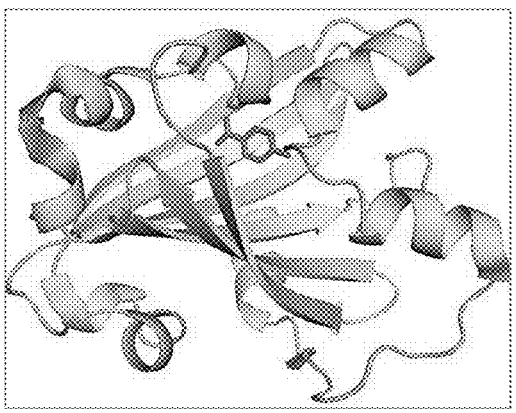
Figure 8C:
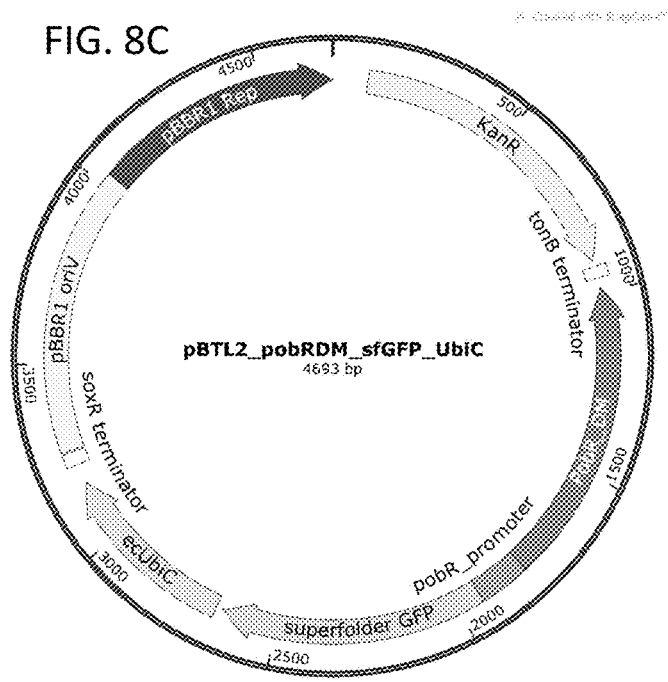
Figure 8D:
Figure 9:
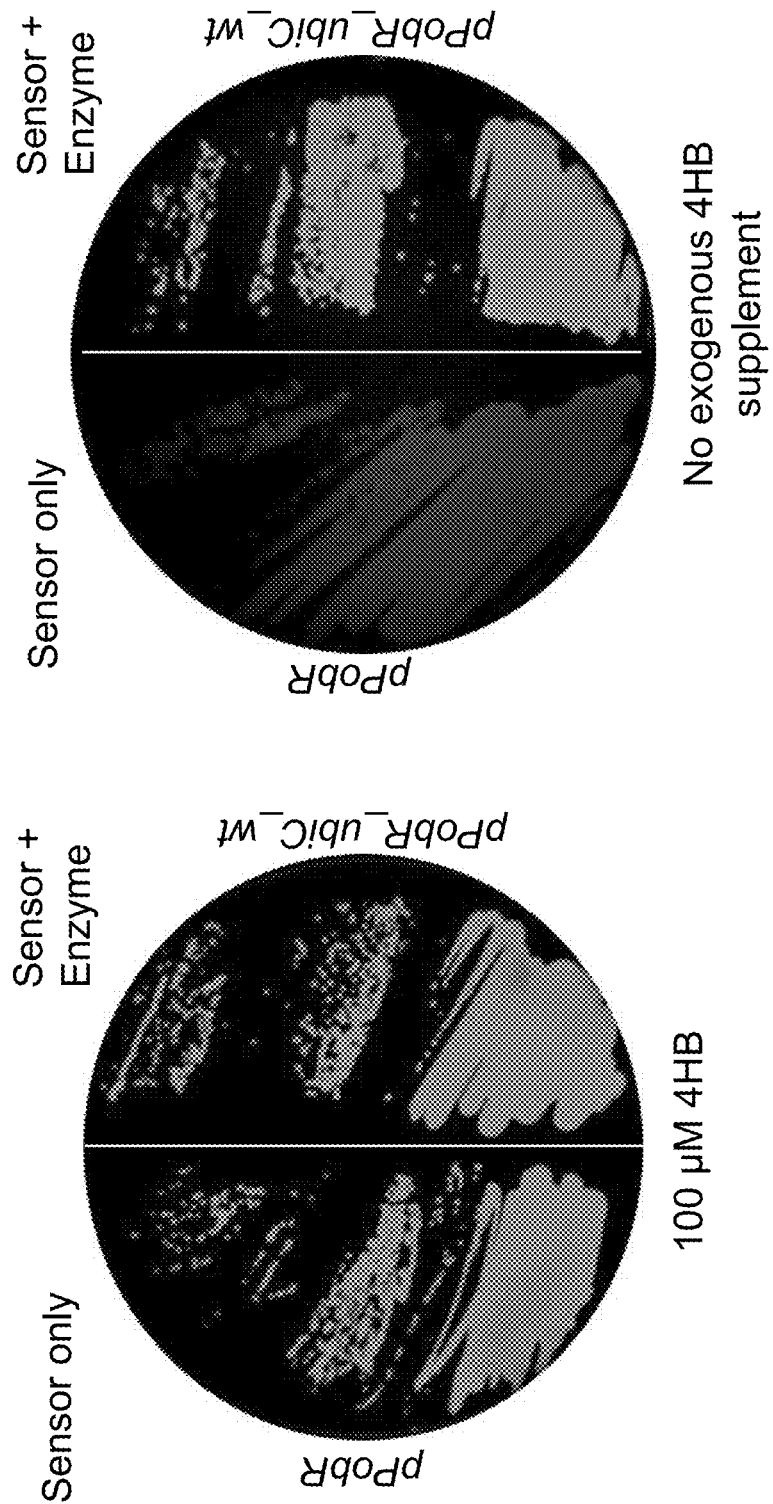
FIG. 9 shows *P. putida* strain CJ182 (ΔpobAR) transformed with PobR-DM-based sensor plasmid (pPobR) and plasmid with sensor with wild-type *E. coli* UbiC expression (pPobR_ubiC_wt) plated in the presence (left) and absence (right) of exogenous 4HB. In the absence of any exogenous 4HB, only Sensor+Enzyme carrying cells showed fluorescence, confirming formation and accumulation of 4HB inside the cells.

Intracellular 4HB production and sensing: The *E. coli* gene that encodes for UbiC was introduced into the pPobR sensor plasmid and in the same reading frame as the sfgfp reporter. In this positive feedback regulation set up, the enzymatic activity of UbiC regulated its own expression as a sfGFP fusion protein: specifically, higher UbiC activity should lead to more 4HB, which in turn increases activation of the sensor, which then leads to an increase in the expression of that ubiC gene (FIG. 6A). *P. putida* CJ182 cells showed high fluorescence colonies in the absence of exogenously supplemented 4HB only when harboring the sensor+enzyme construct pPobR_ubiC-wt (SEQ ID NO: 29), confirming that the expression of UbiC resulted in intracellular formation of 4HB, which, in turn, activated the PobR-DM sensor (FIG. 9). The plasmid containing the sensor alone (pPobR) showed dim colonies in the absence of exogenous 4HB (FIGS. 7B and 9), presumably from low background activity of the native UbiC in *P. putida* KT2440. When the growth media was supplemented with 10 mM benzoate, an inhibitor of UbiC with $K_i>3$ mM (Holden et al., *Biochim. Biophys. Acta BBA-Protein Struct. Mol. Enzymol.* 1594:160-167, 2002), the colonies showed diminished fluorescence, confirming inhibition of the UbiC enzyme and reduced production of the 4HB. Finally, when 100-fold less (100 µM) 4HB was supplemented with 10 mM benzoate, the colonies showed fluorescence. Together these data indicate that benzoate can inhibit enzyme activity but does not block the inducer binding pocket of the sensor (FIG. 7B).

Figure 10A:
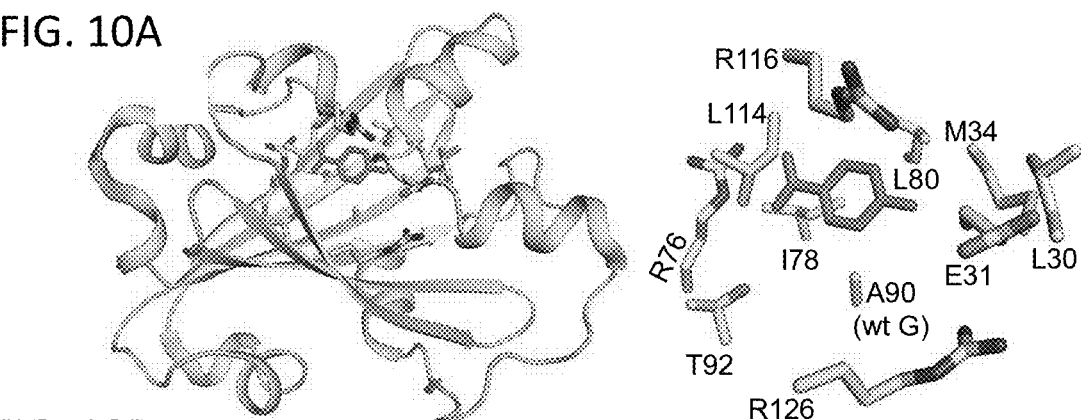
FIGS. 10A-10C show UbiC library and screening.

Mutational library of UbiC to reduce product inhibition: Based on the product-bound UbiC structure (PDB Code 1JD3), the amino acid positions that could be mutated to weaken the product binding were determined (FIG. 10A). We employed a conservative approach to select residue positions for mutagenesis, since an earlier study showed that even a single mutation in the enzyme was frequently detrimental to its stability (Han et al., *ACS Catal.* 6:8440-8445, 2016). It was also shown in the same study that mutations in the loop (L29 to M34, referred as the flap) can perturb the product binding to the enzyme. Two mutations L30A and D32A (numbering based on the UbiC structure PDB code: 1JD3), were expected to weaken hydrophobic and polar interactions respectively with the rigid portions of the protein. While the two mutations independently reduced product inhibition, combining them failed to show an additive effect in terms of gain-of-functions, probably due to poor stability and low expression of the double mutant protein (Han et al., *ACS Catal.* 6:8440-8445, 2016). We built upon this study, and took a two-pronged approach, where, in one case, mutations were further explored in the L29-M34 loop and, in another case, mutations specifically around 4HB were pursued such that product-enzyme interactions are weakened (FIG. 10A). For the first set of mutations, we chose to investigate E31Q and M34V mutations within the loop. E31, a negatively charged amino acid, exhibits a charge interaction with R116 and R126. We hypothesized that a conservative mutation of E31→Q would mitigate that interaction, resulting in an effect similar to the D32A mutation on the same loop that weakens the charge-charge interaction between D32 and R116 (Han et al., *ACS Catal.* 6:8440-8445, 2016). Similarly, the effect of the L30A mutation to create a void between position 30 and M34 can be recapitulated by shortening the side chain at position 34 by mutating it to valine. The other set of mutations focused around the product 4HB in the crystal structure. The R764→K/M mutations were selected to weaken/disrupt the existing electrostatic interaction between the carboxylate group of 4HB and the arginine at position 76 of the protein. Mutations I78→V, L80→V, T92→A and L114→V were also selected for diversification of UbiC, as these mutations are 'neutral drift' mutations and can weaken the 4HB/protein interaction due to shortening of the side chain in each case (FIG. 10A). The G90A mutation, as in the product bound structure of UbiC (PDB code 1JD3), is expected to increase the affinity of the 4HB/protein interaction. Hence, we chose the G90→S mutation since introduction of a hydroxyl group in close proximity of the 4HB aromatic ring was expected to weaken the interaction in addition to causing steric hindrance to 4HB due to a larger side chain. A combinatorial library consisting of the wild-type amino acid and selected conservative mutations at these eight positions in UbiC was created with a theoretical diversity of ~400, transformed into the *P. putida* strain CJ182, and plated. Transformed colonies (40-fold the library diversity) were scraped and evaluated in subsequent experiments.

Figure 10B:
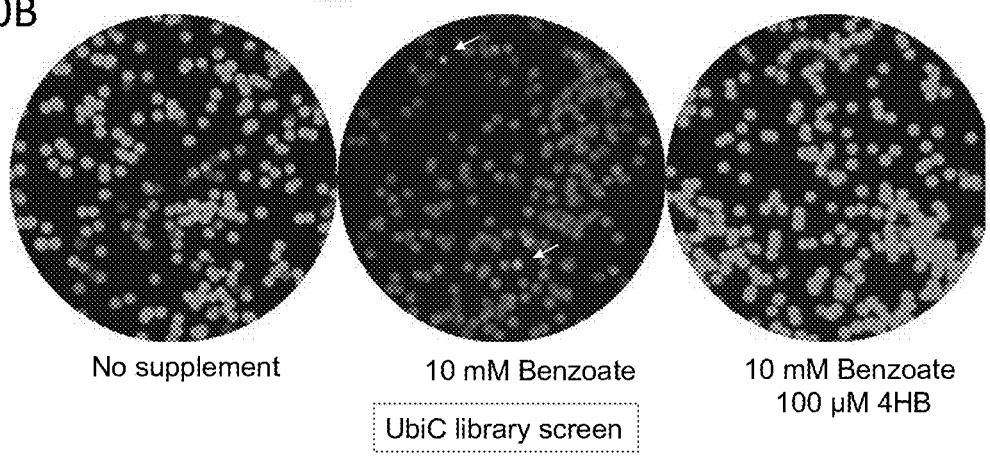
Figure 10C:
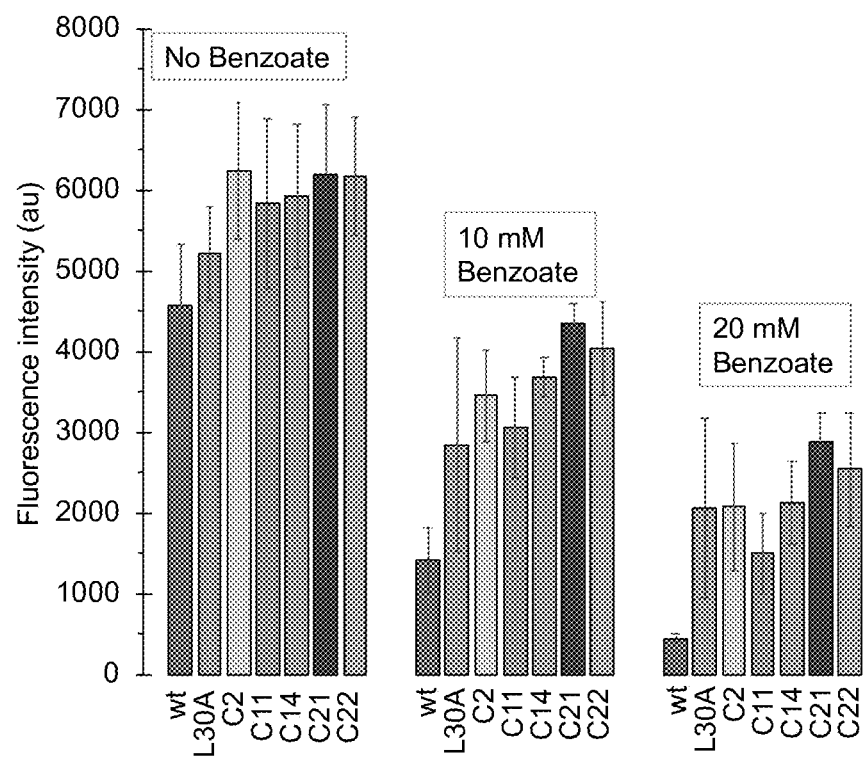

Benzoate as a surrogate molecule for high throughput screening of UbiC library using the 4HB sensor: The PobR-based sensor is specific to 4HB, and benzoate fails to activate the sensor. However, UbiC is sensitive to product inhibition from both 4HB (its product) and benzoate (with an affinity 1000-fold weaker than 4HB) (Holden et al., *Biochim. Biophys. Acta BBA-Protein Struct. Mol. Enzymol.* 1594:160-167, 2002). These observations were leveraged to relieve the product inhibition of UbiC, where UbiC variants with high activity were selected based on high fluorescence in the presence of the benzoate inhibitor. For selection, a CJ182-based UbiC library was plated in the presence and absence of 10 mM benzoate (FIG. 10B). In the absence of any inhibitor (benzoate) or inducer (4HB), the library showed varying fluorescence in the colonies, indicating that the variants were producing 4HB in vivo at different levels and inducing the biosensor to express sfGFP in a correlated fashion (FIG. 10B, left). When the library was cultured on 10 mM benzoate with 100 µM 4HB inducer, all of the colonies uniformly accumulated fluorescence (FIG. 10B, right), indicating again that the sensor activity is unaffected by the addition of benzoate, as observed above for the wild type UbiC+sensor strain (FIG. 7B). In the presence of 10 mM benzoate inhibitor alone, a small number of colonies were distinctly brighter than the rest, indicating that these colonies were able to make 4HB even in the presence of a high concentration of the benzoate inhibitor (FIG. 10B, middle). However, some of the brightest colonies were in a crowded region of the plate. These most crowded regions could have exhibited higher UbiC activity simply because the local benzoate concentration was reduced due to utilization by *P. putida*, which can metabolize it. Thus, bright colonies from such regions on the plate were not picked. Instead, several isolated colonies exhibiting fluorescence above the background from the benzoate-inhibited population were picked and evaluated in liquid culture supplemented with varying concentrations of benzoate. Five mutants of UbiC were identified that exhibited high retention of fluorescence (30-40%) even at 20 mM benzoate (FIG. 10C) while the wild-type exhibited very low fluorescence in the cells. The previously published UbiC variant with reduced product inhibition (UbiC-L30A) also showed high retention of cell fluorescence at 20 mM benzoate. Sequencing of the top clones revealed the following mutations: C2: E31Q/T92A; C11: E31Q/I78V/L80V; C14: E31Q/I78V/T92A; C21: M34V/I78V; C22: E31Q/M34V.

Kinetic analysis of the UbiC variants: As sfGFP fusions, expression and yields of the UbiC mutants from single step affinity purification were comparable with each other. We performed an in vitro kinetic assessment on a few UbiC variants to understand the mutational effects on the enzymatic properties. As a control for a variant with relieved product inhibition, the previously studied variant UbiC-L30A was also included in the study. Their kinetic parameters, $K_m$, $k_{cat}$ and $K_p$, were determined (Table 5). The variants, UbiC-C21 and UbiC-C22 showed a 3-5-fold increase in $K_m$ for chorismate along with 7-8-fold increase in product inhibition constant, $K_p$, confirming that the new variants of UbiC have alleviated product inhibition. The catalytic turnover number, represented by $k_{cat}$, showed an increase by 2-3-fold in UbiC-C21 and UbiC-C22 compared to the wild type. Catalytic efficiency ($k_{cat}/K_m$) of the mutant UbiC variants showed a marginal drop from the wild-type UbiC.

Table 5. Kinetic parameters of sfGFP fused UbiC variants with a C-terminal 6×His tag

TABLE 5

Kinetic parameters of sfGFP fused UbiC variants with a C-terminal 6xHis tag

| UbiC | Mutation(s) | $K_m$ (μM) | $k_{cat}$ ($s^{-1}$) | $k_{cat}/K_m$ ($s^{-1}M^{-1}$) | $K_p$ (μM) |
|---|---|---|---|---|---|
| Wild Type | None | 32.9 ± 2.8 | 0.37 ± 0.04 | $1.1 \times 10^4$ | 2.4 ± 0.2 |
| UbiC-L30A | L30A | 74.1 ± 8.7 | 0.64 ± 0.07 | $8.6 \times 10^3$ | 13.2 ± 1.0 |
| UbiC_C11 | E31Q/I78V/L80V | 54.7 ± 3.4 | 0.51 ± 0.04 | $9.3 \times 10^3$ | 4.7 ± 0.6 |
| UbiC_C21 | M34V/I78V | 90.2 ± 7.8 | 0.67 ± 0.06 | $7.4 \times 10^3$ | 17.8 ± 1.4 |
| UbiC_C22 | E31Q/M34V | 147.7 ± 9.4 | 1.04 ± 0.09 | $7.0 \times 10^3$ | 19.3 ± 2.5 |

Figure 11A:
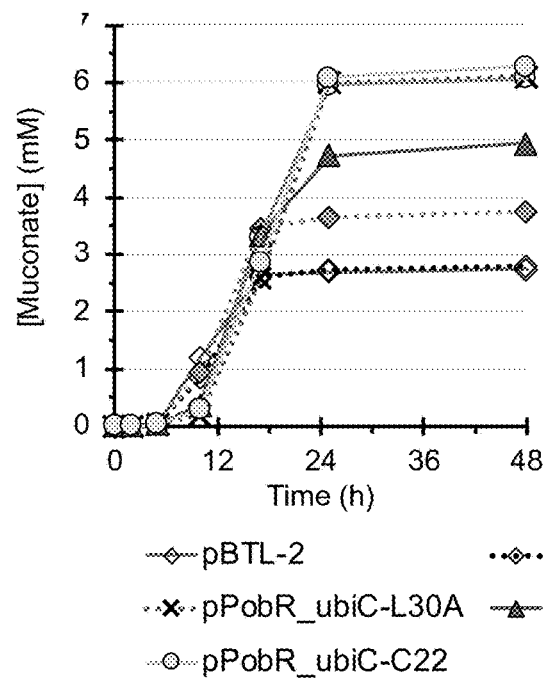
FIGS. 11A-11C show muconate production and growth for CJ200 *P. putida* strain transformed with pBTL-2 derived plasmids, containing genetic information for the sensor (PobR-DM) and different variants of UbiC enzyme.
Figure 11B:
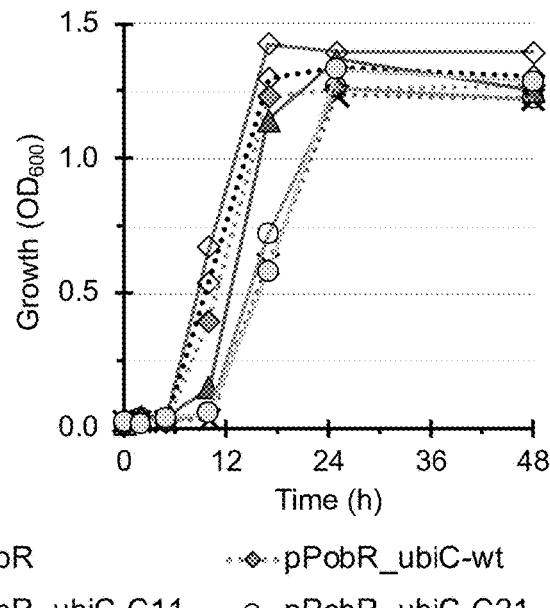
Figure 11C:
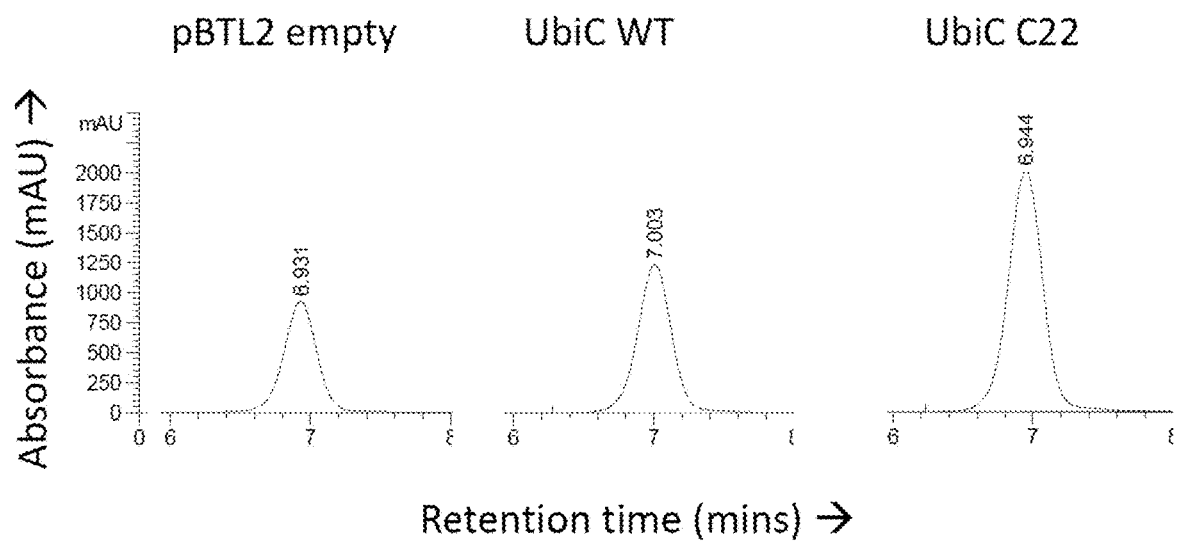

UbiC as a metabolic shunt for cis,cis-muconic acid production in *P. putida*: We next investigated if the UbiC mutants with reduced product inhibition can be applied to enhance the metabolic pathways for biosynthesis of valuable products. To test this, we chose cis,cis-muconic acid (muconate) as an end-product as it can be derived from 4HB via the shikimate pathway. We transformed the biosensor/enzyme plasmid with UbiC variants into the *P. putida* strain CJ200, which has been previously engineered to produce muconate (Johnson et al., *Metab. Eng. Commun.* 3:111-119, 2016). In *P. putida* KT2440, the introduction of the heterologous genes for the DHS dehydratase and protocatechuate (PCA) decarboxylase enables the conversion of dehydroshikimate (DHS) from the shikimate pathway to catechol via PCA. The native catechol-1,2-dioxygenase in the β-ketoadipate pathway converts catechol into muconate. Deletion of the downstream genes catBC and the regulator encoded by catR prevents further metabolism of muconate in the culture. With the introduction of the *E. coli* ubiC gene in CJ200, we introduced a pathway in which UbiC converts chorismite to 4HB, which is then converted to protocatechuate via the native PobA for subsequent conversion to muconate. We hypothesized that this additional route from the shikimate pathway to muconate might increase the overall flux to this target molecule. Earlier studies showed that in a batch culture with 50 mM glucose as a carbon source, CJ200 produced approximately 2.5 mM of muconate giving a molar yield ([muconate]/[glucose]) of 5% (Johnson et al., *Metab. Eng. Commun.* 3:111-119, 2016). CJ200 transformed with the pBTL-2 empty vector or the pPobR plasmid (sensor plasmid) and grown in the presence of Kanamycin (50 μg/mL) exhibited a similar yield of ~5.5% (FIG. 11B), indicating that kanamycin and/or presence of sfgfp gene do not add to any stress or metabolic burden to *P. putida* cells. With the introduction of the wild-type ubiC gene using the pPobR_ubiC-wt plasmid expressing sfGFP-fused UbiC under positive feedback regulation, the muconate yield increased by >30%, giving a final muconate concentration of 3.7 mM (FIG. 11A). Moreover, plasmids expressing variants of UbiC with alleviated product inhibition, UbiC-L30A, UbiC-C21, and UbiC-C22, exhibited a final muconate concentration of >6 mM and a yield increase of ~130% over CJ200 with no heterologous UbiC expression (FIGS. 11B and 11C). At 50 mM starting glucose concentration, the UbiC expressing CJ200 *P. putida* strains showed a longer lag phase during growth, which may be attributed to the metabolic burden caused by the production of higher amount of muconate from the essential shikimate pathway (FIG. 11B).

Figure 12A:
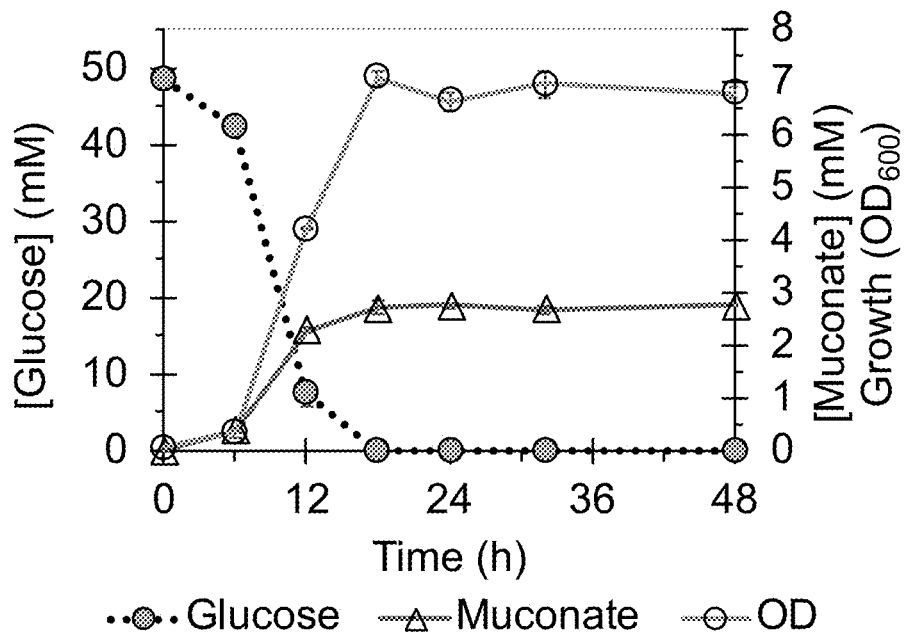
FIGS. 12A and 12B show muconate production in ubiC integrated *P. putida* strain CJ200. Growth curve, glucose depletion, and muconate production at 50 mM glucose in CJ200 (FIG. 12A) and NP015 (FIG. 12B) where the ubiC-C22 gene was integrated into the *P. putida* genome. Error bars are standard deviation from triplicate shake flasks.
Figure 12B:
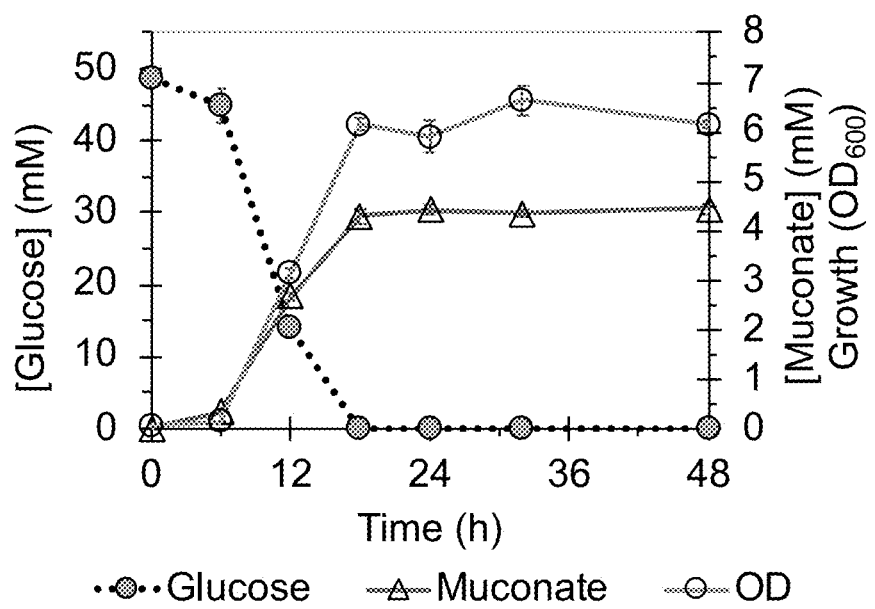

Genomic integration of evolved *E. coli* ubiC gene in *P. putida*: We further investigated the effect of the E31Q/M34V double mutant of UbiC-C22 in the muconate production strain, where the mutant ubiC gene was integrated into the genome of *P. putida* CJ200 strain. Simulating the plasmid version of ubiC-C22 in CJ200, we kept the expression of the UbiC under the positive feedback regulation of PobR and integrated it into the intergenic region between PP_1642 and PP_1643 to create strain NP015. At 50 mM glucose in a shake flask, CJ200 and NP015 were compared for growth, glucose consumption rates, and muconate production. While the two strains showed comparable rates for glucose consumption and growth, with complete glucose utilization and saturation cell density reached in 18 h, an enhancement in muconate production was observed in NP015 over the parent strain CJ200 (FIGS. 12A and 12B). At 18 h, muconate concentration in the culture media saturated. Muconate concentrations of 2.7 mM and 4.3 mM were observed in CJ200 and NP015 strains, giving a molar yield of 5.4% and 8.6%, respectively. This gave a yield improvement of 60% in the muconate production strain due to the addition of new carbon flux directed from shikimate pathway towards the heterologous muconate pathway (FIGS. 12A and 12B). A small difference in the final OD of the two strains can be attributed to the difference in muconate yields.

Example 4

PobA Activity and Library Screening

Figure 13B:
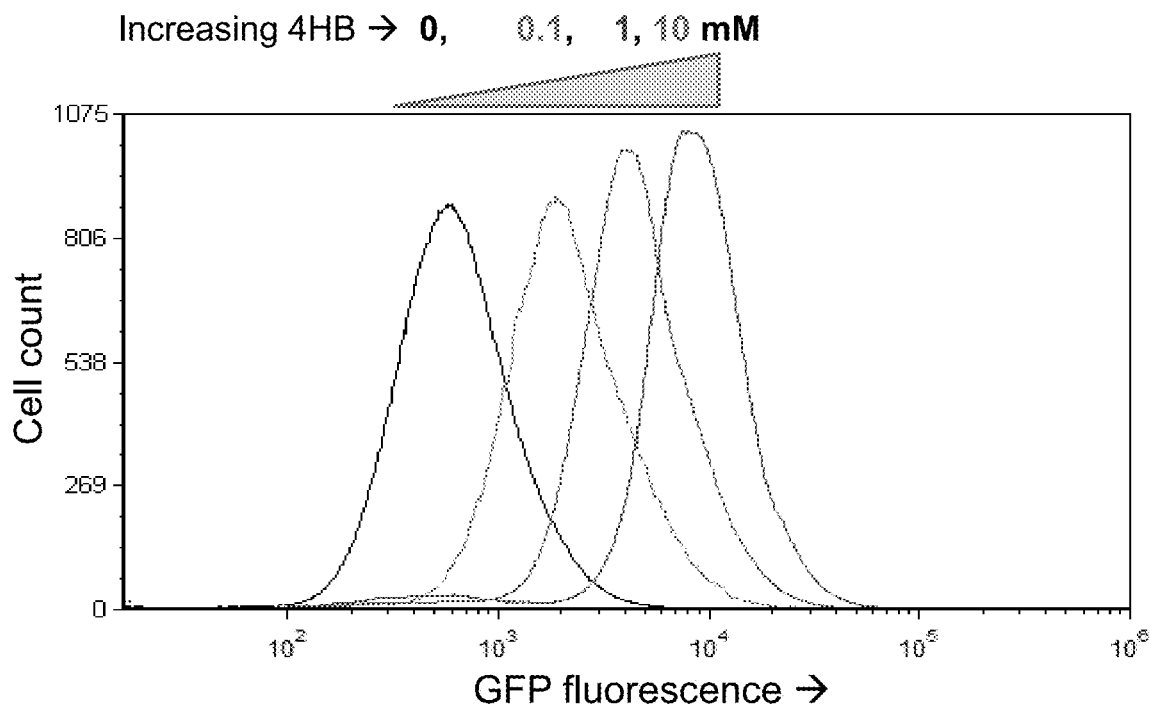
Figure 13C:
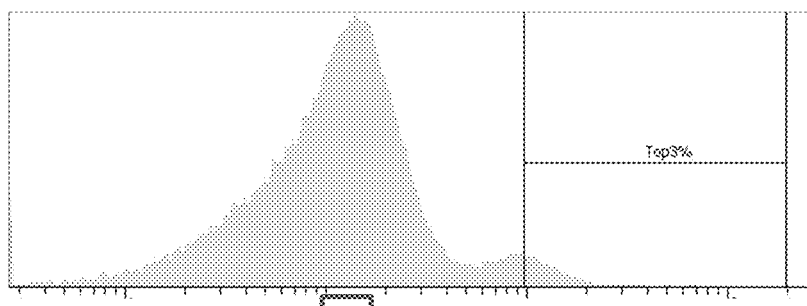
Figure 13C:
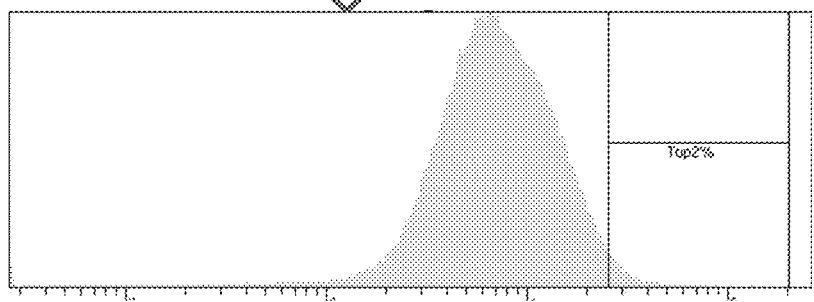
Figure 13C:
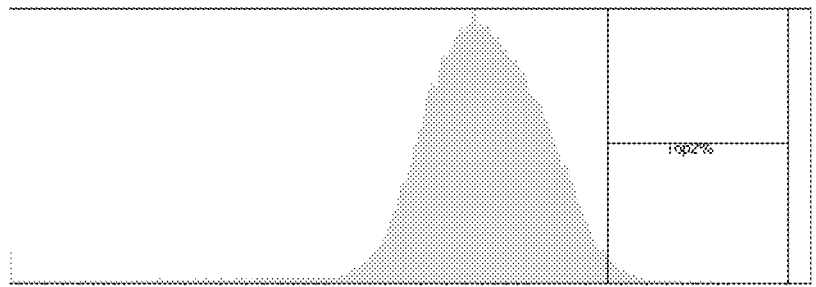

FIG. 13A is a schematic diagram of an exemplary plasmid construct for sensing PobA activity. PobA enzyme in *P. putida* converts 4HB into PCA. In order to improve the catalytic efficiency of PobA, a plasmid construct consisting of pPcaU1.2 (SEQ ID NO: 3) and pobA gene from *P. putida* expressed as sfGFP fusion and under positive feedback regulation of PCA (scheme represented in FIG. 1B) was created (FIG. 13A) (SEQ ID NO: 30). FIG. 13B is a graph representing 4HB concentration-dependent fluorescence response of CJ182 cells (shown in FIG. 13A). With conversion of 4HB into PCA, sfGFP-PobA fusion is expressed and results in observed fluorescence of the cells. FIG. 13C shows a *P. putida* cell population harboring the above plasmid construct and where pobA gene has been diversified (Theoretical library diversity>20,000). Each cell is expected to have single sequence of pobA on the plasmid. The library of cells was plated on 100 μM 4HB, scraped and analyzed using flow cytometry for cell fluorescence. FIG. 13C (top panel) shows the fluorescence histogram confirming two distinct population with low and high cell fluorescence respectively. Top 3% fluorescent cells were sorted (using BD FACSAria III flow cytometer) and regrown in 100 μM 4HB on plate, scraped and analyzed again using flow cytometer. In this round, top 1% fluorescent cells were sorted and collected and the process was repeated for one more round. The fluorescence distribution of the cells in the third round (middle panel) was similar to the distribution observed with cells harboring wild-type PobA (PobA-wt) (bottom panel). Top 2% sorted population from the third round was plated and 10 colonies were sequenced using Sangar sequencing. The sequence confirmed the emergence of wild-type PobA sequence, confirming that a majority of the mutations in the library were deleterious to the PobA activity. The high throughput approach using PCA sensor helped to screen through the library efficiently, and the wild-type PobA sequence, which was represented as a needle-in-a-haystack in the diversified library, could be sorted in as low as three sorting rounds of top 3%, 1%, and 2%, based on cell fluorescence.

Example 5

Development of a Muconate Sensor

CatM belongs to a LysR family of transcription factor and is involved in metabolism of ccMA in *Acinetobacter baylyi* ADP1. The intergenic region of catM and catB in *A. baylyi* ADP1 consit of operator and promoter regions for the expression of CatM and downstream CatB. Utilizing the same format, where the regulated downstream catB gene was replaced with sfgfp gene as a reporter in pBTL2 backbone a synthetic construct was made which when evaluated in a ccMA production strain (for example CJ184) failed to show any fluorescence. Hence, optimization of the biosensor via mutating operator and promoter regions in the intergenic region, was pursued.

Figures 14A, 14B:
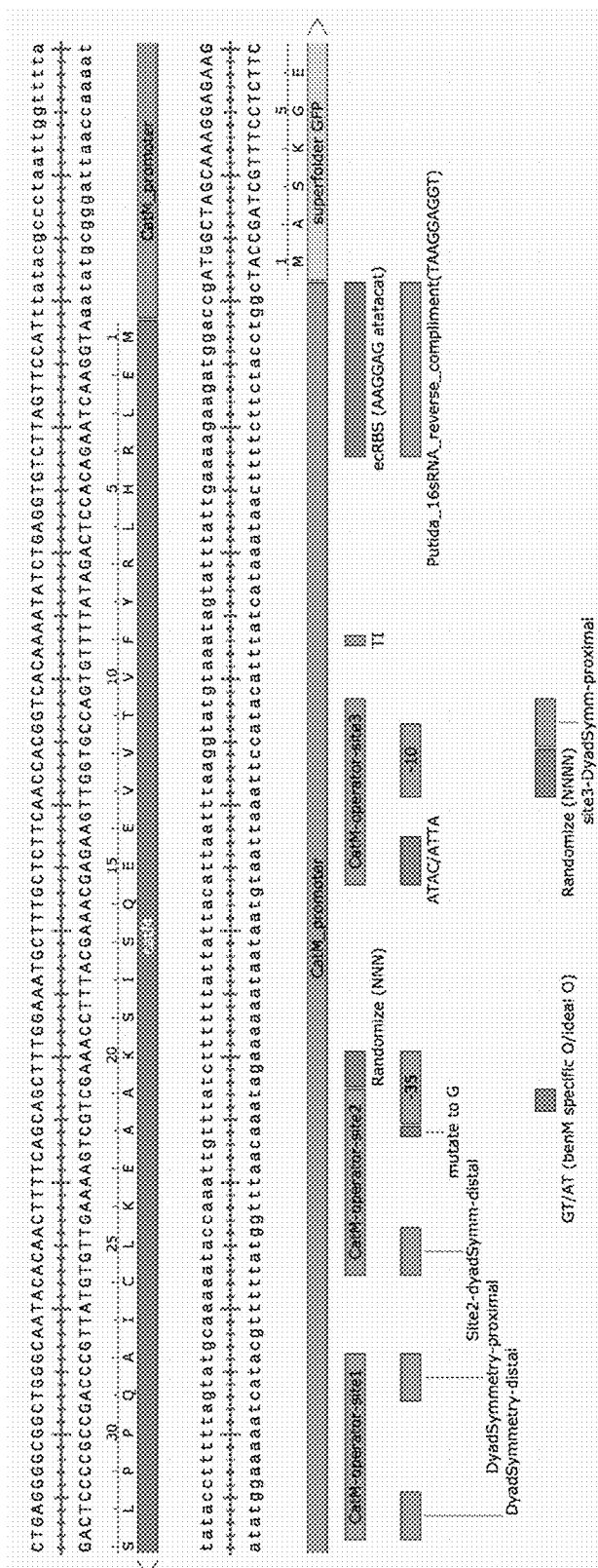
FIGS. 14A-14D show promoter diversification, dose-response plots of sensitive cis, cis-muconic acid (ccMA) sensor, redesign of the ccMA binding pocket and dose-response plot of ccMA sensor with reduced sensitivity.

FIG. 14A represents the *Acinetobacter baylyi* CatM promoter region used for selection of ccMA sensing in *P. putida* KT2440. The regions that were partially diversified or completely randomized are marked 'red' and the mutations pursued are labeled. For example −10 and −35 sites were partially randomized for saturation, the ribosome binding site (RBS) was made compatible to the consensus sequence AAGGAG followed by eight bases to the start codon "ATG" of the reporter. Overall the library diversity was expected to be well above 60,000. Using a method similar to what has been described in Example 1-3, catM gene, diversified regulatory region, and sfgfp were inserted into the pBTL2 backbone. The completed circular plasmids, carrying Kanamycin resistance marker, were then transformed into electrocompetent cells of *P. putida* strain CJ184. The transformation gave well above 60,000 colonies to cover the library adequately. The colonies were scraped and grown LB and 50 μg/mL kanamycin (Kan$_{50}$) and in the presence of 10 mM Benzoate or PCA, since CJ184 is capable of accumulating ccMA from both these substrates (Vardon et al, *Energy Env Sc*, 8:617-628, 2015). As a control, the library was also grown in LB+Kan$_{50}$ but lacking the precursors for ccMA. Post 16 h of growth at 30° C., the samples were analyzed on a flow cytometer (BD FACSAria III). Three rounds of growth and sorting consisted of negative-positive-positive or positive-negative-positive selection where negative selection (sorting low fluorescence from no Benzoate/PCA culture) was required to eliminate constitutively active sensor, and positive selection (sorting high fluorescence from the Benzoate/PCA supplemented cultures) was needed to choose the most active sensor. While 10 mM of Benzoate or PCA was used in Rounds 1 and 2, the dosage was decreased to 1 mM in the final round. Post third round of sorted population, a fraction was plated on LB agar+Kan$_{50}$ plates and a few colonies evaluated for PCA, Benzoate and Catechol response, considering CJ184 strain is capable of converting them all to final product ccMA.

pCatM_C2 (SEQ ID NO: 7) that consist of optimized promoter CatM_C2 (SEQ ID NO: 12 and 13 (reverse complement)), showing high response to PCA was identified. Another variant of the plasmid, with promoter CatM_A9, (SEQ ID NO: 23) showed weaker fluorescence but very similar dose-response as the CatM_C2 was also identified which could be useful in a few cases. FIG. 14B is a plot showing intracellular production and sensing of ccMA in *P. putida* (CJ184) using pCatM_C2 sensor. CJ184, which is capable of metabolizing PCA into ccMA as a final product (ccMA production strain) shows a clear dose-response with PCA. Another strain, CJ072, with a knockout mutation in PCA-ccMA pathway (Non-production strain) failed to show any dose-response with PCA. Similar dose-response was observed with other substrates such as Benzoate or catechol. As evident from the dose-response plot (FIG. 14B) the CatM_C2 sensor saturates at ~ 100 μM, the biosensor has limited application in certain high muconate producing strains.

Figure 14C:
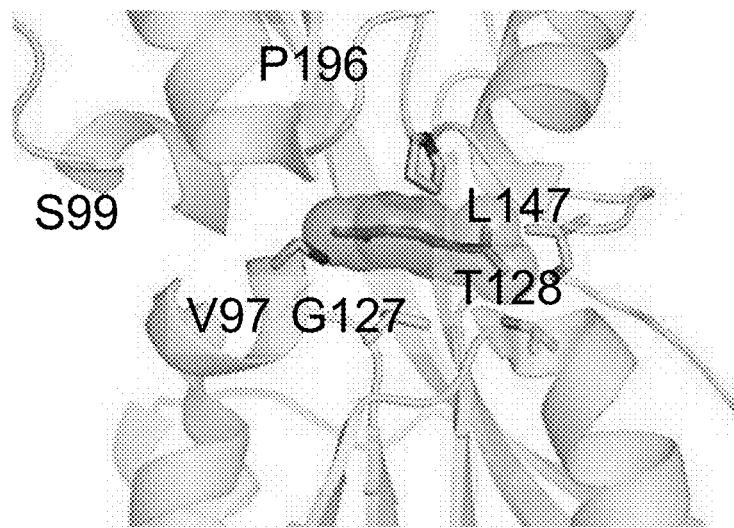
Figure 14D:
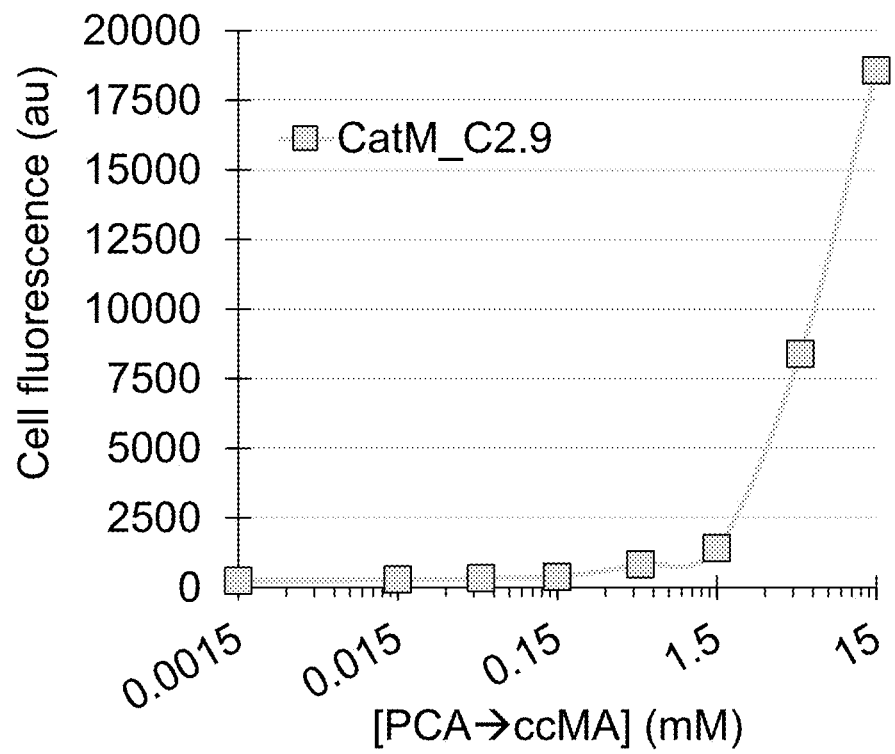

In order to address that problem, we went ahead to create a diversified library of the CatM inducer binding pocket. With an availability of a 'holo' crystal structure (PDB code 2F7C) where amino acid side chains within 5 Å radius were selected for diversification. FIG. 14C shows the residue numbers that were selected for diversification in the CatM inducer binding pocket. With 'natural drift' mutation strategy, V97→I/L/A/T, S99→A, G127→A, T128→A, L147→V/I and P196→S were introduced into the CatM sequence in a fashion such that either native or one of the proposed mutations at each residue position appeared. This gave a library with theoretical diversity ~300. The library was created in the promoter background of pCatM_C2, which was then transformed into *P. putida* strain CJ184, and processed using flow cytometry in a manner as described previously for promoter evolution. FIG. 14D shows a selected variant (CatM_C2.9) with low sensitivity for an ideal dose-response at high ccMA titer, that is >10 mM. The variant CatM_C2.9 (SEQ ID NO: 25) includes the following mutations in the inducer binding pocket: V97I, G127A, T128A and L147V.

Example 6

Development of a BKA Sensor

For constructing and evaluating a BKA sensor, there were two approaches that were pursued. Since BKA responsive transcription factor (PcaR, SEQ ID NO: 19) is native to *P. putida* KT2440, we went ahead to design an optimal promoter which will be sufficient to respond to BKA accumulation via the native genomic pcaR expression. The construct, where partial intergenic region of PP_1374 gene and pcaR was used to in pBTL2 backbone to create a construct pPcaR_promo (SEQ ID NO: 21). This BKA sensor construct was transformed in both *P. putida* KT2440 and CJ390 and evaluated using precursors of BKA, such as PCA and catechol.

Figure 15A:
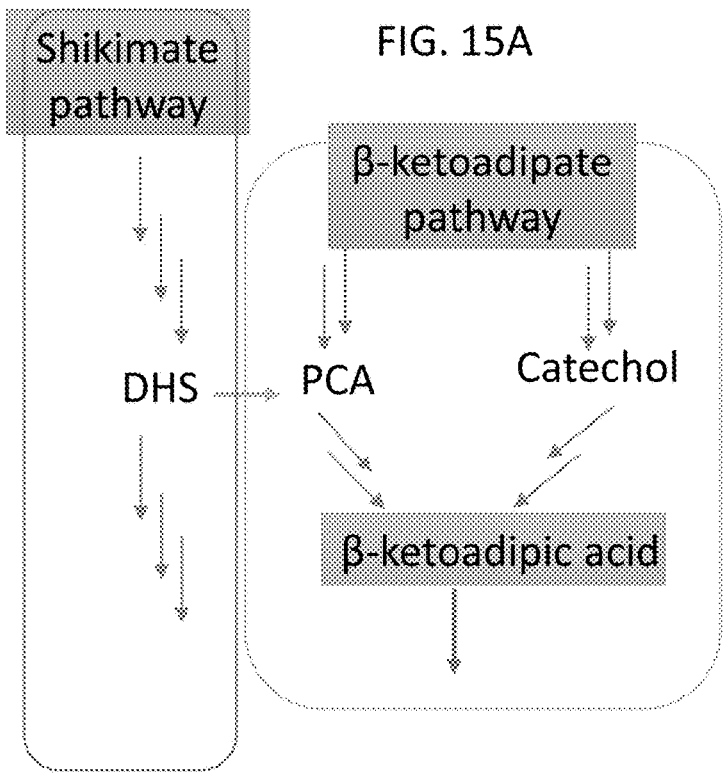
FIGS. 15A-15E are a series of panels related to pathways leading to (3-ketoadipic acid (BKA) and whole cell biosensing in *P. putida* strains.
Figure 15B:
Figure 15C:
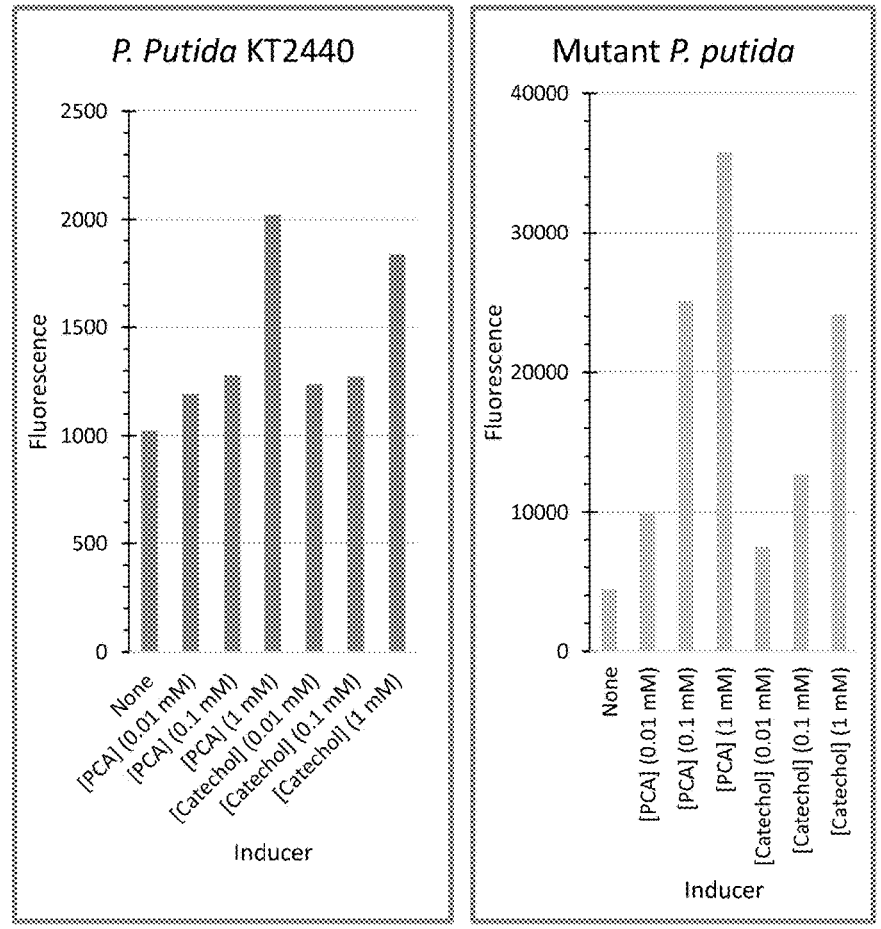

FIG. 15A shows the protocatechuate and catechol branches of the β-ketoadipate pathway in *P. putida* KT2440 and a heterologous shunt feed (green arrow) from shikimate pathway. *P. putida* variant (CJ390) consist of an added shunt (green arrow) and deleted genes of BKA metabolizing enzymes (PcaIJ) (red arrow). Hence, as expected, CJ390 is capable of making BKA from glucose or LB but at the same time spiking with immediate precursors, like PCA or catechol, would give spike in BKA and hence increase in fluorescence with increasing precursor concentration. FIG. 15B shows low fluorescence in *P. putida* KT2440 and high fluorescence in a CJ390, which is capable of making and accumulating BKA when grown on LB medium. FIG. 15C shows dose response of BKA sensor in *P. putida*. Native KT2440 cannot make BKA from glucose and BKA is transiently accumulated due to activity of PcaIJ. This results in significantly lower response compared to mutant *P. putida*, which can convert glucose or spiked PCA and catechol into BKA and also accumulate BKA. In high BKA producing strain from glucose, this BKA sensor failed to show any dose-dependent response to BKA precursors like catechol and PCA. Hence, modification of the BKA binding pocket in PcaR was necessary to reduce the sensitivity of the sensor.

Figure 15D:
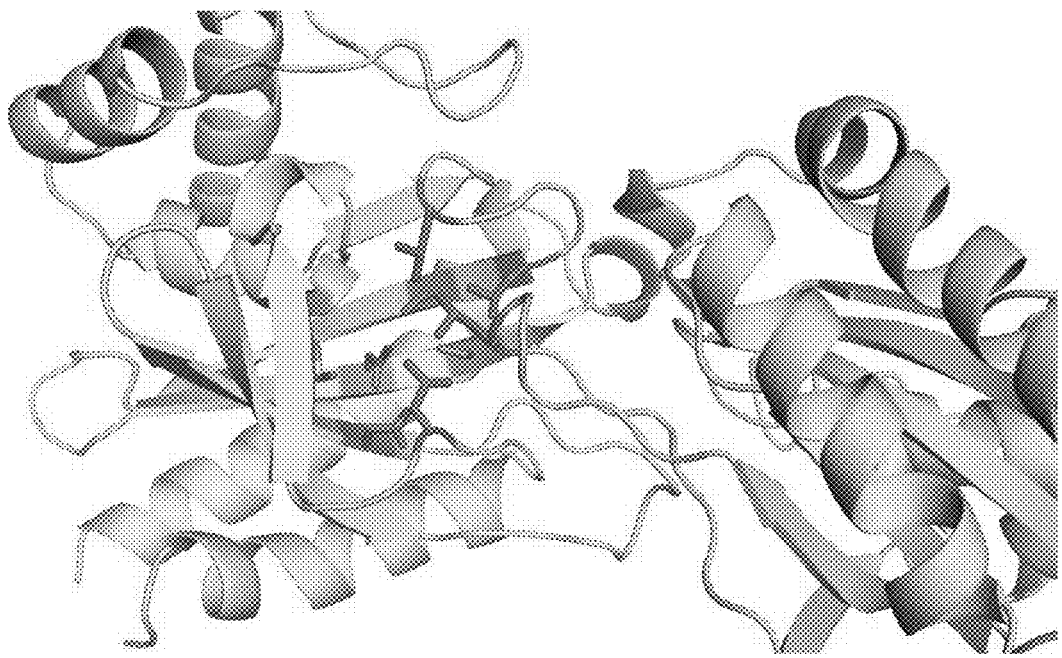
Figure 15E:
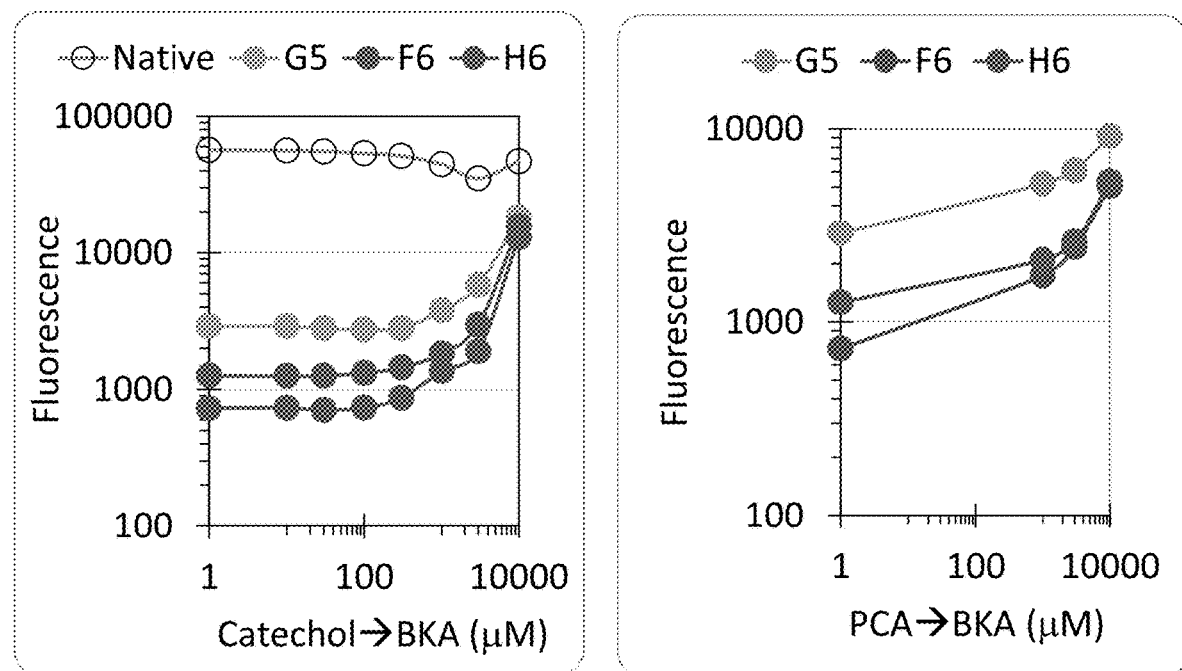

Rosetta homology modeling, using a known structure of a transcription factor with a homologous sequence (PDB code 2G7U) was used to get a 3D estimate of the PcaR inducer binding domain. Based on the predicted structure, several amino acids in the pocket were identified to be suitable for mutagenesis. FIG. 15D shows highlighted positions which were chosen for diversification to reduce the sensitivity of BKA sensor. Positions N140, L161, L166, L172, M179, L234, L238, S240, N257 and S259 were mutated for diversification to achieve N/S/T/I at positions 140 and 257, L/M/V at positions 161, 166, 172, 179, 234 and 238, S/T/A at position 240 and 259. This produced a library of diversity>100,000. The library was transformed in high BKA producing strain where native pcaR gene was deleted (strain NN7) and screened for increase fluorescence response with increasing dose of precursors while in the LB mediated BKA production background. FIG. 15E shows dose response plots of identified variants that show low sensitivity and hence detection of high concentration of BKA titer. As seen in the right panel, the native PcaR (SEQ ID NO: 19) expressing plasmid pPcaR (SEQ ID NO: 22) showed saturation in fluorescence, while the variants PcaR-G5 (SEQ ID NO: 26), PcaR-F6 (SEQ ID NO: 27) and PcaR-H6 (SEQ ID NO: 28) showed dose dependent response with BKA precursors, catechol and PCA, assuming all the precursors are converted to BKA in the background of BKA production from glucose/LB growth media.

Example 7

High Throughput Selection of Paraoxonase 1 Enzyme with Enhanced Activity

Since p-nitrophenol (pNP) is a chromogenic chemical leaving group, it has become ubiquitous reporter in surrogate substrates for hydrolytic catalyst characterization. Yet a spectrophotometric monitoring format is limited to low-throughput bulk samples, typically a 96-well or 384-well plate with one well for each enzyme species. Moreover, this can lose sensitivity amidst background absorption in many media. Instead, we previously reported a 'smart' microbial cell technology (SMC) and single-cell monitoring of pNP using a computationally re-designed *Acinetobacter baylyi* PobR transcription factor (TF) regulating expression of a fluorescent protein reporter. We showed this sensor-reporter system could detect intracellular organophosphate hydrolysis by a phosphotriesterase (PTE) via the pNP leaving group. We showed the single cell fluorescence correlated with PTE enzymatic activity (Jha et al., *Nucl. Acids Res.* 44:8490-8500, 2016).

We extended this technology to library-based design of a mammalian serum paraoxonase 1 (PON1) enzyme (Harel et al., *Nat. Struct. Mol. Biol.* 11:412-419, 2004). The previous state-of-the-art in PON1 performance was achieved mainly by mergers of point mutations chosen in the vicinity of the catalytic pocket (Aharoni et al., *Proc. Natl. Acad. Sci. USA* 101:482-487, 2004). Individual mutations L69V, H115W and V346A enhanced hydrolysis of organophosphates (OPs) by four- to sixteen-fold higher catalytic efficiency (Amitai et al., *FEBS J.* 273:1906-1919, 2006). Its variants have been adapted for catalysis and stereoselectivity against multiple OP substrates. Directed evolution of PON1 via DNA shuffling using homologous proteins (Aharoni et al., *Proc. Natl. Acad. Sci. USA* 101:482-487, 2004) or error-prone-PCR libraries (Gupta and Tawfik, *Nat. Methods* 5:939-942, 2008) have discovered mutations improving expression, substrate specificity and catalytic efficiency. However, without a means for direct selection for enhanced activity, library size and throughput are bottlenecked by the need for activity assays with individual genotypes expressed and lysed in separate sample wells.

The technique described here (referred to in this example as "smart microbial cells" or SMC; e.g., FIGS. 1A and 1B) allows for catalysis and sensing in the same microbial cell. For a practical library application, we simplified and improved the signal to noise ratio of the biosensor. This was achieved by gene fusing the PON1 to the GFP so that the TF is also regulating the catalytic enzyme expression as well (scheme shown in FIG. 1B). This fusion is expected to have three distinct effects. First, it provides positive feedback, such that more the activity, the more PON1 is expressed, and in turn further 'feeds' the activity. The feedback, hence, would enhance the sensitivity to weak activity by raising the signal above both ambient background and leaky expression of the GFP reporter. Notably, when the PON1 is inactive there is no positive feedback, so basal expression will not be increased by the feedback. Second, feedback will amplify the already present correlation between activity and GFP expression. Third, for suitably chosen GFP, the fluorescence signal conveniently reports the amount of fused PON1 present, allowing normalization for specific activity.

A weakly folding GFP, placed at the C-terminal after a protein-of-interest is known to function as folding reporter since a misfolded (insoluble) N-terminal protein will interrupt the formation of the subsequently translated GFP chromophore (Gupta and Tawfik, *Nat. Methods* 5:939-942, 2008; Waldo et al., *Nat. Biotechnol.* 17:691-695, 1999). In contrast, our assay specifically suppressed that effect using 1) an N-terminal GFP and 2) a super-folding variant of GFP (Pedelacq et al., *Nat. Biotechnol.* 24:79-88, 2006). Thus, it directly reports enzyme activity and not misfolding. However, because of the positive feedback, we still get the benefit of sensing misfolding since enzyme inactivity means no feedback for enhanced GFP expression.

Figure 16A:
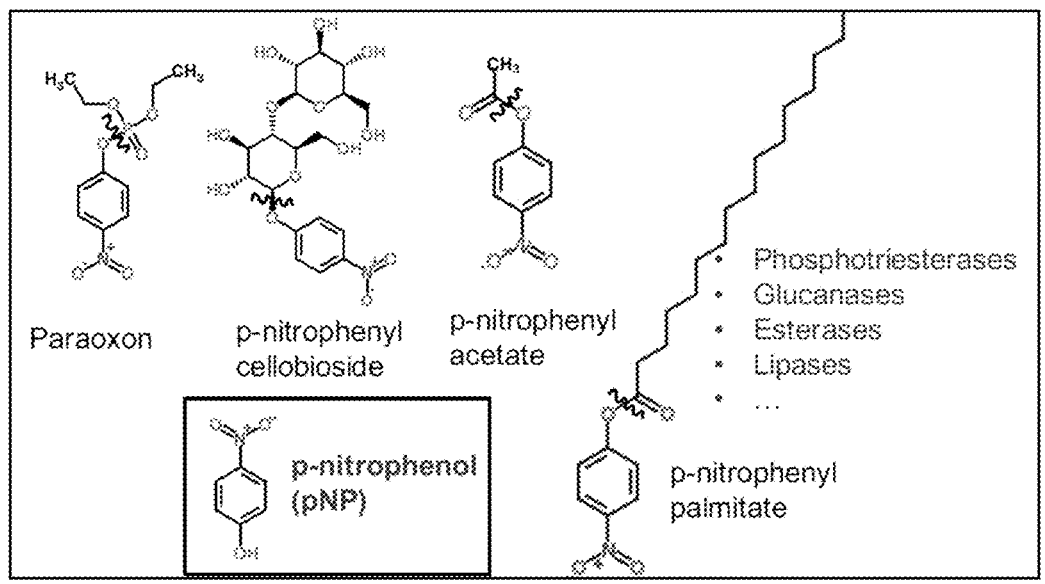
FIGS. 16A-16D show 'Catalyze' and 'sense' system for hydrolysis reactions.
Figure 16B:
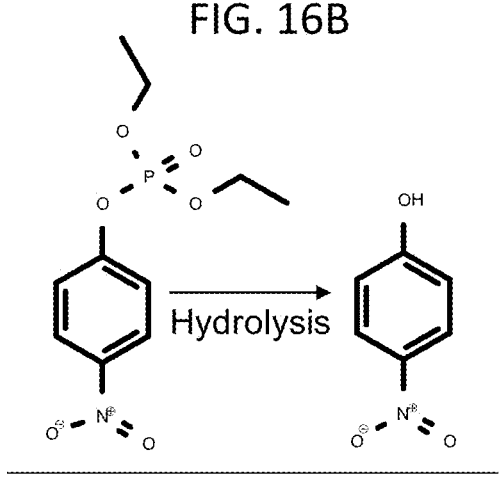
Figure 16C:
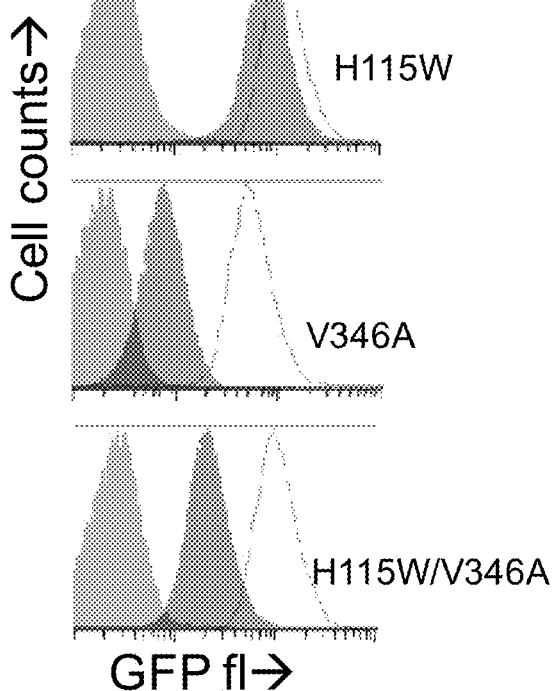

The sfGFP-PON1 fusion can catalyze the hydrolysis of paraoxon (PXN) where pNP is a leaving group (FIG. 16B). Based on the catalytic efficiency and the cytoplasmic concentration of the hydrolase, PXN hydrolysis results in a correlated pNP production inside the microbial cell that ultimately determines activation of the pNP sensor and accumulation of sfGFP in the cells. Comparison of SMCs with PON1-G3C9 (SEQ ID NO: 32) (native like) and PON1-H115W mutant grown in PXN showed a higher cell fluorescence in the latter (FIG. 16C), which is consistent with the higher catalytic efficiency observed for PON1-H115W (Amitai et al., FEBS J. 273:1906-1919, 2006). The other published variant PON1-V346A, failed to show higher cell fluorescence than G3C9 expressing cells, even though the variant has higher catalytic efficiency for PXN hydrolysis, possibly due to reduced protein expression and/or slower folding rate caused by the mutation. The PON1 version that combines the two mutations H115W/V346A showed partial recovery of the cell fluorescence in the presence of PXN substrate (FIG. 16C, Table 6). When pNP was used as an inducer, such that the expression of sfGFP-PON1 expression is independent of the catalytic efficiency of PON1, modest differences in cell fluorescence were still captured across the PON1 variants indicating V346A mutation could be detrimental to PON1 expression and stability (FIG. 16C, Table 6).

Figure 16D:
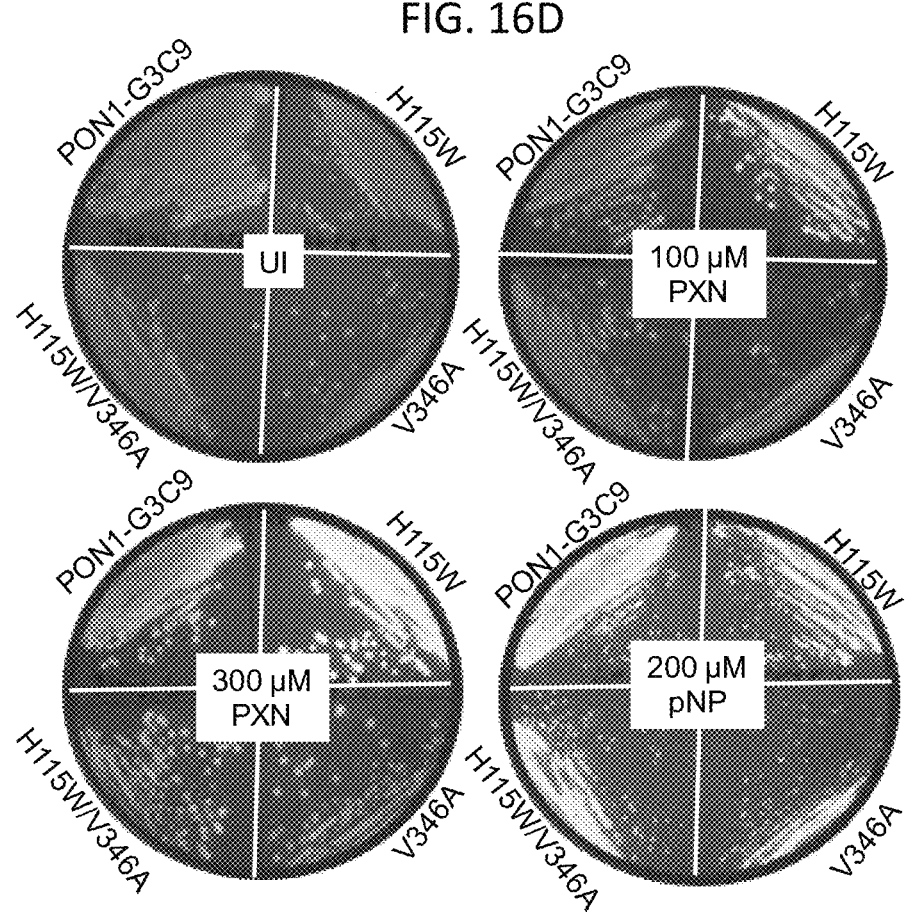

Table 6. Raw whole cell fluorescence intensity[a] with pNP sensor and sfGFP-PON1 expression under positive feedback regulation of pNP sensor and measured using a flow cytometer PON1-G3C9 expressing cells. At 200 μM pNP, irrespective of the PON1 variant expressed, the SMCs were saturated with fluorescence under an illuminator, beyond the capability to distinguish them visually with the naked eye (FIG. 16D).

Figure 17A:
FIGS. 17A-17G show evolution of PON1.

The next step was to move this technology to library screening where two separate libraries were created using PON1-H115W as a starting scaffold. The first library (Lib1) targeted peripheral mutations on loop 69-74 (based on the structural information of PON1 bound to a competitive inhibitor molecule 2-hydroxyquinoline (PDB code 3SRG) (Table 7). This loop is expected to play a critical role in interaction with the substrate/transition state, since the loop otherwise disordered in apo state, gained structure only in the presence of inhibitor in the pocket. The second library (Lib2) consisted of mutations around the catalytic pocket mostly based on the literature (Table 8). The goal of Lib2 was to discover any combinatorial solution of synergistic mutations, which earlier were tried mostly as single point mutations (FIG. 17A). Theoretical diversity of each library, ~20,000 was reasonably matched to the SMC based plate assay, where on a single large petri dish (135 mm diameter) one can have ~$10^4$ isolated colonies demanding two to four petri dishes for modest over coverage.

Table 7. Mutational library 1[a]

TABLE 7

| | Mutational library 1[a] | | | | | |
|---|---|---|---|---|---|---|
| | L69 | K70 | Y71 | P72 | G73 | I74 |
| Diversified codon | DTA | NWW[b] | NDT | NCN | RST | AHT |
| Amino acids | LVI | YHNDQKEFL(3)I(2)V(2)[c]* (SEQ ID NO: 51) | RNDCGHILFSYV (SEQ ID NO: 52) | S(4)P(4)T(4)A(4) (SEQ ID NO: 53) | TSAG (SEQ ID NO: 54) | ITN |
| Unique variants | 3 | 12 | 12 | 4 | 4 | 3 |

[a]Theoretical library diversity = 3 × 12 × 12 × 4 × 4 × 3 = 20736
[b]one-sixteenth variant has premature STOP codon
[c]Number in parentheses denotes number of degenerate codons for a particular amino acid

TABLE 6

Raw whole cell fluorescence intensity[a] with pNP sensor and sfGFP-PON1 expression under positive feedback regulation of pNP sensor and measured using a flow cytometer

| PON1 variant | UI | pNP (200 μM) | PXN (1.6 mM) |
|---|---|---|---|
| G3C9 | 168 ± 5 | 7052 ± 124 | 1761 ± 158 |
| H115W | 301 ± 42 | 13934 ± 802 | 10276 ± 386 |
| V346A | 174 ± 29 | 6263 ± 57 | 895 ± 39 |
| H115W/V346A | 248 ± 36 | 11484 ± 2032 | 2410 ± 669 |

[a]Mean cell fluorescence intensity from cultures in duplicate. Errors depicted as standard deviation

[a]Mean cell fluorescence intensity from cultures in duplicate. Errors depicted as standard deviation The SMCs when plated on a solid LB-agar medium supplemented with different induction conditions, recaptured the fluorescence signal observed in the liquid culture (FIG. 16D). While at 100 μM PXN, fluorescent colonies were observed only in case of PON1-H115W and that further gained brightness at 300 μM PXN supplemented growth medium, SMCs expressing PON1-V346A continued to show weaker fluorescence than both PON1-H115W and

[a]Theoretical library diversity=3×12×12×4×4×3=20736
[b]one-sixteenth variant has premature STOP codon
[c]Number in parentheses denotes number of degenerate codons for a particular amino acid Table 8. Mutational library 2a

TABLE 8

| | Mutational library 2[a] | | | | | | | |
|---|---|---|---|---|---|---|---|---|
| | G116 | N168 | F222 | N224 | L267 | N270 | I291 | F292 |
| Diversified codon | RST | VAT | WWT | VAC | VTT | VAC | NTC | NTC |
| Amino acids | TSAG (SEQ ID NO: 54) | HND | INYF (SEQ ID NO: 55) | HND | LIV | HND | FLIV | FLIV |
| Unique variants | 4 | 3 | 4 | 3 | 3 | 3 | 4 | 4 |

[a]Theoretical library diversity = 4 × 3 × 4 × 3 × 3 × 3 × 4 × 4 = 20736

[a]Theoretical library diversity=4×3×4×3×3×3×4×4=20736

Figure 17B:
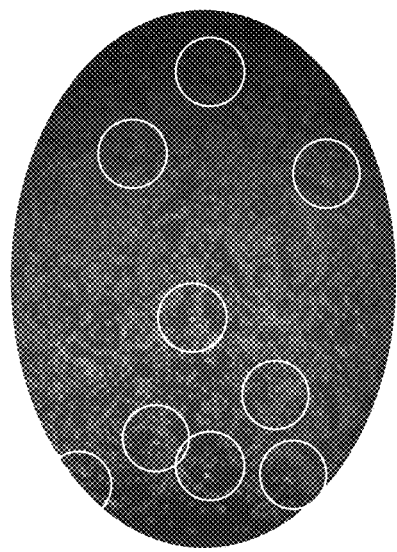
Figure 17C:
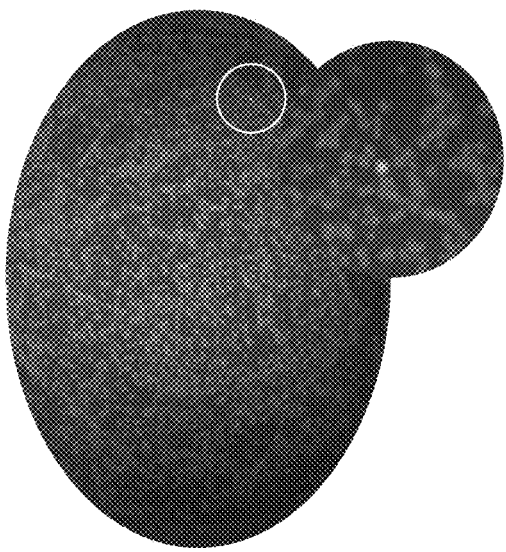

In order to efficiently screen the library, the biosensor/biocatalyst plasmid consisting of variants of PON1 was directly transferred to high transformation efficiency DH5α cells. The SMC libraries harboring two sets of genetic variations showed a very different display on the plate supplemented with approximately 330 µM PXN. While the peripheral mutations in PON1 incorporated in Lib1, showed multiple colonies distinctly brighter than the surrounding colonies (FIG. 17B), Lib2 consisting of mutations in the catalytic pocket proved to consist of sequences that were mostly detrimental to the activity of PON1. A single colony though stood out from the rest and was picked for further experimental verification (FIG. 17C). The colony picking can further be made more stringent by using lower PXN (for example 100 µM) in the growth media and colonies selected based on the fluorescence intensity under an illuminator.

Figure 17D:
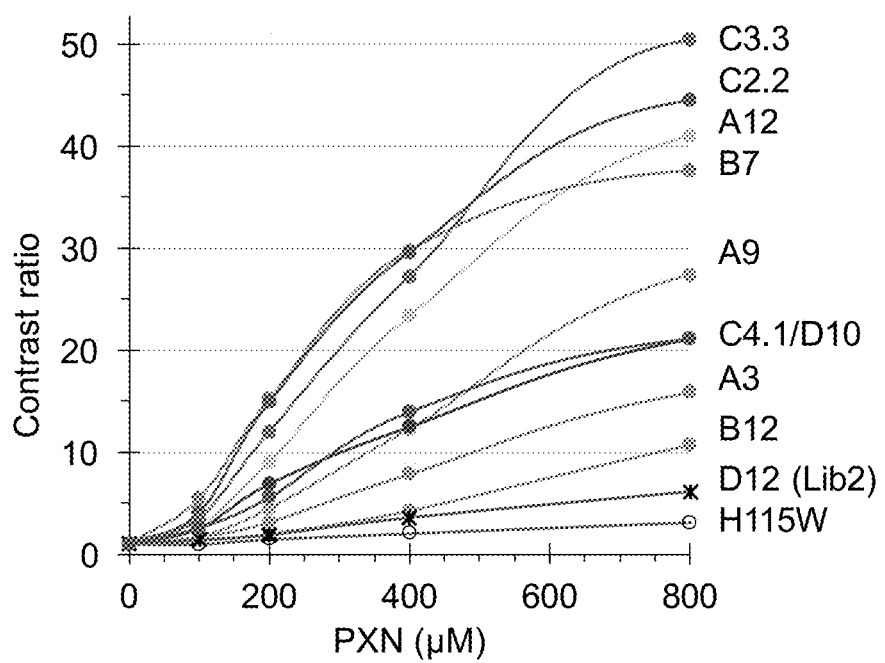
Figure 17E:
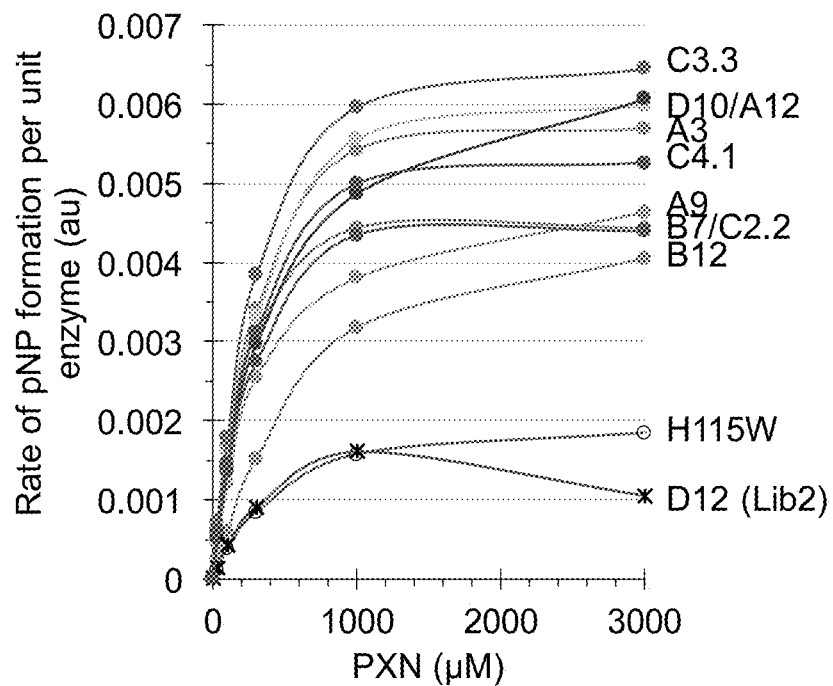

Whole cell catalysis and sensing using the picked clones at varying concentration of the substrate PXN, showed enhanced contrast ratio (3-15 fold higher than the scaffold) for selected clones from Lib1, while the single picked clone from Lib2 showed a marginal 2-fold higher contrast ratio compared to the scaffold (FIG. 17D). The clones were further confirmed for improved activity by using clear cell lysates that were normalized for sfGFP fluorescence (the enzyme variants expressed as sfGFP-PON1 fusion by inducing the same clones with 200 µM pNP) and assayed for activity at different concentrations of PXN. Over H115W mutation, which was a part of the scaffold, the Lib1 clones showed 2-4 mutations (Table 9) while Lib2-D12 also showed only two mutations (F222I, F292I). Interestingly L69V mutation, which is present in all the Lib1 clones has also been extensively investigated for hydrolysis of many OPs where, in the absence of H115W, four-fold increase in catalytic efficiency was seen over the wild-type (Amitai et al., *FEBS J.* 273:1906-1919, 2006). The most notable aspect of comparison between the in vivo activity measurements (FIG. 17D) and the in vitro measurements (FIG. 17E) is the relative ranking of the different PON1 variants. While Lib1-C3.3 did show highest Vmax in both formats of experiment, the Lib2-D12 was the lowest in both cases. Lib1-C3.3 also had highest expression and solubility next only to the starting scaffold (showing 95% yield), Lib2-D12 showed a low 50% protein yield compared to the scaffold based on the fluorescence of the cell lysate. The solubility of other PON1 variants ranged between these two extreme values.

Table 9. Observed mutations in the improved colonies from Lib1

TABLE 9

| Observed mutations in the improved colonies from Lib1 | | | | |
| --- | --- | --- | --- | --- |
| Position# | 69 | 70 | 71 | 73 |
| Native | L | K | Y | G |
| A3 | V | Y | V | |

TABLE 9-continued

| Observed mutations in the improved colonies from Lib1 | | | | |
| --- | --- | --- | --- | --- |
| Position# | 69 | 70 | 71 | 73 |
| A9 | V | Q | I | |
| A12 | V | L | | S |
| B7 | V | Q | I | A |
| B12 | V | H | V | S |
| D10 | V | L | | |
| C2.2 | V | Q | V | A |
| C3.3 | V | Q | L | A |
| C4.1 | V | F | V | |

Figure 17F:
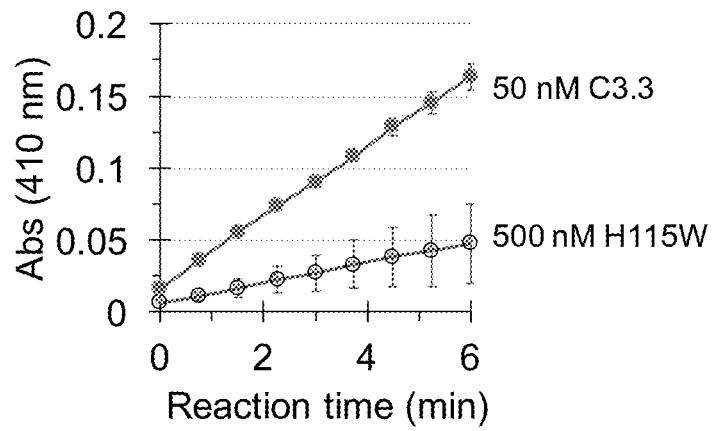
Figure 17G:
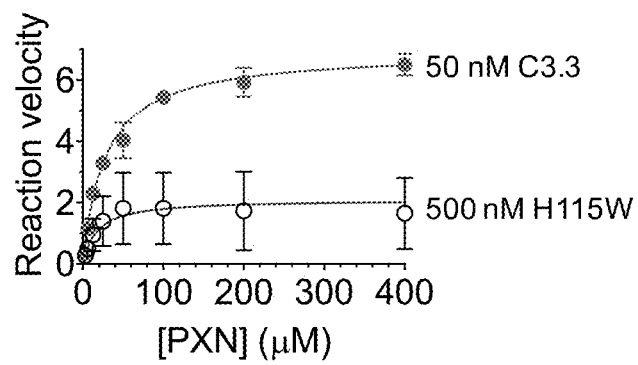

Finally, the gene for top PON1 variant Lib1-C3.3 (H115W, L69V, K70Q, Y71L, G73A) and the scaffold (H115W) were transferred to a pRSF-1b vector (Novagen) and expressed as a C-terminal 6×His-tagged protein. Post two-step purification using affinity column and a size exclusion chromatography, pure fractions were combined and tested for activity at varying concentrations of PXN. At a ten-fold lower protein concentration in an enzymatic assay using 400 µM of PXN for paraoxonase activity, the linear rate of Lib1-C3.3 variant exceeded that of PON1-H115W by three-fold, confirming that the turnover number of the new variant is approximately thirty-fold higher than the starting sequence (FIG. 17F). With some challenges in determining Km values of the PON1 variants, especially in case of weaker enzyme (PON1-H115W), one to two-orders of magnitude of enhancement in catalytic efficiency ($k_{cat}/K_m$) was observed in the new version of PON1 (FIG. 17G).

The work presented here summarizes a method to navigate through a large combinatorial space encountered during enzyme evolution. Using this method, we can screen multiple combinations of mutations which otherwise are difficult to explore with conventional methods of mutagenesis one at a time and later combining the mutations for an additive effect. We showed that our method could pull out the L69V mutation from the library and determined it to be beneficial along with as many as 1-3 mutations in its vicinity. Mutations at K70 observed in PON1 variants with gain-of-function would have been counter-intuitive in structure-based mutagenesis studies since the residue is pointing away from the catalytic pocket. The ability to screen multiple mutations all at once and visually select without need of any sophisticated instrumentation, allows for screening many mutations at a time for finding a synergistic set of alterations with large gain-of-function.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A biosensor comprising:
   (i) a protocatechuic acid (PCA) biosensor comprising a nucleic acid encoding a PcaU protein comprising one or more amino acid substitutions at an amino acid corresponding to amino acid position 147, an amino acid corresponding to amino acid position 148 of SEQ ID NO: 56, or both, wherein the PcaU protein comprises at least 95% sequence identity to SEQ ID NO: 5;
   (ii) a cis,cis-muconic acid (ccMA) biosensor comprising a nucleic acid encoding a CatM protein comprising an amino acid substitution at two or more of amino acid positions corresponding to amino acids 97, 127, 128, and 147 of SEQ ID NO: 14;
   a CatM-regulated promoter; and
   a nucleic acid encoding a reporter protein operably linked to the promoter,
   wherein the CatM protein is encoded by a nucleic acid sequence with at least 90% sequence identity to nucleotides 990-1898 of SEQ ID NO: 7; or
   (iii) a β-ketoadipic acid (BKA) biosensor comprising a nucleic acid encoding a PcaR protein comprising an amino acid substitution at two or more of amino acid positions corresponding to amino acids 172, 238, 240, and 257 of SEQ ID NO: 19;
   a PcaR regulated promoter; and
   a nucleic acid encoding a reporter protein operably linked to the promoter,
   wherein the PcaR protein is encoded by a nucleic acid sequence with at least 90% sequence identity to SEQ ID NO: 19.

2. The PCA biosensor of claim 1, wherein the nucleic acid encodes glycine, threonine, or proline at amino acid position 147, tyrosine or phenylalanine at amino acid position 148, or both.

3. The PCA biosensor of claim 1, wherein:
   the PcaU protein is encoded by a nucleic acid sequence comprising at least 90% sequence identity to SEQ ID NO: 4.

4. A vector comprising:
   the PCA biosensor of claim 1;
   a promoter comprising or consisting of nucleotides 1824-2104 of SEQ ID NO: 2; and
   a nucleic acid encoding a reporter protein operably linked to the promoter.

5. The vector of claim 4, wherein the vector comprises a nucleic acid sequence with at least 90% sequence identity to SEQ ID NO: 2 or SEQ ID NO: 3.

6. A cell comprising the PCA biosensor of claim 1.

7. The ccMA biosensor of claim 1, wherein the promoter comprises nucleotides 1899-2021 of SEQ ID NO: 7.

8. A vector or a cell comprising the ccMA biosensor of claim 7.

9. The vector of claim 8, wherein the vector comprises a nucleic acid sequence with at least 90% sequence identity to SEQ ID NO: 7.

10. The BKA biosensor of claim 1, wherein the promoter comprises the nucleic acid sequence of SEQ ID NO: 8.

11. A vector or a cell comprising the BKA biosensor of claim 10.

* * * * *

SEQUENCE LISTING

<160> NUMBER OF SEQ ID NOS: 56

<210> SEQ ID NO 1
<211> LENGTH: 4371
<212> TYPE: DNA
<213> ORGANISM: Artificial Sequence
<220> FEATURE:
<223> OTHER INFORMATION: pPcaU1 plasmid

<400> SEQUENCE: 1
tacgtaagag gttccaactt tcaccataat gaaataagat cactaccggg cgtatttttt    60

```
gagttatcga gattttcagg agctaaggaa gctaaaatga gccatattca acgggaaacg    120
tcttgctcga ggccgcgatt aaattccaac atggatgctg atttatatgg gtataaatgg    180
gctcgcgata atgtcgggca atcaggtgcg acaatctatc gattgtatgg gaagcccgat    240
gcgccagagt tgtttctgaa acatggcaaa ggtagcgttg ccaatgatgt tacagatgag    300
atggtcaggc taaactggct gacggaattt atgcctcttc cgaccatcaa gcattttatc    360
cgtactcctg atgatgcatg gttactcacc actgcgatcc cagggaaaac agcattccag    420
gtattagaag aatatcctga ttcaggtgaa aatattgttg atgcgctggc agtgttcctg    480
cgccggttgc attcgattcc tgtttgtaat tgtcctttta cggcgatcg cgtatttcgt     540 ctcgctcagg cgcaatcacg aatgaataac ggtttggttg gtgcgagtga ttttgatgac    600
gagcgtaatg gctggcctgt tgaacaagtc tggaaagaaa tgcataagct tttgccattc    660
tcaccggatt cagtcgtcac tcatggtgat ttctcacttg ataaccttat ttttgacgag    720
gggaaattaa taggttgtat tgatgttgga cgagtcggaa tcgcagaccg ataccaggat    780
cttgccatcc tatggaactg cctcggtgag ttttctcctt cattacagaa acggcttttt    840
caaaaatatg gtattgataa tcctgatatg aataaattgc agtttcactt gatgctcgat    900 gagttttct  gagggcggat cccctcaag tcaaagcct ccggtcggag cttttgact      960 ttctgctatg gaggtcaggt atgattttac aggatattgc gcaattcacg cgcagttttcc   1020 tgcagtaacg gcagaatatg ctgaatcagg tattctttcg tggtccgcat tgtcgggctg    1080
acaatgttca gtgccgctac gacgcgagac tgctgtccat aaatcggaac cgcaagggcg    1140
tgcactccca gttcgtgttc ttccgaacta tagcaccaac cctgttcctt gatttcactc     1200
aaaaggcgca gaaagtcgat gttgttggta tacgtgtatt tcgtgagccg ttgcagaggg    1260
tactgattga gccactcttg ctgggcatgg tcatccaaat acgctaacag gattttgccc    1320
gctgacgttg catgcgctgg taagcgattc ccgagatgta agccatacgg gttaacgcga    1380 tcggttttgct gatgagcggc agaacgcgca atggtaatgg cttcatagcc atccaacacc   1440
atcacgctgt aaatcaggct ggtctgggtc gtaagcaagt tcagcagtgg ttgggaaatt    1500
ttcggcagtt gagcaccacc cagatatgag ccactgaatt tcaggatttt gggagttaag    1560
tagaagtagt gaccgtcgct ttccagatag cccagatact ccagagtaag cagatggcga    1620
cgagctgctg cacgtgtcat accggttttc tctgcggcca tggtgatatt gaggcgatga    1680
cgatctgtgc caaacgaatc cagaatcgcc atcccttgc taatgccggc tacaaaatct     1740
tcgtggcgga tgatcttctt gttggtgaa  ttgtgcagaa ttttctcctc tttcactttc    1800
ttgtcatcca tgttcgacca cattccagct actacatacg attgtcatat tgacatgtat    1860
aatataacgc ggaatgacta taactaaatc atgttttgtt cgattatcga acaaattatt    1920
taaatatcga acaaaaccta ctaaactact ctggaactga atcaaaaaat tataaaaaat    1980
gatcagacaa gggaattcta ctgaatgaca aaggaaatag tatttcatcc atataaattc    2040
acttccttaa acatgcttaa ttttccttcc tatcaaattt gctagatgca caaggagata    2100
tacatatggc tagcaaagga gaagaacttt tcacgggagt tgtcccaatt cttgttgaat    2160
tagatggtga tgttaatggg cacaaatttt ctgtccgtgg agagggtgaa ggtgatgcta    2220
caaacggaaa actcacccct taaatttatt tgcactactg gaaaactacc tgttccatggc   2280 caacacttgt cactactctg acctatggtg ttcaatgctt ttcccgttat ccggatcaca    2340
tgaaacggca tgacttttc aagagtgcca tgcccgaagg ttatgtacag gaacgcacta     2400
```

```
tatctttcaa agatgacggg acctacaaga cgcgtgctga agtcaagttt gaaggtgata    2460
cccttgttaa tcgtatcgag ttaaagggta ttgattttaa agaagatgga aacattcttg    2520
gacacaaact cgagtacaac tttaactcac acaatgtata catcacggca gacaaacaaa    2580
agaatggaat caaagctaac ttcaaaattc gccacaacgt tgaagatggt tccgttcaac    2640
tagcagacca ttatcaacaa atactccaa ttggcgatgg ccctgtcctt ttaccagaca    2700
accattacct gtcgacacaa tctgtccttt cgaaagatcc caacgaaaag cgtgaccaca    2760
tggtccttct tgagtttgta actgctgctg ggattacaca tggcatggat gagctctaca    2820
aaggtggcgg ttctgaattc acacctaggt aagatatcat tcaggacgag cctcagactc    2880
cagcgtaact ggactgaaaa caaactaaag cgcccttgtg gcgctttagt tttgttccgc    2940
ggccaccggc tggctcgctt cgctcggccc gtgacaacc ctgctggaca agctgatgga    3000
caggctgcgc ctgcccacga gcttgaccac agggattgcc caccggctac ccagccttcg    3060
accacatacc caccggctcc aactgcgcgg cctgcggcct tgccccatca atttttttaa    3120
ttttctctgg ggaaaagcct ccggcctgcg gcctgcgcgc ttcgcttgcc ggttggacac    3180
caagtggaag gcgggtcaag gctcgcgcag cgaccgcgca gcggcttggc cttgacgcgc    3240
ctggaacgac ccaagccatt gcgagtgggg gcagtcgaag gcgaagcccg cccgcctgcc    3300
ccccgagcct cacggcggcg agtgcggggg ttccaagggg gcagcgccac cttgggcaag    3360
gccgaaggcc gcgcagtcga tcaacaagcc cggagggge cacttttgc cggagggga    3420 gccgcgccga aggcgtgggg gaaccccgca ggggtgccct tctttgggca ccaaagaact    3480
agatataggc gaaatgcga aagacttaaa aatcaacaac ttaaaaaagg ggggtacgca    3540
acagctcatt gcggcacccc cgcaatagc tcattgcgta ggttaaagaa aatctgtaat    3600
tgactgccac ttttacgcaa cgcataattg ttgtcgcgct gccgaaagt tgcagctgat    3660 tgcgcatggt gccgcaaccg tgcggcaccc taccgcatgg agataagcat ggccacgcag    3720
tccagagaaa tcggcattca agccaagaac aagcccggtc actgggtgca aacgaacgc    3780 aaagcgcatg aggcgtgggc cgggcttatt gcgaggaaac ccacggcggc aatgctgctg    3840
catcacctcg tggcgcagat gggccaccag aacgccgtgg tggtcagcca gaagacactt    3900
tccaagctca tcggacgttc tttgcggacg gtccaatacg cagtcaagga cttggtggcc    3960
gagcgctgga tctccgtcgt gaagctcaac ggccccggca ccgtgtcggc ctacgtggtc    4020
aatgaccgcg tggcgtgggg ccagccccgc gaccagttgc gcctgtcggt gttcagtgcc    4080
gccgtggtgg ttgatcacga cgaccaggac gaatcgctgt ggggcatgg cgacctgcgc    4140 cgcatcccga ccctgtatcc gggcgagcag caactaccga ccggccccgg cgaggagccg    4200
cccagccagc ccggcattcc gggcatgaa ccagacctgc cagccttgac cgaaacggag    4260
gaatgggaac ggcgcgggca gcagcgcctg ccgatgcccg atgagccgtg ttttctggac    4320
gatggcgagc cgttggagcc gccgacacgg gtcacgctgc cgcgccggta g           4371
```

<210> SEQ ID NO 2
<211> LENGTH: 4370
<212> TYPE: DNA
<213> ORGANISM: Artificial Sequence
<220> FEATURE:
<223> OTHER INFORMATION: pPcaU1.1 plasmid

<400> SEQUENCE: 2

```
tacgtaagag gttccaactt tcaccataat gaaataagat cactaccggg cgtatttttt      60
gagttatcga gattttcagg agctaaggaa gctaaaatga gccatattca acgggaaacg     120
```

```
tcttgctcga ggccgcgatt aaattccaac atggatgctg atttatatgg gtataaatgg    180
gctcgcgata atgtcgggca atcaggtgcg acaatctatc gattgtatgg gaagcccgat    240
gcgccagagt tgtttctgaa acatggcaaa ggtagcgttg ccaatgatgt tacagatgag    300
atggtcaggc taaactggct gacggaattt atgcctcttc cgaccatcaa gcattttatc    360
cgtactcctg atgatgcatg gttactcacc actgcgatcc cagggaaaac agcattccag    420
gtattagaag aatatcctga ttcaggtgaa atattgttg atgcgctggc agtgttcctg     480
cgccggttgc attcgattcc tgtttgtaat tgtccttta acggcgatcg cgtatttcgt     540
ctcgctcagg cgcaatcacg aatgaataac ggtttggttg gtgcgagtga ttttgatgac    600
gagcgtaatg gctggcctgt tgaacaagtc tggaagaaa tgcataagct tttgccattc     660
tcaccggatt cagtcgtcac tcatggtgat ttctcacttg ataaccttat ttttgacgag    720
gggaaattaa taggttgtat tgatgttgga cgagtcggaa tcgcagaccg ataccaggat    780
cttgccatcc tatggaactg cctcggtgag ttttctcctt cattacagaa acggcttttt    840
caaaaatatg gtattgataa tcctgatatg aataaattgc agtttcactt gatgctcgat    900 gagttttct gagggcggat ccccctcaag tcaaaagcct ccggtcggag cttttgact     960 ttctgctatg gaggtcaggt atgatttac aggatattgc gcaattcacg cgcagtttcc    1020
tgcagtaacg gcagaatatg ctgaatcagg tattctttcg tggtccgcat tgtcgggctg    1080
acaatgttca gtgccgctac gacgcgagac tgctgtccat aaatcggaac cgcaagggcg    1140
tgcactccca gttcgtgttc ttccgaacta tagcaccaac cctgttcctt gatttcactc    1200
aaaaggcgca gaaagtcgat gttgttggta tacgtgtatt tcgtgagccg ttgcagaggg    1260
tactgattga gccactcttg ctgggcatgg tcatccaaat acgctaacag gattttgccc    1320
gctgacgttg catgcgctgg taagcgattc ccgagatgta agccatacgg gttaacgcga    1380 tcggttttgct gatgagcggc agaacgcgca atggtaatgg cttcatagcc atccaacacc    1440
atcacgctgt aaatcaggct ggtctgggtc gtaagcaagt tcagcagtgg ttgggaaatt    1500
ttcggcagtt gagcaccacc cagatatgag ccactgaatt tcaggatttt gggagttaag    1560
tagaagtagt gaccgtcgct ttccagatag cccagatact ccagagtaag cagatggcga    1620
cgagctgctg cacgtgtcat accggttttc tctgcggcca tggtgatatt gaggcgatga    1680
cgatctgtgc caaacgaatc cagaatcgcc atccctttgc taatgccggc tacaaaatct    1740
tcgtggcgga tgatcttctt gttggtggaa ttgtgcagaa ttttctcctc tttcactttc    1800
ttgtcatcca tgttcgacca cattccagct actacatacg attgtcatat tgacatgtat    1860
aatataacgc ggaatgacta taactaaatc atgttttgtt cgattatcga acaaattatt    1920
taaatatcga acaaaacctc taaactacta tggtactgaa tcaaaaaatt atacacaatg    1980
atcagacaag ggaattctac tgaatgacaa aggaaatagt atttcatcca tataaattca    2040
cttccttaaa catgcttaat tttccttcct atcaaatttg ctagatgcac aaggagatat    2100
acatatggct agcaaaggag aagaactttt cacgggagtt gtcccaattc ttgttgaatt    2160
agatggtgat gttaatgggc acaaattttc tgtccgtgga gagggtgaag gtgatgctac    2220
aaacggaaaa ctcacccctta aatttatttg cactactgga aaactacctg ttccatggcc    2280
aacacttgtc actactctga cctatggtgt tcaatgcttt tcccgttatc cggatcacat    2340
gaaacggcat gactttttca agagtgccat gcccgaaggt tatgtacagg aacgcactat    2400
atctttcaaa gatgacggga cctacaagac gcgtgctgaa gtcaagtttg aaggtgatac    2460
```

-continued

```
ccttgttaat cgtatcgagt taaagggtat tgattttaaa gaagatggaa acattcttgg    2520
acacaaactc gagtacaact ttaactcaca caatgtatac atcacggcag acaaacaaaa    2580
gaatggaatc aaagctaact tcaaaattcg ccacaacgtt gaagatggtt ccgttcaact    2640
agcagaccat tatcaacaaa atactccaat tggcgatggc cctgtccttt taccagacaa    2700
ccattacctg tcgacacaat ctgtcctttc gaaagatccc aacgaaaagc gtgaccacat    2760
ggtccttctt gagtttgtaa ctgctgctgg gattacacat ggcatggatg agctctacaa    2820
aggtggcggt tctgaattca cacctaggta agatatcatt caggacgagc ctcagactcc    2880
agcgtaactg gactgaaaac aaactaaagc gcccttgtgg cgctttagtt ttgttccgcg    2940
gccaccggct ggctcgcttc gctcggcccg tggacaaccc tgctggacaa gctgatggac    3000
aggctgcgcc tgcccacgag cttgaccaca gggattgccc accggctacc cagccttcga    3060
ccacataccc accggctcca actgcgcggc ctgcggcctt gccccatcaa ttttttaat    3120 tttctctggg gaaaagcctc cggcctgcgg cctgcgcgct tcgcttgccg gttggacacc    3180
aagtggaagg cgggtcaagg ctcgcgcagc gaccgcgcag cggcttggcc ttgacgcgcc    3240
tggaacgacc caagcctatg cgagtggggg cagtcgaagg cgaagcccgc ccgcctgccc    3300
cccgagcctc acgcggcgga gtgcgggggt tccaaggggg cagcgccacc ttgggcaagg    3360
ccgaaggccg cgcagtcgat caacaagccc cggaggggcc acttttttgcc ggaggggag    3420 ccgcgccgaa ggcgtggggg aaccccgcag gggtgcccct ctttgggcac caagaacta    3480 gatatagggc gaaatgcgaa agacttaaaa atcaacaact aaaaaaggg gggtacgcaa    3540 cagctcattg cggcaccccc cgcaatagct cattgcgtag gttaaagaaa atctgtaatt    3600
gactgccact tttacgcaac gcataattgt tgtcgcgctg ccgaaaagtt gcagctgatt    3660
gcgcatggtg ccgcaaccgt gcggcaccct accgcatgga gataagcatg ccacgcagt    3720 ccagagaaat cggcattcaa gccaagaaca agcccggtca ctgggtgcaa acggaacgca    3780
aagcgcatga ggcgtgggcc gggcttattg cgaggaaacc cacggcggca atgctgctgc    3840
atcacctcgt ggcgcagatg ggccaccaga acgccgtggt ggtcagccag aagacacttt    3900
ccaagctcat cggacgttct ttgcggacgg tccaatacgc agtcaaggac ttggtggccg    3960
agcgctggat ctccgtcgtg aagctcaacg gccccggcac cgtgtcggcc tacgtggtca    4020
atgaccgcgt ggcgtgggc cagccccgcg accagttgcg cctgtcggtg ttcagtgccg    4080
ccgtggtggt tgatcacgac gaccaggacg aatcgctgtt ggggcatggc gacctgcgcc    4140
gcatcccgac cctgtatccg ggcgagcagc aactaccgac cggccccggc gaggagccgc    4200
ccagccagcc cggcattccg ggcatggaac cagacctgcc agccttgacc gaaacggagg    4260
aatgggaacg gcgcgggcag cagcgcctgc cgatgcccga tgagccgtgt tttctggacg    4320
atggcgagcc gttggagccg ccgacacggg tcacgctgcc gcgccggtag          4370
```

<210> SEQ ID NO 3
<211> LENGTH: 4370
<212> TYPE: DNA
<213> ORGANISM: Artificial Sequence
<220> FEATURE:
<223> OTHER INFORMATION: pPcaU1.2 plasmid

<400> SEQUENCE: 3

```
tacgtaagag gttccaactt tcaccataat gaaataagat cactaccggg cgtatttttt      60
gagttatcga gattttcagg agctaaggaa gctaaaatga gccatattca acggaaacg      120 tcttgctcga ggccgcgatt aaattccaac atggatgctg atttatatgg gtataaatgg      180
```

```
gctcgcgata atgtcgggca atcaggtgcg acaatctatc gattgtatgg gaagcccgat    240
gcgccagagt tgtttctgaa acatggcaaa ggtagcgttg ccaatgatgt tacagatgag    300
atggtcaggc taaactggct gacggaattt atgcctcttc cgaccatcaa gcattttatc    360
cgtactcctg atgatgcatg gttactcacc actgcgatcc cagggaaaac agcattccag    420
gtattagaag aatatcctga ttcaggtgaa aatattgttg atgcgctggc agtgttcctg    480
cgccggttgc attcgattcc tgtttgtaat tgtccttttta acggcgatcg cgtatttcgt    540
ctcgctcagg cgcaatcacg aatgaataac ggtttggttg gtgcgagtga ttttgatgac    600
gagcgtaatg gctggcctgt tgaacaagtc tggaaagaaa tgcataagct tttgccattc    660
tcaccggatt cagtcgtcac tcatggtgat ttctcacttg ataaccttat ttttgacgag    720
gggaaattaa taggttgtat tgatgttgga cgagtcggaa tcgcagaccg ataccaggat    780
cttgccatcc tatggaactg cctcggtgag ttttctcctt cattacagaa acggcttttt    840
caaaaatatg gtattgataa tcctgatatg aataaattgc agtttcactt gatgctcgat    900 gagttttttct gagggcggat cccccctcaag tcaaaagcct ccggtcggag cttttgact    960 ttctgctatg gaggtcaggt atgatttttac aggatattgc gcaattcacg cgcagttttcc   1020 tgcagtaacg gcagaatatg ctgaatcagg tattctttcg tggtccgcat tgtcgggctg   1080
acaatgttca gtgccgctac gacgcgagac tgctgtccat aaatcggaac cgcaagggcg   1140
tgcactccca gttcgtgttc ttccgaacta tagcaccaac cctgttcctt gatttcactc   1200
aaaaggcgca gaaagtcgat gttgttggta tacgtgtatt tcgtgagccg ttgcagaggg   1260
tactgattga gccactcttg ctgggcatgg tcatccaaat acgctaacag gattttgccc   1320
gctgacgttg catgcgctgg taagcgattc ccgagatgta agccatacgg gttaacgcga   1380
taaccttgct gatgagcggc agaacgcgca atggtaatgg cttcatagcc atccaacacc   1440
atcacgctgt aaatcaggct ggtctgggtc gtaagcaagt tcagcagtgg ttgggaaatt   1500 tcggcagtt gagcaccacc cagatatgag ccactgaatt tcaggatttt gggagttaag   1560
tagaagtagt gaccgtcgct ttccagatag cccagatact ccagagtaag cagatggcga   1620
cgagctgctg cacgtgtcat accggttttc tctgcggcca tggtgatatt gaggcgatga   1680
cgatctgtgc caaacgaatc cagaatcgcc atccctttgc taatgccggc tacaaaatct   1740
tcgtggcgga tgatcttctt gttggtggaa ttgtgcagaa ttttctcctc tttcactttc   1800
ttgtcatcca tgttcgacca cattccagct actacatacg attgtcatat tgacatgtat   1860
aatataacgc ggaatgacta taactaaatc atgttttgtt cgattatcga acaaattatt   1920
taaatatcga acaaaacctc taaactacta tggtactgaa tcaaaaaatt atacacaatg   1980
atcagacaag ggaattctac tgaatgacaa aggaaatagt atttcatcca tataaattca   2040
cttccttaaa catgcttaat tttccttcct atcaaatttg ctagatgcac aaggagatat   2100
acatatggct agcaaaggag aagaactttt cacgggagtt gtcccaattc ttgttgaatt   2160
agatggtgat gttaatgggc acaaattttc tgtccgtgga gagggtgaag gtgatgctac   2220
aaacggaaaa ctcacccctta aatttatttg cactactgga aaactacctg ttccatggcc   2280
aacacttgtc actactctga cctatggtgt tcaatgcttt tcccgttatc cggatcacat   2340
gaaacggcat gacttttttca agagtgccat gcccgaaggt tatgtacagg aacgcactat   2400
atctttcaaa gatgacggga cctacaagac gcgtgctgaa gtcaagtttg aaggtgatac   2460
ccttgttaat cgtatcgagt taaagggtat tgattttaaa gaagatggaa acattcttgg   2520
```

| | |
|---|---|
| acacaaactc gagtacaact ttaactcaca caatgtatac atcacggcag acaaacaaaa | 2580 |
| gaatggaatc aaagctaact tcaaaattcg ccacaacgtt gaagatggtt ccgttcaact | 2640 |
| agcagaccat tatcaacaaa atactccaat tggcgatggc cctgtccttt taccagacaa | 2700 |
| ccattacctg tcgacacaat ctgtcctttc gaaagatccc aacgaaaagc gtgaccacat | 2760 |
| ggtccttctt gagtttgtaa ctgctgctgg gattacacat ggcatggatg agctctacaa | 2820 |
| aggtggcggt tctgaattca cacctaggta agatatcatt caggacgagc ctcagactcc | 2880 |
| agcgtaactg gactgaaaac aaactaaagc gcccttgtgg cgctttagtt ttgttccgcg | 2940 |
| gccaccggct ggctcgcttc gctcggcccg tggacaaccc tgctggacaa gctgatggac | 3000 |
| aggctgcgcc tgcccacgag cttgaccaca gggattgccc accggctacc cagccttcga | 3060 |
| ccacataccc accggctcca actgcgcggc ctgcggcctt gccccatcaa tttttttaat | 3120 |
| tttctctggg gaaaagcctc cggcctgcgg cctgcgcgct tcgcttgccg gttggacacc | 3180 |
| aagtggaagg cgggtcaagg ctcgcgcagc gaccgcgcag cggcttggcc ttgacgcgcc | 3240 |
| tggaacgacc caagcctatg cgagtggggg cagtcgaagg cgaagcccgc ccgcctgccc | 3300 |
| cccgagcctc acggcggcga gtgcgggggt tccaaggggg cagcgccacc ttgggcaagg | 3360 |
| ccgaaggccg cgcagtcgat caacaagccc cggaggggcc acttttttgcc ggaggggggag | 3420 |
| ccgcgccgaa ggcgtggggg aaccccgcag gggtgcccctt ctttgggcac caagaactaa | 3480 |
| gatatagggc gaaatgcgaa agacttaaaa atcaacaact taaaaaaggg gggtacgcaa | 3540 |
| cagctcattg cggcaccccc cgcaatagct cattgcgtag gttaaagaaa atctgtaatt | 3600 |
| gactgccact tttacgcaac gcataattgt tgtcgcgctg ccgaaaagtt gcagctgatt | 3660 |
| gcgcatggtg ccgcaaccgt gcggcaccct accgcatgga gataagcatg gccacgcagt | 3720 |
| ccagagaaat cggcattcaa gccaagaaca agcccggtca ctgggtgcaa acggaacgca | 3780 |
| aagcgcatga ggcgtgggcc gggcttattg cgaggaaacc cacggcggca atgctgctgc | 3840 |
| atcacctcgt ggcgcagatg ggccaccaga acgccgtggt ggtcagccag aagacacttt | 3900 |
| ccaagctcat cggacgttct ttgcggacgg tccaatacgc agtcaaggac ttggtggccg | 3960 |
| agcgctggat ctccgtcgtg aagctcaacg gccccgcac cgtgtcggcc tacgtggtca | 4020 |
| atgaccgcgt ggcgtggggc cagccccgcg accagttgcg cctgtcggtg ttcagtgccg | 4080 |
| ccgtggtggt tgatcacgac gaccaggacg aatcgctgtt ggggcatggc gacctgcgcc | 4140 |
| gcatcccgac cctgtatccg ggcgagcagc aactaccgac cggccccggc gaggagccgc | 4200 |
| ccagccagcc cggcattccg ggcatggaac cagacctgcc agccttgacc gaaacggagg | 4260 |
| aatgggaacg gcgcgggcag cagcgcctgc cgatgcccga tgagccgtgt tttctggacg | 4320 |
| atggcgagcc gttggagccg ccgacacggg tcacgctgcc gcgccggtag | 4370 |

<210> SEQ ID NO 4
<211> LENGTH: 837
<212> TYPE: DNA
<213> ORGANISM: Artificial Sequence
<220> FEATURE:
<223> OTHER INFORMATION: PcaU1.2 (modified PcaU)

<400> SEQUENCE: 4

| | |
|---|---|
| atgtggtcga acatggatga caagaaagtg aaagaggaga aaattctgca caattccacc | 60 |
| aacaagaaga tcatccgcca cgaagatttt gtagccggca ttagcaaagg gatggcgatt | 120 |
| ctggattcgt ttggcacaga tcgtcatcgc ctcaatatca ccatgccgcc agagaaaacc | 180 |
| ggtatgacac gtgcagcagc tcgtcgccat ctgcttactc tggagtatct gggctatctg | 240 |

```
gaaagcgacg gtcactactt ctacttaact cccaaaatcc tgaaattcag tggctcatat    300
ctgggtggtg ctcaactgcc gaaaatttcc caaccactgc tgaacttgct tacgacccag    360
accagcctga tttacagcgt gatggtgttg gatggctatg aagccattac cattgcgcgt    420
tctgccgctc atcagcaagg ttatcgcgtt aacccgtatg gcttacatct cgggaatcgc    480
ttaccagcgc atgcaacgtc agcgggcaaa atcctgttag cgtatttgga tgaccatgcc    540
cagcaagagt ggctcaatca gtaccctctg caacggctca cgaaatacac gtataccaac    600
aacatcgact ttctgcgcct tttgagtgaa atcaaggaac agggttggtg ctatagttcg    660
gaagaacacg aactgggagt gcacgccctt gcggttccga tttatggaca gcagtctcgc    720
gtcgtagcgg cactgaacat tgtcagcccg acaatgcgga ccacgaaaga atacctgatt    780
cagcatattc tgccgttact gcaggaaact gcgcgtgaat tgcgcaatat cctgtaa      837

<210> SEQ ID NO 5
<211> LENGTH: 278
<212> TYPE: PRT
<213> ORGANISM: Artificial Sequence
<220> FEATURE:
<223> OTHER INFORMATION: PcaU1.2 (modified PcaU)

<400> SEQUENCE: 5

Met Trp Ser Asn Met Asp Asp Lys Lys Val Lys Glu Glu Lys Ile Leu
1               5                   10                  15

His Asn Ser Thr Asn Lys Lys Ile Ile Arg His Glu Asp Phe Val Ala
            20                  25                  30

Gly Ile Ser Lys Gly Met Ala Ile Leu Asp Ser Phe Gly Thr Asp Arg
        35                  40                  45

His Arg Leu Asn Ile Thr Met Ala Ala Glu Lys Thr Gly Met Thr Arg
    50                  55                  60

Ala Ala Ala Arg Arg His Leu Leu Thr Leu Glu Tyr Leu Gly Tyr Leu
65                  70                  75                  80

Glu Ser Asp Gly His Tyr Phe Tyr Leu Thr Pro Lys Ile Leu Lys Phe
                85                  90                  95

Ser Gly Ser Tyr Leu Gly Gly Ala Gln Leu Pro Lys Ile Ser Gln Pro
            100                 105                 110

Leu Leu Asn Leu Leu Thr Thr Gln Thr Ser Leu Ile Tyr Ser Val Met
        115                 120                 125

Val Leu Asp Gly Tyr Glu Ala Ile Thr Ile Ala Arg Ser Ala Ala His
    130                 135                 140

Gln Gln Gly Tyr Arg Val Asn Pro Tyr Gly Leu His Leu Gly Asn Arg
145                 150                 155                 160

Leu Pro Ala His Ala Thr Ser Ala Gly Lys Ile Leu Leu Ala Tyr Leu
                165                 170                 175

Asp Asp His Ala Gln Gln Glu Trp Leu Asn Gln Tyr Pro Leu Gln Arg
            180                 185                 190

Leu Thr Lys Tyr Thr Tyr Thr Asn Asn Ile Asp Phe Leu Arg Leu Leu
        195                 200                 205

Ser Glu Ile Lys Glu Gln Gly Trp Cys Tyr Ser Ser Glu Glu His Glu
    210                 215                 220

Leu Gly Val His Ala Leu Ala Val Pro Ile Tyr Gly Gln Gln Ser Arg
225                 230                 235                 240

Val Val Ala Ala Leu Asn Ile Val Ser Pro Thr Met Arg Thr Thr Lys
                245                 250                 255
```

Glu Tyr Leu Ile Gln His Ile Leu Pro Leu Leu Gln Glu Thr Ala Arg
                260                 265                 270

Glu Leu Arg Asn Ile Leu
        275

<210> SEQ ID NO 6
<211> LENGTH: 4201
<212> TYPE: DNA
<213> ORGANISM: Artificial Sequence
<220> FEATURE:
<223> OTHER INFORMATION: pBTL2_PobR-DM plasmid

<400> SEQUENCE: 6

| | | |
|---|---|---|
| tacgtaagag gttccaactt tcaccataat gaaataagat cactaccggg cgtatttttt | 60 |
| gagttatcga gattttcagg agctaaggaa gctaaaatga gccatattca acgggaaacg | 120 |
| tcttgctcga ggccgcgatt aaattccaac atggatgctg atttatatgg gtataaatgg | 180 |
| gctcgcgata atgtcgggca atcaggtgcg acaatctatc gattgtatgg gaagcccgat | 240 |
| gcgccagagt tgtttctgaa acatggcaaa ggtagcgttg ccaatgatgt tacagatgag | 300 |
| atggtcaggc taaactggct gacggaattt atgcctcttc cgaccatcaa gcattttatc | 360 |
| cgtactcctg atgatgcatg gttactcacc actgcgatcc cagggaaaac agcattccag | 420 |
| gtattagaag aatatcctga ttcaggtgaa atattgttg atgcgctggc agtgttcctg | 480 |
| cgccggttgc attcgattcc tgtttgtaat tgtcctttta acggcgatcg cgtatttcgt | 540 |
| ctcgctcagg cgcaatcacg aatgaataac ggtttggttg gtgcgagtga ttttgatgac | 600 |
| gagcgtaatg gctggcctgt tgaacaagtc tggaaagaaa tgcataagct tttgccattc | 660 |
| tcaccggatt cagtcgtcac tcatggtgat ttctcacttg ataaccttat ttttgacgag | 720 |
| gggaaattaa taggttgtat tgatgttgga cgagtcggaa tcgcagaccg ataccaggat | 780 |
| cttgccatcc tatggaactg cctcggtgag ttttctcctt cattacagaa acggcttttt | 840 |
| caaaaatatg gtattgataa tcctgatatg aataaattgc agtttcactt gatgctcgat | 900 |
| gagtttttct gagggcggat cccctcaag tcaaaagcct ccggtcggag cttttgact | 960 |
| ttctgctatg gaggtcaggt atgattttat accagattgc gcagttcgtt ggcagtgttg | 1020 |
| cgcagcaacg gtaacacctg gtcgatgagg tactggggtt gaacccgatt agtctgggac | 1080 |
| atgcagttca gggctgcaat cgtcagccct gtgcgttga ggactggaac cgcaatggca | 1140 |
| atcacaccga gctcatgttc ttccgtggat aagcagtaat ccgactgacg aacggcatcc | 1200 |
| agggtttcaa gaaaggtgtg ttcatcggtg atggtatacg cgtcaggcg tttcaggcca | 1260 |
| tacttctcga tccactcgat ctgtacttcg cgatcaagca cgctaagaag cactttaccg | 1320 |
| gttgaggtag catgcgcagg cagacgattc cctaagtgca tgccatacgg actgacgcgg | 1380 |
| ttgtcttgct gaggcagata ggaacgggcg actggaacca cctcgtgttc atccaggacc | 1440 |
| acaatgctaa acgtcagact cgtctgcgca cacagcagat tgaggaaaga ttgggccact | 1500 |
| tcggcaaat gcgctgaact cagatagctc gaagagaagc gcaaacacg atgggttaac | 1560 |
| cagaagtagt gttcgtcagt atccaggtaa cccagaaact tcagggtttt cagatagcga | 1620 |
| cgagctgctg tacggctaat gccggtgcgt tcagctacct gtgtcacgtt taagcgctgc | 1680 |
| cgatcaatgc caaacgcttc cagtaacgcc agacctttg ccagtcccgc gatgtagtcc | 1740 |
| tctgtacgaa tctcttcgct cgaatgcgga tgcgccaaat actgatggtg ttgttccata | 1800 |
| acattcaaat ccaaaatggt tttgtccgat catcggacag ttgtaatgct aatcggataa | 1860 |
| ttttgagcct tgattataga tgtcttttta atgaggcggt actttaaaaa tagaaaatag | 1920 |

-continued

```
caaggagata tacatatggc tagcaaagga gaagaacttt tcacgggagt tgtcccaatt    1980
cttgttgaat tagatggtga tgttaatggg cacaaatttt ctgtccgtgg agagggtgaa    2040
ggtgatgcta caaacggaaa actcacccct aaatttattt gcactactgg aaaactacct    2100
gttccatggc caacacttgt cactactctg acctatggtg ttcaatgctt ttcccgttat    2160
ccggatcaca tgaaacggca tgactttttc aagagtgcca tgcccgaagg ttatgtacag    2220
gaacgcacta tatctttcaa agatgacggg acctacaaga cgcgtgctga agtcaagttt    2280
gaaggtgata cccttgttaa tcgtatcgag ttaaagggta ttgattttaa agaagatgga    2340
aacattcttg gacacaaact cgagtacaac tttaactcac acaatgtata catcacggca    2400
gacaaacaaa agaatggaat caaagctaac ttcaaaattc gccacaacgt tgaagatggt    2460
tccgttcaac tagcagacca ttatcaacaa atactccaa ttggcgatgg ccctgtcctt    2520
ttaccagaca accattacct gtcgacacaa tctgtccttt cgaaagatcc aacgaaaag    2580
cgtgaccaca tggtccttct tgagtttgta actgctgctg ggattacaca tggcatggat    2640
gagctctaca aggtggcggt tctgaattc acacctaggt aagatatcat tcaggacgag    2700
cctcagactc cagcgtaact ggactgaaaa caaactaaag cgcccttgtg gcgctttagt    2760
tttgttccgc ggccaccggc tggctcgctt cgctcggccc gtggacaacc ctgctggaca    2820
agctgatgga caggctgcgc ctgcccacga gcttgaccac agggattgcc caccggctac    2880
ccagccttcg accacatacc caccggctcc aactgcgcgg cctgcggcct tgccccatca    2940
atttttttaa ttttctctgg ggaaaagcct ccggcctgcg gcctgcgcgc ttcgcttgcc    3000
ggttggacac caagtggaag gcgggtcaag gctcgcgcag cgaccgcgca gcggcttggc    3060
cttgacgcgc ctggaacgac ccaagcctat gcgagtgggg gcagtcgaag gcgaagcccg    3120
cccgcctgcc ccccgagcct cacggcggcg agtgcggggg ttccaagggg gcagcgccac    3180
cttgggcaag gccgaaggcc gcgcagtcga tcaacaagcc ccggagggggc cacttttgc    3240
cggaggggga gccgcgccga aggcgtgggg gaaccccgca ggggtgccct tctttgggca    3300
ccaaagaact agatataggg cgaaatgcga aagacttaaa aatcaacaac ttaaaaaagg    3360
ggggtacgca acagctcatt gcggcacccc ccgcaatagc tcattgcgta ggttaaagaa    3420
aatctgtaat tgactgccac ttttacgcaa cgcataattg ttgtcgcgct gccgaaaagt    3480
tgcagctgat tgcgcatggt gccgcaaccg tgcggcaccc taccgcatgg agataagcat    3540
ggccacgcag tccagagaaa tcggcattca agccaagaac aagcccggtc actgggtgca    3600
aacgaacgc aaagcgcatg aggcgtgggc cgggcttatt gcgaggaaac ccacggcggc    3660
aatgctgctg catcaccctcg tggcgcagat gggccaccag aacgccgtgg tggtcagcca    3720
gaagacactt tccaagctca tcggacgttc tttgcggacg gtccaatacg cagtcaagga    3780
cttggtggcc gagcgctgga tctccgtcgt gaagctcaac ggccccggca ccgtgtcggc    3840
ctacgtggtc aatgaccgcg tggcgtgggg ccagccccgc gaccagttgc gcctgtcggt    3900
gttcagtgcc gccgtggtgg ttgatcacga cgaccaggac gaatcgctgt ggggcatgg    3960
cgacctgcgc cgcatcccga ccctgtatcc gggcgagcag caactaccga ccggccccgg    4020
cgaggagccg cccagccagc ccggcattcc gggcatggaa ccagacctgc cagccttgac    4080
cgaaacggag gaatgggaac ggcgcgggca gcagcgcctg ccgatgcccg atgagccgtg    4140
ttttctggac gatggcgagc cgttggagcc gccgacacgg gtcacgctgc cgcgccggta    4200
g                                                                   4201
```

<210> SEQ ID NO 7
<211> LENGTH: 4287
<212> TYPE: DNA
<213> ORGANISM: Artificial Sequence
<220> FEATURE:
<223> OTHER INFORMATION: pBTL2_CatM-C2 plasmid

<400> SEQUENCE: 7

| | | | | | |
|---|---|---|---|---|---|
| tacgtaagag | gttccaactt | tcaccataat | gaaataagat | cactaccggg | cgtattttt | 60 |
| gagttatcga | gattttcagg | agctaaggaa | gctaaaatga | gccatattca | acgggaaacg | 120 |
| tcttgctcga | ggccgcgatt | aaattccaac | atggatgctg | atttatatgg | gtataaatgg | 180 |
| gctcgcgata | atgtcgggca | atcaggtgcg | acaatctatc | gattgtatgg | gaagcccgat | 240 |
| gcgccagagt | tgtttctgaa | acatggcaaa | ggtagcgttg | ccaatgatgt | tacagatgag | 300 |
| atggtcaggc | taaactggct | gacggaattt | atgcctcttc | cgaccatcaa | gcattttatc | 360 |
| cgtactcctg | atgatgcatg | gttactcacc | actgcgatcc | cagggaaaac | agcattccag | 420 |
| gtattagaag | aatatcctga | ttcaggtgaa | aatattgttg | atgcgctggc | agtgttcctg | 480 |
| cgccggttgc | attcgattcc | tgtttgtaat | tgtccttta | acggcgatcg | cgtatttcgt | 540 |
| ctcgctcagg | cgcaatcacg | aatgaataac | ggtttggttg | gtgcgagtga | ttttgatgac | 600 |
| gagcgtaatg | gctggcctgt | tgaacaagtc | tggaaagaaa | tgcataagct | tttgccattc | 660 |
| tcaccggatt | cagtcgtcac | tcatggtgat | ttctcacttg | ataaccttat | ttttgacgag | 720 |
| gggaaattaa | taggttgtat | tgatgttgga | cgagtcggaa | tcgcagaccg | ataccaggat | 780 |
| cttgccatcc | tatggaactg | cctcggtgag | ttttctcctt | cattacagaa | acggcttttt | 840 |
| caaaaatatg | gtattgataa | tcctgatatg | aataaattgc | agtttcactt | gatgctcgat | 900 |
| gagtttttct | gagggcggat | ccccctcaag | tcaaaagcct | ccggtcggag | gcttttgact | 960 |
| ttctgctatg | gaggtcaggt | atgattttat | tcgatgagtg | gcctgatatg | gtgcgttgca | 1020 |
| aacacctcct | gtacacaggc | gagaatttta | ggaatgtaat | tactgtggtc | catatttcgc | 1080 |
| accgcgagtg | aaattgggct | ataggcatca | tcatctaaaa | ttggaatata | agtagattc | 1140 |
| ttcaccccaa | tatccatggc | agacgccggt | acgatgcaga | cgccttcacc | tgctgccacc | 1200 |
| aagccgagtg | ccagttgaat | ttctcgaatt | tcggtgagtt | tggatggtac | taggcctagt | 1260 |
| tcggtaaaga | gtgactgaat | aaaggtcgca | aaattgggct | tttgagagac | tgggtacagc | 1320 |
| agcatcggtt | catcaataat | ttgagagaga | tgaaccctg | ttgctgcaaa | ctgattgagg | 1380 |
| tgatgatgct | tatggattgc | aagtttgagc | tgttctttat | gcaacacgat | acgtcgaatt | 1440 |
| gcaggatcgg | taattttgag | ccgaccaaaa | cccagatcga | ttttttccctg | cttaagggca | 1500 |
| ttaatttgat | ctttggtgcc | gcattcgatg | agttcgatgt | gaattttcagg | attttgttga | 1560 |
| cgaaacagat | aaataattc | aggtaacaaa | ccatacagta | aggagctgac | gtaaccaatt | 1620 |
| ctcaaggttt | gactgaccgt | tgcaatccgt | tttgccattg | aggacgcttg | tgcagtatga | 1680 |
| gtcaaaatct | gcacagcatg | ctgataaaaa | aacatgcctg | cttcagtcac | tttagccggt | 1740 |
| ctgaagccgc | gttcaaatag | ctgaattccc | aattcttctt | cgagtttttg | aatttgtcgg | 1800 |
| ctgaggggcg | gctgggcaat | acacaacttt | tcagcagctt | tggaaatgct | ttgctcttca | 1860 |
| accacggtca | caaaatatct | gaggtgtctt | agttccattt | atacgcccta | attggtttta | 1920 |
| tatacctttt | tagtatgcaa | aaataccaaa | ttggtgttgg | ttttattat | tacattaatt | 1980 |
| taaggtatgt | aaatagtatt | tattgaaaag | gagatggacc | gatggctagc | aaaggagaag | 2040 |
| aactttttcac | gggagttgtc | ccaattcttg | ttgaattaga | tggtgatgtt | aatgggcaca | 2100 |

```
aattttctgt ccgtggagag ggtgaaggtg atgctacaaa cggaaaactc acccttaaat    2160
ttatttgcac tactggaaaa ctacctgttc catggccaac acttgtcact actctgacct    2220
atggtgttca atgcttttcc cgttatccgg atcacatgaa acggcatgac tttttcaaga    2280
gtgccatgcc cgaaggttat gtacaggaac gcactatatc tttcaaagat gacgggacct    2340
acaagacgcg tgctgaagtc aagtttgaag gtgataccct tgttaatcgt atcgagttaa    2400
agggtattga ttttaaagaa gatggaaaca ttcttggaca caaactcgag tacaactttta   2460 actcacacaa tgtatacatc acggcagaca acaaaagaa tggaatcaaa gctaacttca    2520
aaattcgcca aacgttgaa gatggttccg ttcaactagc agaccattat caacaaaata    2580
ctccaattgg cgatggccct gtccttttac cagacaacca ttacctgtcg acacaatctg    2640
tcctttcgaa agatcccaac gaaaagcgtg accacatggt ccttcttgag tttgtaactg    2700
ctgctgggat tacacatggc atggatgagc tctacaaagg tggcggttct gaattcacac    2760
ctaggtaaga tatcattcag gacgagcctc agactccagc gtaactggac tgaaaacaaa    2820
ctaaagcgcc cttgtggcgc tttagttttg ttccgcggcc accggctggc tcgcttcgct    2880
cggcccgtgg acaaccctgc tggacaagct gatggacagg ctgcgcctgc ccacgagctt    2940
gaccacaggg attgcccacc ggctacccag ccttcgacca catacccacc ggctccaact    3000
gcgcggcctg cggccttgcc ccatcaattt ttttaattt ctctggggaa agcctccgg    3060 cctgcggcct gcgcgcttcg cttgccggtt ggacaccaag tggaaggcgg gtcaaggctc    3120
gcgcagcgac cgcgcagcgg cttggccttg acgcgcctgg aacgacccaa gcctatgcga    3180
gtgggggcag tcgaaggcga agcccgcccg cctgccccc gagcctcacg gcggcgagtg    3240
cgggggttcc aagggggcag cgccaccttg ggcaaggccg aaggccgcgc agtcgatcaa    3300
caagccccgg aggggccact ttttgccgga gggggagccg cgccgaaggc gtgggggaac    3360
cccgcagggg tgcccttctt tgggcaccaa agaactagat ataggcgaa atgcgaaaga    3420 cttaaaaatc aacaacttaa aaaaggggggg tacgcaacag ctcattgcgg cacccccgc    3480 aatagctcat tgcgtaggtt aaagaaaatc tgtaattgac tgccactttt acgcaacgca    3540
taattgttgt cgcgctgccg aaaagttgca gctgattgcg catggtgccg caaccgtgcg    3600
gcaccctacc gcatggagat aagcatggcc acgcagtcca gagaaatcgg cattcaagcc    3660
aagaacaagc ccggtcactg ggtgcaaacg gaacgcaaag cgcatgaggc gtgggccggg    3720
cttattgcga ggaaacccac ggcggcaatg ctgctgcatc acctcgtggc gcagatgggc    3780
caccagaacg ccgtggtggt cagccagaag acactttcca agctcatcgg acgttctttg    3840
cggacggtcc aatacgcagt caaggacttg gtggccgagc gctggatctc cgtcgtgaag    3900
ctcaacggcc ccgcaccgt gtcggcctac gtggtcaatg accgcgtggc gtggggccag    3960
ccccgcgacc agttgcgcct gtcggtgttc agtgccgccg tggtggttga tcacgacgac    4020
caggacgaat cgctgtttggg gcatggcgac ctgcgccgca tcccgaccct gtatccgggc    4080
gagcagcaac taccgaccgg ccccggcgag gagccgccca gccagcccgg cattccgggc    4140
atggaaccag acctgccagc cttgaccgaa acggaggaat gggaacggcg cgggcagcag    4200
cgcctgccga tgcccgatga gccgtgtttt ctggacgatg gcgagccgtt ggagccgccg    4260
acacgggtca cgctgccgcg ccggtag                                       4287
```

<210> SEQ ID NO 8
<211> LENGTH: 225
<212> TYPE: DNA

```
<213> ORGANISM: Artificial Sequence
<220> FEATURE:
<223> OTHER INFORMATION: PcaR promoter

<400> SEQUENCE: 8
agcattcaac tgaaatgagg caaatagcct ccagaactgc tcgcagatcg cacaacagtt      60
cgataatcgc acaaattcag ccaaaccctc tctactgttg ccctatcttg cggcacgcta     120
tagcgaaagt cagcaagcca tttcaagtgc tgacaggccc catcgcttca cgcgctccgg     180
ccagcccgac aaccacaact ccaggaacaa caaggagata tacat                     225

<210> SEQ ID NO 9
<211> LENGTH: 874
<212> TYPE: DNA
<213> ORGANISM: Artificial Sequence
<220> FEATURE:
<223> OTHER INFORMATION: TphR based TPA sensor

<400> SEQUENCE: 9
caacccctgc ggatatagct tttttccaa ctcattgcga gcgcgcttca gcggtatcaa       60
aaaagtctcc ttgaactcac tcatgctgag tctctctgcc ctaacagcaa tgctcatggc    120
agcaattgtg ttgccttgag ggtcgcgcac tggcgctgcc atagagcgca cccccagctc    180
cagctctccg tcgctgcatg accaccctga ttgccggcaa gtttcaagca gacctagcag    240
ctcctccaag tcagtcaccg tatgaggggt cagtgccacc cgctcgatca tctctagcct    300
tgcacgcgcc tcctgttggg ggagtcctga caacagcatc cgaccaatcg cagagcagta    360
caccggcaac ctagatccta ttcctaggcc cgtgctcaag ctgcgccgtg cggtcgaacg    420
accaatgatg atggcatcgt cctccaacaa agtaccaagc gaagcggatt ctctggtgcg    480
ctccgacagt gcatccagta gtggctgggc aatgcaggc atggggcgcg atgacagaaa    540
tgaataggcg atcagcagcg atttgggctg catccagaac agtttgccgt cgctctctag    600
atagccaagc tgtaccagtg tgctgagcga acgtctggcg gatgctggcg tggactgcgt    660
gagcctggct acctctgaca gcgtcagccg ggtatgccga cggtcaaagc aagtcagtac    720
ccccaatccc ttgcgcagcg attccacaaa gttcttgtcc tgcatagcga tcaaatcaag    780
gtgttttcaa cattttttgcg catagcgcaa aaacaggttt aacacaaagt acgacatcct    840
catactgcag ttccccacac aagaaggaga caag                                874

<210> SEQ ID NO 10
<211> LENGTH: 282
<212> TYPE: DNA
<213> ORGANISM: Artificial Sequence
<220> FEATURE:
<223> OTHER INFORMATION: PcaU1 promoter region

<400> SEQUENCE: 10
tccagctact acatacgatt gtcatattga catgtataat ataacgcgga atgactataa     60
ctaaatcatg ttttgttcga ttatcgaaca aattatttaa atatcgaaca aaacctacta    120
aactactctg gaactgaatc aaaaaattat aaaaaatgat cagacaaggg aattctactg    180
aatgacaaag gaaatagtat ttcatccata taaattcact tccttaaaca tgcttaattt    240
tccttcctat caaatttgct agatgcacaa ggagatatac at                       282

<210> SEQ ID NO 11
<211> LENGTH: 281
<212> TYPE: DNA
<213> ORGANISM: Artificial Sequence
```

```
<220> FEATURE:
<223> OTHER INFORMATION: PcaU1.1 promoter region

<400> SEQUENCE: 11
tccagctact acatacgatt gtcatattga catgtataat ataacgcgga atgactataa    60
ctaaatcatg ttttgttcga ttatcgaaca aattatttaa atatcgaaca aaacctctaa   120
actactatgg tactgaatca aaaaattata cacaatgatc agacaaggga attctactga   180
atgacaaagg aaatagtatt tcatccatat aaattcactt ccttaaacat gcttaatttt   240
ccttcctatc aaatttgcta gatgcacaag gagatataca t                       281

<210> SEQ ID NO 12
<211> LENGTH: 123
<212> TYPE: DNA
<213> ORGANISM: Artificial Sequence
<220> FEATURE:
<223> OTHER INFORMATION: CatM C2 promoter

<400> SEQUENCE: 12
ttatacgccc taattggttt tatatacctt tttagtatgc aaaaatacca aattggtgtt    60
ggtttttatt attacattaa tttaaggtat gtaaatagta tttattgaaa aggagatgga   120
ccg                                                                 123

<210> SEQ ID NO 13
<211> LENGTH: 123
<212> TYPE: DNA
<213> ORGANISM: Artificial Sequence
<220> FEATURE:
<223> OTHER INFORMATION: CatM C2 promoter reverse complement

<400> SEQUENCE: 13
cggtccatct cctttcaat aaatactatt tacataccttt aaattaatgt aataataaaa    60
accaacacca atttggtatt tttgcatact aaaaaggtat ataaaaccaa ttagggcgta   120
taa                                                                 123

<210> SEQ ID NO 14
<211> LENGTH: 303
<212> TYPE: PRT
<213> ORGANISM: Artificial Sequence
<220> FEATURE:
<223> OTHER INFORMATION: CatM protein

<400> SEQUENCE: 14

Met Glu Leu Arg His Leu Arg Tyr Phe Val Thr Val Val Glu Gln
1               5                   10                  15

Ser Ile Ser Lys Ala Ala Glu Lys Leu Cys Ile Ala Gln Pro Pro Leu
            20                  25                  30

Ser Arg Gln Ile Gln Lys Leu Glu Glu Glu Leu Gly Ile Gln Leu Phe
        35                  40                  45

Glu Arg Gly Phe Arg Pro Ala Lys Val Thr Glu Ala Gly Met Phe Phe
    50                  55                  60

Tyr Gln His Ala Val Gln Ile Leu Thr His Thr Ala Gln Ala Ser Ser
65                  70                  75                  80

Met Ala Lys Arg Ile Ala Thr Val Ser Gln Thr Leu Arg Ile Gly Tyr
                85                  90                  95

Val Ser Ser Leu Leu Tyr Gly Leu Leu Pro Glu Ile Ile Tyr Leu Phe
            100                 105                 110

Arg Gln Gln Asn Pro Glu Ile His Ile Glu Leu Ile Glu Cys Gly Thr
```

-continued

```
                115                 120                 125
Lys Asp Gln Ile Asn Ala Leu Lys Gln Gly Lys Ile Asp Leu Gly Phe
130                 135                 140

Gly Arg Leu Lys Ile Thr Asp Pro Ala Ile Arg Ile Val Leu His
145                 150                 155                 160

Lys Glu Gln Leu Lys Leu Ala Ile His Lys His His His Leu Asn Gln
                165                 170                 175

Phe Ala Ala Thr Gly Val His Leu Ser Gln Ile Ile Asp Glu Pro Met
                180                 185                 190

Leu Leu Tyr Pro Val Ser Gln Lys Pro Asn Phe Ala Thr Phe Ile Gln
                195                 200                 205

Ser Leu Phe Thr Glu Leu Gly Leu Val Pro Ser Lys Leu Thr Glu Ile
                210                 215                 220

Arg Glu Ile Gln Leu Ala Leu Gly Leu Val Ala Ala Gly Glu Gly Val
225                 230                 235                 240

Cys Ile Val Pro Ala Ser Ala Met Asp Ile Gly Val Lys Asn Leu Leu
                245                 250                 255

Tyr Ile Pro Ile Leu Asp Asp Asp Ala Tyr Ser Pro Ile Ser Leu Ala
                260                 265                 270

Val Arg Asn Met Asp His Ser Asn Tyr Ile Pro Lys Ile Leu Ala Cys
                275                 280                 285

Val Gln Glu Val Phe Ala Thr His His Ile Arg Pro Leu Ile Glu
                290                 295                 300
```

<210> SEQ ID NO 15
<211> LENGTH: 239
<212> TYPE: PRT
<213> ORGANISM: Artificial Sequence
<220> FEATURE:
<223> OTHER INFORMATION: Superfolder GFP

<400> SEQUENCE: 15

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Phe Ile
                35                  40                  45

Cys Thr Thr Gly Lys Leu Pro Val Pro Trp Pro Thr Leu Val Thr Thr
                50                  55                  60

Leu Thr Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
```

```
                180                 185                 190
Pro Val Leu Leu Pro Asp Asn His Tyr Leu Ser Thr Gln Ser Val Leu
            195                 200                 205

Ser Lys Asp Pro Asn Glu Lys Arg Asp His Met Val Leu Leu Glu Phe
            210                 215                 220

Val Thr Ala Ala Gly Ile Thr His Gly Met Asp Glu Leu Tyr Lys
225                 230                 235
```

<210> SEQ ID NO 16
<211> LENGTH: 270
<212> TYPE: PRT
<213> ORGANISM: Artificial Sequence
<220> FEATURE:
<223> OTHER INFORMATION: PobR-DM protein

<400> SEQUENCE: 16

```
Met Glu Gln His His Gln Tyr Leu Ala His Pro His Ser Ser Glu Glu
1               5                   10                  15

Ile Arg Thr Glu Asp Tyr Ile Ala Gly Leu Ala Lys Gly Leu Ala Leu
            20                  25                  30

Leu Glu Ala Phe Gly Ile Asp Arg Gln Arg Leu Asn Val Thr Gln Val
        35                  40                  45

Ala Glu Arg Thr Gly Ile Ser Arg Thr Ala Ala Arg Arg Tyr Leu Lys
    50                  55                  60

Thr Leu Lys Phe Leu Gly Tyr Leu Asp Thr Asp Glu His Tyr Phe Trp
65                  70                  75                  80

Leu Thr His Arg Val Leu Arg Phe Ser Ser Ser Tyr Leu Ser Ser Ala
                85                  90                  95

His Leu Pro Lys Val Ala Gln Ser Phe Leu Asn Leu Leu Cys Ala Gln
            100                 105                 110

Thr Ser Leu Thr Phe Ser Ile Val Val Leu Asp Glu His Glu Val Val
        115                 120                 125

Pro Val Ala Arg Ser Tyr Leu Pro Gln Gln Asp Asn Arg Val Ser Pro
    130                 135                 140

Tyr Gly Met His Leu Gly Asn Arg Leu Pro Ala His Ala Thr Ser Thr
145                 150                 155                 160

Gly Lys Val Leu Leu Ser Val Leu Asp Arg Glu Val Gln Ile Glu Trp
                165                 170                 175

Ile Glu Lys Tyr Gly Leu Lys Arg Leu Thr Pro Tyr Thr Ile Thr Asp
            180                 185                 190

Glu His Thr Phe Leu Glu Thr Leu Asp Ala Val Arg Gln Ser Asp Tyr
        195                 200                 205

Cys Leu Ser Thr Glu Glu His Glu Leu Gly Val Ile Ala Ile Ala Val
    210                 215                 220

Pro Val Leu Asn Ala Gln Gly Leu Thr Ile Ala Ala Leu Asn Cys Met
225                 230                 235                 240

Ser Gln Thr Asn Arg Val Gln Pro Gln Tyr Leu Ile Asp Gln Val Leu
                245                 250                 255

Pro Leu Leu Arg Asn Thr Ala Asn Glu Leu Arg Asn Leu Val
            260                 265                 270
```

<210> SEQ ID NO 17
<211> LENGTH: 495
<212> TYPE: DNA
<213> ORGANISM: Artificial Sequence
<220> FEATURE:
<223> OTHER INFORMATION: UbiC wild type

<400> SEQUENCE: 17

```
tcacacccccg cgttaacgca actgcgtgcg ctgcgctatt ttaaagagat ccctgccctg    60
gatccgcaac tgctcgactg gctgttgctg gaggattcca tgacaaaacg ttttgaacag   120
cagggaaaaa cggtaagcgt gacgatgatc cgcgaagggt tgtcgagca gaatgaaatc    180
cccgaagaac tgccgctgct gccgaaagag tctcgttact ggttacgtga aatttttgtta   240
tgtgccgatg gtgaaccgtg gcttgccggt cgtaccgtcg ttcctgtgtc aacgttaagc   300
gggccggagc tggcgttaca aaaattgggt aaaacgccgt taggacgcta tctgttcaca   360
tcatcgacat aacccggga ctttattgag ataggccgtg atgccgggct gtggggggcga   420
cgttcccgcc tgcgattaag cggtaaaccg ctgttgctaa cagaactgtt tttaccggcg   480
tcaccgttgt actaa                                                    495
```

<210> SEQ ID NO 18
<211> LENGTH: 163
<212> TYPE: PRT
<213> ORGANISM: Artificial Sequence
<220> FEATURE:
<223> OTHER INFORMATION: UbiC wild type

<400> SEQUENCE: 18

```
Ser His Pro Ala Leu Thr Gln Leu Arg Ala Leu Arg Tyr Phe Lys Glu
1               5                   10                  15

Ile Pro Ala Leu Asp Pro Gln Leu Leu Asp Trp Leu Leu Leu Glu Asp
                20                  25                  30

Ser Met Thr Lys Arg Phe Glu Gln Gln Gly Lys Thr Val Ser Val Thr
            35                  40                  45

Met Ile Arg Glu Gly Phe Val Glu Gln Asn Ile Pro Glu Glu Leu
        50                  55                  60

Pro Leu Leu Pro Lys Glu Ser Arg Tyr Trp Leu Arg Glu Ile Leu Leu
65                  70                  75                  80

Cys Ala Asp Gly Glu Pro Trp Leu Ala Gly Arg Thr Val Val Pro Val
                85                  90                  95

Ser Thr Leu Ser Gly Pro Glu Leu Ala Leu Gln Lys Leu Gly Lys Thr
            100                 105                 110

Pro Leu Gly Arg Tyr Leu Phe Thr Ser Ser Thr Leu Thr Arg Asp Phe
        115                 120                 125

Ile Glu Ile Gly Arg Asp Ala Gly Leu Trp Gly Arg Ser Arg Leu
    130                 135                 140

Arg Leu Ser Gly Lys Pro Leu Leu Leu Thr Glu Leu Phe Leu Pro Ala
145                 150                 155                 160

Ser Pro Leu
```

<210> SEQ ID NO 19
<211> LENGTH: 291
<212> TYPE: PRT
<213> ORGANISM: Artificial Sequence
<220> FEATURE:
<223> OTHER INFORMATION: PcaR protein

<400> SEQUENCE: 19

```
Met Ser Asp Glu Thr Leu Gly Asn Asp Ser Gly Asn Ala Glu Val Ala
1               5                   10                  15

Arg Pro Ala Ser Ala Ala Met Ala Pro Pro Ile Val Ala Ser Pro Ala
                20                  25                  30
```

Lys Arg Ile Gln Ala Phe Thr Gly Asp Pro Asp Phe Met Thr Ser Leu
 35                  40                  45

Ala Arg Gly Leu Ala Val Ile Gln Ala Phe Gln Glu Arg Lys Arg His
 50                  55                  60

Leu Thr Ile Ala Gln Ile Ser His Arg Thr Glu Ile Pro Arg Ala Ala
 65                  70                  75                  80

Val Arg Arg Cys Leu His Thr Leu Ile Lys Leu Gly Tyr Ala Thr Thr
                 85                  90                  95

Asp Gly Arg Thr Tyr Ser Leu Leu Pro Lys Val Leu Thr Leu Gly His
            100                 105                 110

Ala Tyr Leu Ser Ser Thr Pro Leu Ala Ile Ser Ala Gln Pro Tyr Leu
        115                 120                 125

Asp Arg Ile Ser Asp Gln Leu His Glu Ala Ala Asn Met Ala Thr Leu
130                 135                 140

Glu Gly Asp Asp Ile Leu Tyr Ile Ala Arg Ser Ala Thr Val Glu Arg
145                 150                 155                 160

Leu Ile Ser Val Asp Leu Ser Val Gly Gly Arg Leu Pro Ala Tyr Cys
                165                 170                 175

Thr Ser Met Gly Arg Ile Leu Leu Ala Ala Met Asp Asp Thr Ser Leu
            180                 185                 190

Arg Glu Tyr Leu Glu Arg Ala Asp Leu Lys Ala Arg Thr Ser Arg Thr
        195                 200                 205

Leu Asn Asp Pro Glu Ser Leu Phe Ala Cys Ile Gln Gln Val Arg Ala
210                 215                 220

Gln Gly Trp Cys Val Val Asp Gln Glu Leu Glu Gln Gly Leu Arg Ser
225                 230                 235                 240

Ile Ala Val Pro Val Tyr Asp Ala Ser Gly Gln Val Leu Ala Ala Leu
                245                 250                 255

Asn Val Ser Thr His Val Gly Arg Val Thr Arg Ser Glu Leu Glu Gln
            260                 265                 270

Arg Phe Leu Pro Ile Leu Leu Ala Ala Ser Arg Asp Leu Cys His Gln
        275                 280                 285

Leu Phe Gly
    290

<210> SEQ ID NO 20
<211> LENGTH: 112
<212> TYPE: DNA
<213> ORGANISM: Artificial Sequence
<220> FEATURE:
<223> OTHER INFORMATION: TphR promoter

<400> SEQUENCE: 20
agcgatcaaa tcaaggtgtt ttcaacattt ttgcgcatag cgcaaaaaca ggtttaacac    60
aaagtacgac atcctcatac tgcagttccc cacacaagaa ggagatatac at           112

<210> SEQ ID NO 21
<211> LENGTH: 3477
<212> TYPE: DNA
<213> ORGANISM: Artificial Sequence
<220> FEATURE:
<223> OTHER INFORMATION: pBTL2_PcaRpromo_sfGFP

<400> SEQUENCE: 21
tacgtaagag gttccaactt tcaccataat gaaataagat cactaccggg cgtatttttt    60
gagttatcga gattttcagg agctaaggaa gctaaaatga gccatattca acgggaaacg   120

| | |
|---|---|
| tcttgctcga ggccgcgatt aaattccaac atgatgctg atttatatgg gtataaatgg | 180 |
| gctcgcgata atgtcgggca atcaggtgcg acaatctatc gattgtatgg gaagcccgat | 240 |
| gcgccagagt tgtttctgaa acatggcaaa ggtagcgttg ccaatgatgt tacagatgag | 300 |
| atggtcaggc taaactggct gacggaattt atgcctcttc cgaccatcaa gcattttatc | 360 |
| cgtactcctg atgatgcatg gttactcacc actgcgatcc cagggaaaac agcattccag | 420 |
| gtattagaag aatatcctga ttcaggtgaa aatattgttg atgcgctggc agtgttcctg | 480 |
| cgccggttgc attcgattcc tgtttgtaat tgtcctttta acggcgatcg cgtatttcgt | 540 |
| ctcgctcagg cgcaatcacg aatgaataac ggtttggttg gtgcgagtga ttttgatgac | 600 |
| gagcgtaatg gctggcctgt tgaacaagtc tggaaagaaa tgcataagct tttgccattc | 660 |
| tcaccggatt cagtcgtcac tcatggtgat ttctcacttg ataaccttat ttttgacgag | 720 |
| gggaaattaa taggttgtat tgatgttgga cgagtcggaa tcgcagaccg ataccaggat | 780 |
| cttgccatcc tatggaactg cctcggtgag ttttctcctt cattacagaa acggcttttt | 840 |
| caaaaatatg gtattgataa tcctgatatg aataaattgc agtttcactt gatgctcgat | 900 |
| gagttttcct gagggcggat cccccctcaag tcaaaagcct ccggtcggag cttttgact | 960 |
| ttctgctatg gaggtcaggt atgattagca ttcaactgaa atgaggcaaa tagcctccag | 1020 |
| aactgctcgc agatcgcaca acagttcgat aatcgcacaa attcagccaa accctctcta | 1080 |
| ctgttgccct atcttgcggc acgctatagc gaaagtcagc aagccatttc aagtgctgac | 1140 |
| aggcccatc gcttcacgcg ctccggccag cccgacaacc acaactccag gaacaacaag | 1200 |
| gagatataca tatggctagc aaaggagaag aacttttcac gggagttgtc ccaattcttg | 1260 |
| ttgaattaga tggtgatgtt aatgggcaca aattttctgt ccgtggagag ggtgaaggtg | 1320 |
| atgctacaaa cggaaaactc acccttaaat ttatttgcac tactggaaaa ctacctgttc | 1380 |
| catggccaac acttgtcact actctgacct atggtgttca atgcttttcc cgttatccgg | 1440 |
| atcacatgaa acgcatgac ttttcaaga gtgccatgcc cgaaggttat gtacaggaac | 1500 |
| gcactatatc tttcaaagat gacgggacct acaagacgcg tgctgaagtc aagtttgaag | 1560 |
| gtgataccct tgttaatcgt atcgagttaa agggtattga ttttaaagaa gatggaaaca | 1620 |
| ttcttggaca caaactcgag tacaacttta actcacacaa tgtatacatc acggcagaca | 1680 |
| aacaaaagaa tggaatcaaa gctaacttca aaattcgcca caacgttgaa gatggttccg | 1740 |
| ttcaactagc agaccattat caacaaaata ctccaattgg cgatggccct gtccttttac | 1800 |
| cagacaacca ttacctgtcg acacaatctg tcctttcgaa agatcccaac gaaaagcgtg | 1860 |
| accacatggt ccttcttgag tttgtaactg ctgctgggat tacacatggc atggatgagc | 1920 |
| tctacaaagg tggcggttct gaattcacac ctaggtaaga tatcattcag gacgagcctc | 1980 |
| agactccagc gtaactggac tgaaaacaaa ctaaagcgcc cttgtggcgc tttagttttg | 2040 |
| ttccgcggcc accggctggc tcgcttcgct cggcccgtgg acaaccctgc tggacaagct | 2100 |
| gatgacagg ctgcgcctgc ccacgagctt gaccacaggg attgcccacc ggctacccag | 2160 |
| ccttcgacca catacccacc ggctccaact gcgcggcctg cggccttgcc ccatcaattt | 2220 |
| ttttaatttt ctctggggaa aagcctccgg cctgcgcct gcgcgcttcg cttgccggtt | 2280 |
| ggacaccaag tggaaggcgg gtcaaggctc gcgcagcgac cgcgcagcgg cttggccttg | 2340 |
| acgcgcctgg aacgacccaa gcctatgcga gtgggggcag tcgaaggcga agcccgcccg | 2400 |
| cctgcccccc gagcctcacg gcggcgagtg cgggggttcc aagggggcag cgccaccttg | 2460 |
| ggcaaggccg aaggccgcgc agtcgatcaa caagcccgg aggggccact ttttgccgga | 2520 |

```
gggggagccg cgccgaaggc gtggggaac  cccgcagggg tgcccttctt tgggcaccaa   2580
agaactagat ataggcgaa  atgcgaaaga cttaaaaatc aacaacttaa aaaggggggg   2640
tacgcaacag ctcattgcgg caccccccgc aatagctcat tgcgtaggtt aaagaaaatc   2700
tgtaattgac tgccactttt acgcaacgca taattgttgt cgcgctgccg aaaagttgca   2760
gctgattgcg catggtgccg caaccgtgcg gcaccctacc gcatggagat aagcatggcc   2820
acgcagtcca gagaaatcgg cattcaagcc aagaacaagc ccggtcactg ggtgcaaacg   2880
gaacgcaaag cgcatgaggc gtgggccggg cttattgcga ggaaacccac ggcggcaatg   2940
ctgctgcatc acctcgtggc gcagatgggc caccagaacg ccgtggtggt cagccagaag   3000
acactttcca agctcatcgg acgttctttg cggacggtcc aatacgcagt caaggacttg   3060
gtggccgagc gctggatctc cgtcgtgaag ctcaacggcc ccggcaccgt gtcggcctac   3120
gtggtcaatg accgcgtggc gtggggccag ccccgcgacc agttgcgcct gtcggtgttc   3180
agtgccgccg tggtggttga tcacgacgac caggacgaat cgctgttggg gcatggcgac   3240
ctgcgccgca tcccgaccct gtatccgggc gagcagcaac taccgaccgg ccccggcgag   3300
gagccgccca gccagcccgg cattccgggc atggaaccag acctgccagc cttgaccgaa   3360
acggaggaat gggaacggcg cgggcagcag cgcctgccga tgcccgatga gccgtgtttt   3420
ctggacgatg gcgagccgtt ggagccgccg acacgggtca gctgccgcg  ccggtag      3477

<210> SEQ ID NO 22
<211> LENGTH: 4423
<212> TYPE: DNA
<213> ORGANISM: Artificial Sequence
<220> FEATURE:
<223> OTHER INFORMATION: pBTL2_PcaR_sfGFP

<400> SEQUENCE: 22
tacgtaagag gttccaactt tcaccataat gaaataagat cactaccggg cgtatttttt     60
gagttatcga gattttcagg agctaaggaa gctaaaatga gccatattca acgggaaacg    120
tcttgctcga ggccgcgatt aaattccaac atggatgctg atttatatgg gtataaatgg    180
gctcgcgata atgtcgggca atcaggtgcg acaatctatc gattgtatgg gaagcccgat    240
gcgccagagt tgtttctgaa acatggcaaa ggtagcgttg ccaatgatgt tacagatgag    300
atggtcaggc taaactggct gacggaattt atgcctcttc cgaccatcaa gcattttatc    360
cgtactcctg atgatgcatg gttactcacc actgcgatcc cagggaaaac agcattccag    420
gtattagaag aatatcctga ttcaggtgaa aatattgttg atgcgctggc agtgttcctg    480
cgccggttgc attcgattcc tgtttgtaat tgtcctttta acggcgatcg cgtatttcgt    540
ctcgctcagg cgcaatcacg aatgaataac ggtttggttg gtgcgagtga ttttgatgac    600
gagcgtaatg gctggcctgt tgaacaagtc tggaaagaaa tgcataagct tttgccattc    660
tcaccggatt cagtcgtcac tcatggtgat ttctcacttg ataaccttat ttttgacgag    720
gggaaattaa taggttgtat tgatgttgga cgagtcggaa tcgcagaccg ataccaggat    780
cttgccatcc tatggaactg cctcggtgag ttttctcctt cattacagaa acggcttttt    840
caaaaatatg gtattgataa tcctgatatg aataaattgc agtttcactt gatgctcgat    900
gagtttttct gagggcggat cccctcaag  tcaaaagcct ccggtcggag gcttttgact    960
ttctgctatg gaggtcaggt atgatttcaa ccaaacaact ggtggcaaag gtcccggctg   1020
gctgccagca aaatcggcaa gaaccgctgc tccagttcac tgcgggtcac ccgcccgaca   1080
```

```
tgggtactga cgttcagcgc agccaacacc tgccccgaag cgtcatacac cggcacggca    1140
atcgatcgca gcccctgttc cagttcctgg tctaccacac accagccctg tgcgcgcacc    1200
tgctggatgc aggcgaacaa cgattcgggg tcattcaggg tgcggctggt gcgcgctttg    1260
aggtcggcac gttccaggta ctcacgcagg ctggtgtcat ccatggccgc cagcagaatg    1320
cgccccatcg acgtgcaata ggccggcagg cgcccgccca ccgacagatc gaccgagatc    1380
agccgctcga ccgtggccga acgggctata taaaggatgt cgtcgccctc gagggtggcc    1440
atgttggccg cctcatgcag ctggtcgctg atgcgatcca ggtacggctg tgcagaaatt    1500
gccagcggcg tcgacgacag gtaggcatgc cccaaggtca gcactttggg cagcagcgaa    1560
taggtacgcc cgtcggtggt ggcgtaaccc agtttgatca acgtgtgcag gcaacggcgc    1620
accgccgcgc gagggatttc ggtacggtga ctgatctggg cgatggtcag gtggcgcttg    1680
cgctcctgga atgcctggat cacggccagg ccacgtgcca gtgaggtcat gaagtccggg    1740
tcaccggtaa aggcctggat gcgcttggcc ggggaagcca cgatcggcgg cgccatggca    1800
gccgaagcag gtcgcgccac ctcagcattg ccggaatcgt tgcccagggt ttcgtcactc    1860
atcgcacacc tcaaaaaaaa caccggttcg tgcgattatc gaacaaacgg ccgataatcg    1920
caattgaccc ccagcattca actgaaatga ggcaaatagc ctccagaact gctcgcagat    1980
cgcacaacag ttcgataatc gcacaaattc agccaaaccc tctctactgt tgccctatct    2040
tgcggcacgc tatagcgaaa gtcagcaagc catttcaagt gctgacaggc cccatcgctt    2100
cacgcgctcc ggccagcccg acaaccacaa ctccaggaac aacaaggaga tatacatatg    2160
gctagcaaag gagaagaact tttcacggga gttgtcccaa ttcttgttga attagatggt    2220
gatgttaatg ggcacaaatt ttctgtccgt ggagagggtg aaggtgatgc tacaaacgga    2280
aaactcaccc ttaaatttat ttgcactact ggaaaactac ctgttccatg gccaacactt    2340
gtcactactc tgacctatgg tgttcaatgc ttttcccgtt atccggatca catgaaacgg    2400
catgactttt tcaagagtgc catgcccgaa ggttatgtac aggaacgcac tatatctttc    2460
aaagatgacg ggacctacaa gacgcgtgct gaagtcaagt ttgaaggtga taccctttgtt   2520 aatcgtatcg agttaaaggg tattgatttt aaagaagatg gaaacattct tggacacaaa    2580
ctcgagtaca actttaactc acacaatgta tacatcacgg cagacaaaca aaagaatgga    2640
atcaaagcta acttcaaaat tcgccacaac gttgaagatg gttccgttca actagcagac    2700
cattatcaac aaaatactcc aattggcgat ggccctgtcc ttttaccaga caaccattac    2760
ctgtcgacac aatctgtcct ttcgaaagat cccaacgaaa agcgtgacca catggtcctt    2820
cttgagtttg taactgctgc tgggattaca catggcatgg atgagctcta caaaggtggc    2880
ggttctgaat tcacacctag gtaagatatc attcaggacg agcctcagac tccagcgtaa    2940
ctggactgaa aacaaactaa agcgcccttg tggcgcttta gttttgttcc gcggccaccg    3000
gctggctcgc ttcgctcggc ccgtggacaa ccctgctgga caagctgatg gacaggctgc    3060
gcctgcccac gagcttgacc acagggattg cccaccggct acccagcctt cgaccacata    3120
cccaccggct ccaactgcgc ggcctgcggc cttgccccat caattttttt aatttttctct    3180 ggggaaaagc ctccggcctg cggcctgcgc gcttcgcttg ccggttggac accaagtgga    3240
aggcgggtca aggctcgcgc agcgaccgcg cagcggcttg ccttgacgc gcctggaacg    3300 acccaagcct atgcgagtgg gggcagtcga aggcgaagcc cgcccgcctg cccccgagc    3360 ctcacgcgcg cgagtgcggg ggttccaagg gggcagcgcc accttgggca aggccgaagg    3420
ccgcgcagtc gatcaacaag ccccggaggg gccactttt gccggagggg gagccgcgcc    3480
```

```
gaaggcgtgg gggaaccccg caggggtgcc cttctttggg caccaaagaa ctagatatag    3540
ggcgaaatgc gaaagactta aaaatcaaca acttaaaaaa gggggggtacg caacagctca    3600 ttgcggcacc ccccgcaata gctcattgcg taggttaaag aaaatctgta attgactgcc    3660
acttttacgc aacgcataat tgttgtcgcg ctgccgaaaa gttgcagctg attgcgcatg    3720
gtgccgcaac cgtgcggcac cctaccgcat ggagataagc atggccacgc agtccagaga    3780
aatcggcatt caagccaaga acaagcccgg tcactgggtg caaacggaac gcaaagcgca    3840
tgaggcgtgg gccgggctta ttgcgaggaa acccacggcg gcaatgctgc tgcatcacct    3900
cgtggcgcag atgggccacc agaacgccgt ggtggtcagc cagaagacac tttccaagct    3960
catcggacgt tctttgcgga cggtccaata cgcagtcaag gacttggtgg ccgagcgctg    4020
gatctccgtc gtgaagctca acggcccggg caccgtgtcg gcctacgtgg tcaatgaccg    4080
cgtggcgtgg ggccagcccc gcgaccagtt cgcctgtcg gtgttcagtg ccgccgtggt    4140
ggttgatcac gacgaccagg acgaatcgct gttggggcat ggcgacctgc gccgcatccc    4200
gaccctgtat ccgggcgagc agcaactacc gaccggcccc ggcgaggagc cgcccagcca    4260
gcccggcatt ccgggcatgg aaccagacct gccagccttg accgaaacgg aggaatggga    4320
acggcgcggg cagcagcgcc tgccgatgcc cgatgagccg tgttttctgg acgatggcga    4380
gccgttggag ccgccgacac gggtcacgct gccgcgccgg tag                      4423

<210> SEQ ID NO 23
<211> LENGTH: 123
<212> TYPE: DNA
<213> ORGANISM: Artificial Sequence
<220> FEATURE:
<223> OTHER INFORMATION: CatM_A9 promoter

<400> SEQUENCE: 23
ttatacgccc taattggttt tatataccttt tttagtatgc aaaaatacca aattggtgtg     60 gattttatt attacattaa tttacagtat gtaaatagta tttattgaaa agaagatgga    120
ccg                                                                 123

<210> SEQ ID NO 24
<211> LENGTH: 909
<212> TYPE: DNA
<213> ORGANISM: Artificial Sequence
<220> FEATURE:
<223> OTHER INFORMATION: CatM_C2.9

<400> SEQUENCE: 24
ttcgatgagt ggcctgatat ggtgcgttgc aaacacctcc tgtacacagg cgagaatttt     60
aggaatgtaa ttactgtggt ccatatttcg caccgcgagt gaaattgggc tataggcatc    120
atcatctaaa attggaatat aaagtagatt cttcacccca atatccatgg cagacgccgg    180
tacgatgcag acgccttcac ctgctgccac caagccgagt gccagttgaa tttctcgaat    240
ttcggtgagt ttggatggta ctaggcctag ttcggtaaag agtgactgaa taaaggtcgc    300
aaaattgggc ttttgagaga ctgggtacag cagcatcggt tcatcaataa tttgagagag    360
atgaacccct gttgctgcaa actgattgag gtgatgatgc ttatggattg caagtttgag    420
ctgttcttta tgcaacacga tacgtcgaat tgcaggatcg gtaattttga cccgaccaaa    480
acccagatct attttttccct gcttaagggc attaatttga tctttggcgg cgcattcgat    540
gagttcgatg tgaatttcag gattttgttg acgaaacaga taaataattt caggtaacaa    600
```

```
accatacagt aaggagctga tgtaaccaat tctcaaggtt tgactgaccg ttgcaatccg    660
ttttgccatt gaggacgctt gtgcagtatg agtcaaaatc tgcacagcat gctgataaaa    720
aaacatgcct gcttcagtca ctttagccgg tctgaagccg cgttcaaata gttggatacc    780
caattcttct tcgagttttt gaatttgtcg gctgaggggc ggctgggcaa tacacaactt    840
ttcagcagct ttggaaatgc tttgctcttc aaccacggtc acaaaatatc tgaggtgtct    900
tagttccat                                                            909
```

<210> SEQ ID NO 25
<211> LENGTH: 303
<212> TYPE: PRT
<213> ORGANISM: Artificial Sequence
<220> FEATURE:
<223> OTHER INFORMATION: CatM_C2.9

<400> SEQUENCE: 25

```
Met Glu Leu Arg His Leu Arg Tyr Phe Val Thr Val Glu Glu Gln
1               5                   10                  15

Ser Ile Ser Lys Ala Ala Glu Lys Leu Cys Ile Ala Gln Pro Leu
            20                  25                  30

Ser Arg Gln Ile Gln Lys Leu Glu Glu Glu Leu Gly Ile Gln Leu Phe
        35                  40                  45

Glu Arg Gly Phe Arg Pro Ala Lys Val Thr Glu Ala Gly Met Phe Phe
50                  55                  60

Tyr Gln His Ala Val Gln Ile Leu Thr His Thr Ala Gln Ala Ser Ser
65              70                  75                  80

Met Ala Lys Arg Ile Ala Thr Val Ser Gln Thr Leu Arg Ile Gly Tyr
                85                  90                  95

Ile Ser Ser Leu Leu Tyr Gly Leu Leu Pro Glu Ile Ile Tyr Leu Phe
            100                 105                 110

Arg Gln Gln Asn Pro Glu Ile His Ile Glu Leu Ile Glu Cys Ala Ala
        115                 120                 125

Lys Asp Gln Ile Asn Ala Leu Lys Gln Gly Lys Ile Asp Leu Gly Phe
    130                 135                 140

Gly Arg Val Lys Ile Thr Asp Pro Ala Ile Arg Arg Ile Val Leu His
145                 150                 155                 160

Lys Glu Gln Leu Lys Leu Ala Ile His Lys His His Leu Asn Gln
                165                 170                 175

Phe Ala Ala Thr Gly Val His Leu Ser Gln Ile Ile Asp Glu Pro Met
            180                 185                 190

Leu Leu Tyr Pro Val Ser Gln Lys Pro Asn Phe Ala Thr Phe Ile Gln
        195                 200                 205

Ser Leu Phe Thr Glu Leu Gly Leu Val Pro Ser Lys Leu Thr Glu Ile
    210                 215                 220

Arg Glu Ile Gln Leu Ala Leu Gly Leu Val Ala Ala Gly Glu Gly Val
225                 230                 235                 240

Cys Ile Val Pro Ala Ser Ala Met Asp Ile Gly Val Lys Asn Leu Leu
                245                 250                 255

Tyr Ile Pro Ile Leu Asp Asp Asp Ala Tyr Ser Pro Ile Ser Leu Ala
            260                 265                 270

Val Arg Asn Met Asp His Ser Asn Tyr Ile Pro Lys Ile Leu Ala Cys
        275                 280                 285

Val Gln Glu Val Phe Ala Thr His His Ile Arg Pro Leu Ile Glu
    290                 295                 300
```

```
<210> SEQ ID NO 26
<211> LENGTH: 291
<212> TYPE: PRT
<213> ORGANISM: Artificial Sequence
<220> FEATURE:
<223> OTHER INFORMATION: PcaR-G5

<400> SEQUENCE: 26

Met Ser Asp Glu Thr Leu Gly Asn Asp Ser Gly Asn Ala Glu Val Ala
1               5                   10                  15

Arg Pro Ala Ser Ala Ala Met Ala Pro Pro Ile Val Ala Ser Pro Ala
            20                  25                  30

Lys Arg Ile Gln Ala Phe Thr Gly Asp Pro Asp Phe Met Thr Ser Leu
        35                  40                  45

Ala Arg Gly Leu Ala Val Ile Gln Ala Phe Gln Glu Arg Lys Arg His
    50                  55                  60

Leu Thr Ile Ala Gln Ile Ser His Arg Thr Glu Ile Pro Arg Ala Ala
65                  70                  75                  80

Val Arg Arg Cys Leu His Thr Leu Ile Lys Leu Gly Tyr Ala Thr Thr
                85                  90                  95

Asp Gly Arg Thr Tyr Ser Leu Leu Pro Lys Val Leu Thr Leu Gly His
            100                 105                 110

Ala Tyr Leu Ser Ser Thr Pro Leu Ala Ile Ser Ala Gln Pro Tyr Leu
        115                 120                 125

Asp Arg Ile Ser Asp Gln Leu His Glu Ala Ala Asn Met Ala Thr Leu
    130                 135                 140

Glu Gly Asp Asp Ile Leu Tyr Ile Ala Arg Ser Ala Thr Val Glu Arg
145                 150                 155                 160

Leu Ile Ser Val Asp Leu Ser Val Gly Gly Arg Met Pro Ala Tyr Cys
                165                 170                 175

Thr Ser Met Gly Arg Ile Leu Leu Ala Ala Met Asp Asp Thr Ser Leu
            180                 185                 190

Arg Glu Tyr Leu Glu Arg Ala Asp Leu Lys Ala Arg Thr Ser Arg Thr
        195                 200                 205

Leu Asn Asp Pro Glu Ser Leu Phe Ala Cys Ile Gln Gln Val Arg Ala
    210                 215                 220

Gln Gly Trp Cys Val Val Asp Gln Glu Leu Glu Gln Gly Val Arg Ala
225                 230                 235                 240

Ile Ala Val Pro Val Tyr Asp Ala Ser Gly Gln Val Leu Ala Ala Leu
                245                 250                 255

Ser Val Ser Thr His Val Gly Arg Val Thr Arg Ser Glu Leu Glu Gln
            260                 265                 270

Arg Phe Leu Pro Ile Leu Leu Ala Ala Ser Arg Asp Leu Cys His Gln
        275                 280                 285

Leu Phe Gly
    290

<210> SEQ ID NO 27
<211> LENGTH: 291
<212> TYPE: PRT
<213> ORGANISM: Artificial Sequence
<220> FEATURE:
<223> OTHER INFORMATION: PcaR-F6

<400> SEQUENCE: 27

Met Ser Asp Glu Thr Leu Gly Asn Asp Ser Gly Asn Ala Glu Val Ala
1               5                   10                  15
```

```
Arg Pro Ala Ser Ala Ala Met Ala Pro Pro Ile Val Ala Ser Pro Ala
            20                  25                  30

Lys Arg Ile Gln Ala Phe Thr Gly Asp Pro Asp Phe Met Thr Ser Leu
        35                  40                  45

Ala Arg Gly Leu Ala Val Ile Gln Ala Phe Gln Glu Arg Lys Arg His
 50                  55                  60

Leu Thr Ile Ala Gln Ile Ser His Arg Thr Glu Ile Pro Arg Ala Ala
 65                  70                  75                  80

Val Arg Arg Cys Leu His Thr Leu Ile Lys Leu Gly Tyr Ala Thr Thr
                85                  90                  95

Asp Gly Arg Thr Tyr Ser Leu Leu Pro Lys Val Leu Thr Leu Gly His
            100                 105                 110

Ala Tyr Leu Ser Ser Thr Pro Leu Ala Ile Ser Ala Gln Pro Tyr Leu
        115                 120                 125

Asp Arg Ile Ser Asp Gln Leu His Glu Ala Ala Asn Met Ala Thr Leu
130                 135                 140

Glu Gly Asp Asp Ile Leu Tyr Ile Ala Arg Ser Ala Thr Val Glu Arg
145                 150                 155                 160

Leu Ile Ser Val Asp Leu Ser Val Gly Gly Arg Leu Pro Ala Tyr Cys
                165                 170                 175

Thr Ser Met Gly Arg Ile Leu Leu Ala Ala Met Asp Asp Thr Ser Leu
            180                 185                 190

Arg Glu Tyr Leu Glu Arg Ala Asp Leu Lys Ala Arg Thr Ser Arg Thr
        195                 200                 205

Leu Asn Asp Pro Glu Ser Leu Phe Ala Cys Ile Gln Gln Val Arg Ala
210                 215                 220

Gln Gly Trp Cys Val Val Asp Gln Glu Leu Glu Gln Gly Met Arg Thr
225                 230                 235                 240

Ile Ala Val Pro Val Tyr Asp Ala Ser Gly Gln Val Leu Ala Ala Leu
                245                 250                 255

Ser Val Ser Thr His Val Gly Arg Val Thr Arg Ser Glu Leu Glu Gln
            260                 265                 270

Arg Phe Leu Pro Ile Leu Leu Ala Ala Ser Arg Asp Leu Cys His Gln
        275                 280                 285

Leu Phe Gly
        290

<210> SEQ ID NO 28
<211> LENGTH: 291
<212> TYPE: PRT
<213> ORGANISM: Artificial Sequence
<220> FEATURE:
<223> OTHER INFORMATION: PcaR-H6

<400> SEQUENCE: 28

Met Ser Asp Glu Thr Leu Gly Asn Asp Ser Gly Asn Ala Glu Val Ala
 1               5                  10                  15

Arg Pro Ala Ser Ala Ala Met Ala Pro Pro Ile Val Ala Ser Pro Ala
            20                  25                  30

Lys Arg Ile Gln Ala Phe Thr Gly Asp Pro Asp Phe Met Thr Ser Leu
        35                  40                  45

Ala Arg Gly Leu Ala Val Ile Gln Ala Phe Gln Glu Arg Lys Arg His
 50                  55                  60

Leu Thr Ile Ala Gln Ile Ser His Arg Thr Glu Ile Pro Arg Ala Ala
 65                  70                  75                  80
```

Val Arg Arg Cys Leu His Thr Leu Ile Lys Leu Gly Tyr Ala Thr Thr
                85                  90                  95

Asp Gly Arg Thr Tyr Ser Leu Leu Pro Lys Val Leu Thr Leu Gly His
            100                 105                 110

Ala Tyr Leu Ser Ser Thr Pro Leu Ala Ile Ser Ala Gln Pro Tyr Leu
        115                 120                 125

Asp Arg Ile Ser Asp Gln Leu His Glu Ala Ala Asn Met Ala Thr Leu
    130                 135                 140

Glu Gly Asp Asp Ile Leu Tyr Ile Ala Arg Ser Ala Thr Val Glu Arg
145                 150                 155                 160

Leu Ile Ser Val Asp Leu Ser Val Gly Gly Arg Met Pro Ala Tyr Cys
                165                 170                 175

Thr Ser Met Gly Arg Ile Leu Leu Ala Ala Met Asp Asp Thr Ser Leu
            180                 185                 190

Arg Glu Tyr Leu Glu Arg Ala Asp Leu Lys Ala Arg Thr Ser Arg Thr
        195                 200                 205

Leu Asn Asp Pro Glu Ser Leu Phe Ala Cys Ile Gln Gln Val Arg Ala
    210                 215                 220

Gln Gly Trp Cys Val Val Asp Gln Glu Leu Gln Gly Val Arg Ser
225                 230                 235                 240

Ile Ala Val Pro Val Tyr Asp Ala Ser Gly Gln Val Leu Ala Ala Leu
                245                 250                 255

Ser Val Ser Thr His Val Gly Arg Val Thr Arg Ser Glu Leu Glu Gln
            260                 265                 270

Arg Phe Leu Pro Ile Leu Leu Ala Ala Ser Arg Asp Leu Cys His Gln
        275                 280                 285

Leu Phe Gly
    290

<210> SEQ ID NO 29
<211> LENGTH: 4693
<212> TYPE: DNA
<213> ORGANISM: Artificial Sequence
<220> FEATURE:
<223> OTHER INFORMATION: pPobR_ubiC-wt

<400> SEQUENCE: 29
tacgtaagag gttccaactt tcaccataat gaaataagat cactaccggg cgtatttttt      60
gagttatcga gattttcagg agctaaggaa gctaaaatga gccatattca acgggaaacg     120
tcttgctcga ggccgcgatt aaattccaac atggatgctg atttatatgg gtataaatgg     180
gctcgcgata atgtcgggca atcaggtgcg acaatctatc gattgtatgg gaagcccgat     240
gcgccagagt tgtttctgaa acatggcaaa ggtagcgttg ccaatgatgt tacagatgag     300
atggtcaggc taaactggct gacggaattt atgcctcttc cgaccatcaa gcattttatc     360
cgtactcctg atgatgcatg gttactcacc actgcgatcc cagggaaaac agcattccag     420
gtattagaag aatatcctga ttcaggtgaa atattgttg atgcgctggc agtgttcctg      480
cgccggttgc attcgattcc tgtttgtaat tgtccttta acggcgatcg cgtatttcgt      540
ctcgctcagg cgcaatcacg aatgaataac ggtttggttg gtgcgagtga ttttgatgac     600
gagcgtaatg gctggcctgt tgaacaagtc tggaaagaaa tgcataagct tttgccattc     660
tcaccggatt cagtcgtcac tcatggtgat ttctcacttg ataaccttat ttttgacgag     720
gggaaattaa taggttgtat tgatgttgga cgagtcggaa tcgcagaccg ataccaggat     780

```
cttgccatcc tatggaactg cctcggtgag ttttctcctt cattacagaa acggcttttt      840
caaaaatatg gtattgataa tcctgatatg aataaattgc agtttcactt gatgctcgat      900
gagtttttct gagggcggat cccccctcaag tcaaaagcct ccggtcggag cttttttgact     960 ttctgctatg gaggtcaggt atgatttttat accagattgc gcagttcgtt ggcagtgttg    1020
cgcagcaacg gtaacacctg gtcgatgagg tactggggtt gaacccgatt agtctgggac    1080
atgcagttca gggctgcaat cgtcagccct tgtgcgttga ggactggaac cgcaatggca    1140
atcacaccga gctcatgttc ttccgtggat aagcagtaat ccgactgacg aacggcatcc    1200
agggtttcaa gaaaggtgtg ttcatcggtg atggtatacg gcgtcaggcg tttcaggcca    1260
tacttctcga tccactcgat ctgtacttcg cgatcaagca cgctaagaag cactttaccg    1320
gttgaggtag catgcgcagg cagacgattc cctaagtgca tgccatacgg actgacgcgg    1380
ttgtcttgct gaggcagata ggaacgggcg actggaacca cctcgtgttc atccaggacc    1440
acaatgctaa acgtcagact cgtctgcgca cacagcagat tgaggaaaga ttgggccact    1500
ttcggcaaat gcgctgaact cagatagctc gaagagaagc gcaaaacacg atgggttaac    1560
cagaagtagt gttcgtcagt atccaggtaa cccagaaact tcagggtttt cagatagcga    1620
cgagctgctg tacggctaat gccggtgcgt tcagctacct gtgtcacgtt taagcgctgc    1680
cgatcaatgc caaacgcttc cagtaacgcc agaccttttg ccagtcccgc gatgtagtcc    1740
tctgtacgaa tctcttcgct cgaatgcgga tgcgccaaat actgatggtg ttgttccata    1800
acattcaaat ccaaaatggt tttgtccgat catcggacag ttgtaatgct aatcggataa    1860
ttttgagcct tgattataga gtctttttta atgaggcggt actttaaaaa tagaaaatag    1920
caaggagata tacatatggc tagcaaagga gaagaacttt tcacgggagt tgtcccaatt    1980
cttgttgaat tagatggtga tgttaatggg cacaaatttt ctgtccgtgg agagggtgaa    2040
ggtgatgcta caaacggaaa actcacccctt aaattttatt tgcactactgg aaaactacct    2100 gttccatggc caacacttgt cactactctg acctatggtg ttcaatgctt ttcccgttat    2160
ccggatcaca tgaaacggca tgactttttc aagagtgcca tgcccgaagg ttatgtacag    2220
gaacgcacta tatcttttcaa agatgacggg acctacaaga cgcgtgctga agtcaagttt    2280
gaaggtgata cccttgttaa tcgtatcgag ttaaagggta ttgattttaa agaagatgga    2340
aacattcttg gacacaaact cgagtacaac tttaactcac acaatgtata catcacggca    2400
gacaaacaaa agaatggaat caaagctaac ttcaaaattc gccacaacgt tgaagatggt    2460
tccgttcaac tagcagacca ttatcaacaa aatactccaa ttggcgatgg ccctgtcctt    2520
ttaccagaca accattacct gtcgacacaa tctgtccttt cgaaagatcc caacgaaaag    2580
cgtgaccaca tggtccttct tgagtttgta actgctgctg ggattacaca tggcatggat    2640
gagctctaca aaggtggcgg ttctgaattc tcacaccccg cgttaacgca actgcgtgcg    2700
ctgcgctatt ttaaagagat ccctgccctg gatccgcaac tgctcgactg gctgttgctg    2760
gaggattcca tgacaaaacg ttttgaacag cagggaaaaa cggtaagcgt gacgatgatc    2820
cgcgaagggt ttgtcgagca gaatgaaatc cccgaagaac tgccgctgct gccgaaagag    2880
tctcgttact ggtacgtgaa aattttgtta tgtgccgatg tgaaccgtg gcttgccggt    2940 cgtaccgtcg ttcctgtgtc aacgttaagc gggccggagc tggcgttaca aaaattgggt    3000
aaaacgccgt aggacgcta tctgttcaca tcatcgacat taacccggga ctttattgag    3060
ataggccgtg atgccgggct gtggggcga cgttcccgcc tgcgattaag cggtaaaccg    3120
ctgttgctaa cagaactgtt tttaccggcg tcaccgttgt actaacctag gtaagatatc    3180
```

| | |
|---|---|
| attcaggacg agcctcagac tccagcgtaa ctggactgaa acaaactaa agcgcccttg | 3240 |
| tggcgcttta gttttgttcc gcggccaccg gctggctcgc ttcgctcggc ccgtggacaa | 3300 |
| ccctgctgga caagctgatg gacaggctgc gcctgcccac gagcttgacc acagggattg | 3360 |
| cccaccggct acccagcctt cgaccacata cccaccggct ccaactgcgc ggcctgcggc | 3420 |
| cttgccccat caattttttt aattttctct ggggaaaagc ctccggcctg cggcctgcgc | 3480 |
| gcttcgcttg ccggttggac accaagtgga aggcgggtca aggctcgcgc agcgaccgcg | 3540 |
| cagcggcttg gccttgacgc gcctggaacg acccaagcct atgcgagtgg gggcagtcga | 3600 |
| aggcgaagcc cgcccgcctg cccccgagc ctcacggcgg cgagtgcggg ggttccaagg | 3660 |
| gggcagcgcc accttgggca aggccgaagg ccgcgcagtc gatcaacaag ccccggaggg | 3720 |
| gccactttt gccggagggg gagccgcgcc gaaggcgtgg gggaaccccg caggggtgcc | 3780 |
| cttctttggg caccaaagaa ctagatatag ggcgaaatgc gaaagactta aaaatcaaca | 3840 |
| acttaaaaaa gggggtacg caacagctca ttgcggcacc ccccgcaata gctcattgcg | 3900 |
| taggttaaag aaaatctgta attgactgcc acttttacgc aacgcataat tgttgtcgcg | 3960 |
| ctgccgaaaa gttgcagctg attgcgcatg gtgccgcaac cgtgcggcac cctaccgcat | 4020 |
| ggagataagc atggccacgc agtccagaga aatcggcatt caagccaaga caagcccgg | 4080 |
| tcactgggtg caaacggaac gcaaagcgca tgaggcgtgg gccgggctta ttgcgaggaa | 4140 |
| acccacggcg gcaatgctgc tgcatcacct cgtggcgcag atgggccacc agaacgccgt | 4200 |
| ggtggtcagc cagaagacac tttccaagct catcggacgt tctttgcgga cggtccaata | 4260 |
| cgcagtcaag gacttggtgg ccgagcgctg gatctccgtc gtgaagctca acggccccgg | 4320 |
| caccgtgtcg gcctacgtgg tcaatgaccg cgtggcgtgg gccagcccc gcgaccagtt | 4380 |
| gcgcctgtcg gtgttcagtg ccgccgtggt ggttgatcac gacgaccagg acgaatcgct | 4440 |
| gttggggcat ggcgacctgc gccgcatccc gaccctgtat ccgggcgagc agcaactacc | 4500 |
| gaccggcccc ggcgaggagc cgcccagcca gcccggcatt ccgggcatgg aaccagacct | 4560 |
| gccagccttg accgaaacgg aggaatggga acggcgcggg cagcagcgcc tgccgatgcc | 4620 |
| cgatgagccg tgttttctgg acgatggcga gccgttggag ccgccgacac gggtcacgct | 4680 |
| gccgcgccgg tag | 4693 |

<210> SEQ ID NO 30
<211> LENGTH: 5558
<212> TYPE: DNA
<213> ORGANISM: Artificial Sequence
<220> FEATURE:
<223> OTHER INFORMATION: pPcaU1.2_pobA-wt

<400> SEQUENCE: 30

| | |
|---|---|
| tacgtaagag gttccaactt tcaccataat gaaataagat cactaccggg cgtatttttt | 60 |
| gagttatcga gattttcagg agctaaggaa gctaaaatga gccatattca acgggaaacg | 120 |
| tcttgctcga ggccgcgatt aaattccaac atggatgctg atttatatgg gtataaatgg | 180 |
| gctcgcgata atgtcgggca atcaggtgcg acaatctatc gattgtatgg gaagcccgat | 240 |
| gcgccagagt tgtttctgaa acatggcaaa ggtagcgttg ccaatgatgt tacagatgag | 300 |
| atggtcaggc taaactggct gacggaattt atgcctcttc cgaccatcaa gcattttatc | 360 |
| cgtactcctg atgatgcatg gttactcacc actgcgatcc cagggaaaac agcattccag | 420 |
| gtattagaag aatatcctga ttcaggtgaa aatattgttg atgcgctggc agtgttcctg | 480 |

```
cgccggttgc attcgattcc tgtttgtaat tgtccttta acggcgatcg cgtatttcgt    540
ctcgctcagg cgcaatcacg aatgaataac ggtttggttg gtgcgagtga ttttgatgac   600
gagcgtaatg gctggcctgt tgaacaagtc tggaaagaaa tgcataagct tttgccattc   660
tcaccggatt cagtcgtcac tcatggtgat ttctcacttg ataaccttat ttttgacgag   720
gggaaattaa taggttgtat tgatgttgga cgagtcggaa tcgcagaccg ataccaggat   780
cttgccatcc tatggaactg cctcggtgag ttttctcctt cattacagaa acggttttt    840
caaaaatatg gtattgataa tcctgatatg aataaattgc agtttcactt gatgctcgat   900
gagttttct gagggcggat cccctcaag tcaaaagcct ccggtcggag cttttgact      960
ttctgctatg gaggtcaggt atgatttac aggatattgc gcaattcacg cgcagtttcc   1020
tgcagtaacg gcagaatatg ctgaatcagg tattctttcg tggtccgcat tgtcgggctg   1080
acaatgttca gtgccgctac gacgcgagac tgctgtccat aaatcggaac cgcaagggcg   1140
tgcactccca gttcgtgttc ttccgaacta tagcaccaac cctgttcctt gatttcactc   1200
aaaaggcgca gaaagtcgat gttgttggta tacgtgtatt tcgtgagccg ttgcagaggg   1260
tactgattga gccactcttg ctgggcatgg tcatccaaat acgctaacag gattttgccc   1320
gctgacgttg catgcgctgg taagcgattc ccgagatgta agccatacgg gttaacgcga   1380
taaccttgct gatgagcggc agaacgcgca atggtaatgg cttcatagcc atccaacacc   1440
atcacgctgt aaatcaggct ggtctgggtc gtaagcaagt tcagcagtgg ttgggaaatt   1500
ttcggcagtt gagcaccacc cagatatgag ccactgaatt tcaggatttt gggagttaag   1560
tagaagtagt gaccgtcgct ttccagatag cccagatact ccagagtaag cagatggcga   1620
cgagctgctg cacgtgtcat accggttttc tctgcggcca tggtgatatt gaggcgatga   1680
cgatctgtgc caaacgaatc cagaatcgcc atccctttgc taatgccggc tacaaaatct   1740
tcgtggcgga tgatcttctt gttggtggaa ttgtgcagaa ttttctcctc tttcactttc   1800
ttgtcatcca tgttcgacca cattccagct actacatacg attgtcatat tgacatgtat   1860
aatataacgc ggaatgacta taactaaatc atgttttgtt cgattatcga acaaattatt   1920
taaatatcga caaaacctc taaactacta tggtactgaa tcaaaaaatt atacacaatg   1980
atcagacaag ggaattctac tgaatgacaa aggaaatagt atttcatcca tataaattca   2040
cttccttaaa catgcttaat tttccttcct atcaaatttg ctagatgcac aaggagatat   2100
acatatggct agcaaaggag aagaactttt cacgggagtt gtcccaattc ttgttgaatt   2160
agatggtgat gttaatgggc acaaattttc tgtccgtgga gagggtgaag gtgatgctac   2220
aaacggaaaa ctcacccctta aatttatttg cactactgga aaactacctg ttccatggcc   2280
aacacttgtc actactctga cctatggtgt tcaatgcttt tcccgttatc cggatcacat   2340
gaaacggcat gactttttca agagtgccat gcccgaaggt tatgtacagg aacgcactat   2400
atctttcaaa gatgacggga cctacaagac gcgtgctgaa gtcaagtttg aaggtgatac   2460
ccttgttaat cgtatcgagt taaagggtat tgattttaaa gaagatggaa acattcttgg   2520
acacaaactc gagtacaact ttaactcaca caatgtatac atcacggcag acaaacaaaa   2580
gaatggaatc aaagctaact tcaaaattcg ccacaacgtt gaagatggtt ccgttcaact   2640
agcagaccat tatcaacaaa atactccaat tggcgatggc cctgtccttt taccagacaa   2700
ccattacctg tcgacacaat ctgtcctttc gaaagatccc aacgaaaagc gtgaccacat   2760
ggtccttctt gagtttgtaa ctgctgctgg gattacacat ggcatggatg agctctacaa   2820
aggtggcggt tctgaattca tgaaaactca ggttgcaatt attggtgcag gtccgtctgg   2880
```

```
cctgctgctg ggccagctgc tgcacaaggc cggtatcgat aacatcatcg tcgaacgcca    2940
gactgccgag tacgtactag gccgcatccg cgccggggtg ctagagcaag gcacggtcga    3000
cctgctgcgc gaggctggcg tggccgagcg catggaccgt gaaggcctgg tgcacgaggg    3060
ggttgaactg ctggttggcg ggcgccgcca gcgtctggat ctcaaagccc tgaccggcga    3120
caagacggtg atggtctacg ccagaccga agtcacccgt gacctgatgc aggcccgcga    3180
agccagtggt gcgccgatca tttattcagc cgccaacgtt cagccgcatg aattgaaagg    3240
cgagaagccc tacctgacgt tcgaaaagga tggccgggtg cagcggattg actgcgacta    3300
tatcgccggc tgcgacggct ccacggtat ctcgcggcag agcatcccgg agggcgtgct    3360
gaaacagtat gagcgggttt acccgttggg ctggctgggc ctgctgtcgg acacaccgcc    3420
agtcaatcac gagttgatct acgcccacca tgagcgcggt ttcgcgttgt gtagccaacg    3480
ctcgcaaaca cgcagccgct actacctgca ggtacctttg caggatcggg tcgaggagtg    3540
gtctgacgag cgtttctggg acgaactgaa agcccgtctg cccgccgagg tggcggcgga    3600
cctggtcaca ggccccgcgt tggaaaaaag tattgcgccg ctgcgtagcc tggtggtcga    3660
acccatgcag tatggtcacc tgttcctggt ggggacgcg cgcacatcg tcccccctac    3720 gggtgccaaa ggccttaacc tggcggcctc cgacgtcaac tacctgtacc gcattctggt    3780
caaggtgtac cacgaagggc gcgtcgacct gcttgcgcaa tactcgccgc tggcactgcg    3840
ccgcgtgtgg aagggcgagc gcttcagctg gttcatgacc caactgctgc atgacttcgg    3900
tagccacaag gacgcctggg accagaagat gcaggaagct gaccgcgagt acttcctgac    3960
ctcgccggcg ggcctggtga acattgccga gaactatgtg gggctgccgt cgaggaagt    4020 tgcctgaaca cctaggtaag atatcattca ggacagcct cagactccag cgtaactgga    4080
ctgaaaacaa actaaagcgc ccttgtggcg ctttagtttt gttccgcggc caccggctgg    4140
ctcgcttcgc tcggcccgtg acaaccctg ctggacaagc tgatggacag gctgcgcctg    4200
cccacgagct tgaccacagg gattgcccac cggctaccca gccttcgacc acatacccac    4260
cggctccaac tgcgcggcct gcggccttgc cccatcaatt tttttaattt tctctgggga    4320
aaagcctccg gcctgcggcc tgcgcgcttc gcttgccggt tggacaccaa gtggaaggcg    4380
ggtcaaggct cgcgcagcga ccgcgcagcg gcttggcctt gacgcgcctg gaacgaccca    4440
agcctatgcg agtgggggca gtcgaaggcg aagcccgccc gctgccccc cgagcctcac    4500 ggcggcgagt gcgggggttc caaggggca gcgccacctt gggcaaggcc gaaggccgcg    4560
cagtcgatca acaagccccg gagggcac tttttgccgg aggggggagcc gcgccgaagg    4620 cgtgggggaa ccccgcaggg gtgccttct ttgggcacca agaactaga tatagggcga    4680 aatgcgaaag acttaaaaat caacaactta aaaagggg gtacgcaaca gctcattgcg    4740
gcaccccccg caatagctca ttgcgtaggt taaagaaaat ctgtaattga ctgccacttt    4800
tacgcaacgc ataattgttg tcgcgctgcc gaaaagttgc agctgattgc gcatggtgcc    4860
gcaaccgtgc ggcaccctac cgcatggaga taagcatggc cacgcagtcc agagaaatcg    4920
gcattcaagc caagaacaag cccggtcact gggtgcaaac ggaacgcaaa gcgcatgagg    4980
cgtgggccgg gcttattgcg aggaaaccca cggcggcaat gctgctgcat cacctcgtgg    5040
cgcagatggg ccaccagaac gccgtggtgg tcagccagaa gacactttcc aagctcatcg    5100
gacgttcttt gcggacggtc caatacgcag tcaaggactt ggtggccgag cgctggatct    5160
ccgtcgtgaa gctcaacggc cccggcaccg tgtcggccta cgtggtcaat gaccgcgtgg    5220
```

```
cgtggggcca gccccgcgac cagttgcgcc tgtcggtgtt cagtgccgcc gtggtggttg   5280
atcacgacga ccaggacgaa tcgctgttgg ggcatggcga cctgcgccgc atcccgaccc   5340
tgtatccggg cgagcagcaa ctaccgaccg gccccggcga ggagccgccc agccagcccg   5400
gcattccggg catggaacca gacctgccag ccttgaccga aacggaggaa tgggaacggc   5460
gcgggcagca gcgcctgccg atgcccgatg agccgtgttt tctggacgat ggcgagccgt   5520
tggagccgcc gacacgggtc acgctgccgc gccggtag                           5558
```

```
<210> SEQ ID NO 31
<211> LENGTH: 6182
<212> TYPE: DNA
<213> ORGANISM: Artificial Sequence
<220> FEATURE:
<223> OTHER INFORMATION: pGLO_pNPmut1.1_sfGFP_PON1-G3C9

<400> SEQUENCE: 31
```

```
atcgatgcat aatgtgcctg tcaaatggac gaagcaggga ttctgcaacc ctatgctact     60
ccgtcaagcc gtcaattgtc tgattcgtta ccaattatac cagattgcgc agttcgttgg    120
cagtgttgcg cagcaacggt aacacctggt cgatgaggta ctggggttga acccgattag    180
tctgggacag gcagttcagg gctgcaatcg tcagcccttg tgcgttgagg actggaaccg    240
caatgccaat cacaccgagc tcatattctt ccgtggttaa gcagtaatcc gactgacgaa    300
cggcatccag ggtttcaaga aggtgtgtt catcggtgat ggtatacggc gtcaggcgtt    360
tcaggccata cttctcgatc cactcgatct gtacttcgcg atcaagcacg ctaagaagca    420
ctttaccggt tgcgatagca tgcgcaggca gacgattccc taagtgcatg ccatacggac    480
tgaggcggtt gttttgctga ggcagatagg aacgggcgac tggaaccacc tcgtgttcat    540
ccaggaccac aatggtaaac gtcagactcg tctgcgcaca cagcagattg aggaaagatt    600
gggccacttt cggcaaatgc gctgaactca gatagctcga agagaagcgc aaaacacgat    660
gggttaacca aagtagtgt tcgtcagtat ccaggtaacc cagaaacttc agggttttca    720
gatagcgacg agctgctgta cggctaatgc cggtgcgttc agctacctgt gtcacgttta    780
agcgctgccg atcaatgcca aacgcttcca gtaacgccag accttttgcc agtcccgcga    840
tgtagtcctc tgtacgaatc tcttcgctcg aatgcggatg cgccaaatac tgatggtgtt    900
gttccataac attcaaatcc aaaatggttt tgtccgatca tcggacagtt gtaatgctaa    960
gcggataatt ttgagccttg attatagatg tcttttttaat gaggcggtac tttaaaaata   1020
gaaaatagca aggagatata catatggcta gcaaaggaga gaacttttc acgggagttg   1080 tcccaattct tgttgaatta gatggtgatg ttaatgggca caaattttct gtccgtggag   1140
agggtgaagg tgatgctaca aacgaaaac tcacccttaa atttatttgc actactggaa   1200
aactacctgt tccatggcca acacttgtca ctactctgac ctatggtgtt caatgctttt   1260
cccgttatcc ggatcacatg aaacggcatg acttttttcaa gagtgccatg cccgaaggtt   1320
atgtacagga acgcactata tcttttcaaag atgacggac ctacaagacg cgtgctgaag   1380
tcaagtttga aggtgatacc cttgttaatc gtatcgagtt aaagggtatt gattttaaag   1440
aagatggaaa cattcttgga cacaaactcg agtacaactt taactcacac aatgtataca   1500
tcacggcaga caaacaaaag aatggaatca agctaactt caaaattcgc cacaacgttg   1560
aagatggttc cgttcaacta gcagaccatt atcaacaaaa tactccaatt ggcgatggcc   1620
ctgtcctttt accagacaac cattacctgt cgacacaatc tgtcctttcg aaagatccca   1680
acgaaaagcg tgaccacatg gtccttcttg agtttgtaac tgctgctggg attacacatg   1740
```

```
gcatggatga gctctacaaa ggtggcggtt ctgaattcgc taaactgaca gcgctcacac    1800
tcttggggct gggattggca ctcttcgatg gacagaagtc ttctttccaa acacgattta    1860
atgttcaccg tgaagtaact ccagtggaac ttcctaactg taatttagtt aaaggggttg    1920
acaatggttc tgaagacttg gaaatactgc ccaatggact ggctttcatc agctccggat    1980
taaagtatcc tggaataatg agctttgacc ctgataagtc tggaaagata cttctaatgg    2040
acctgaatga ggaagaccca gtagtgttgg aactgggcat tactgaaaat acattggata    2100
tatcttcatt taaccctcat gggattagca cattcacaga tgaagataac actgtgtacc    2160
tactggtggt aaaccatcca gactcctcgt ccaccgtgga ggtgtttaaa tttcaagaag    2220
aagaaaaatc acttttgcat ctgaaaacca tcagacacaa gcttctgcct agtgtgaatg    2280
acattgtcgc tgtgggacct gaacacttt atgccacaaa tgatcactat tttgctgacc    2340
cttacttaaa atcctgggaa atgcatttgg gattagcgtg gtcatttgtt acttattata    2400
gtcccaatga tgttcgagta gtggcagaag gatttgattt tgctaacgga atcaacatct    2460
caccagacgg caagtatgtc tatatagctg agttgctggc tcataagatc catgtgtatg    2520
aaaagcacgc taattggact ttaactccat tgaagtccct cgactttgac acccttgtgg    2580
ataacatctc tgtggatcct gtgacagggg acctctgggt gggatgccat cccaacggaa    2640
tgcgaatctt ctactatgac ccaaagaatc ctcccggctc agaggtgctt cgaatccagg    2700
acattttatc cgaagagccc aaagtgacag tggtttatgc agaaaatggc actgtgttac    2760
agggcagcac ggtggccgct gtgtacaaag ggaaactgct gattggcaca gtgtttcaca    2820 aagctctta ctgtgagctg gcggccgcac tcgagcacca ccaccaccac cactaaccta    2880
ggtaaggtac ccgggatcc tctagagtcg acctgcaggc atgcaagctt ggctgttttg    2940
gcggatgaga gaagattttc agcctgatac agattaaatc agaacgcaga gcggtctga    3000 taaaacagaa tttgcctggc ggcagtagcg cggtggtccc acctgacccc atgccgaact    3060
cagaagtgaa acgccgtagc gccgatggta gtgtggggtc ccccatgcga gagtagggaa    3120
ctgccaggca tcaaataaaa cgaaaggctc agtcaaaga ctgggccttt cgttttatct    3180
gttgtttgtc ggtgaacgct ctcctgagta ggacaaatcc gccgggagcg atttgaacg    3240 ttgcgaagca acggcccgga gggtggcggg caggacgccc gccataaact gccaggcatc    3300
aaattaagca gaaggccatc ctgacggatg gcctttttgc gtttctacaa actctttgtt    3360
tattttctca aatacattca aatatgtatc cgctcatgag acaataaccc tgataaatgc    3420
ttcaataata ttgaaaaagg aagagtatga gtattcaaca tttccgtgtc gcccttattc    3480 cctttttgc ggcattttgc cttcctgttt ttgctcaccc agaaacgctg gtgaaagtaa    3540
aagatgctga agatcagttg ggtgcacgag tgggttacat cgaactggat ctcaacagcg    3600
gtaagatcct tgagagtttt cgccccgaag aacgttttcc aatgatgagc acttttaaag    3660
ttctgctatg tggcgcggta ttatcccgtg ttgacgccgg gcaagagcaa ctcggtcgcc    3720
gcatacacta ttctcagaat gacttggttg agtactcacc agtcacagaa aagcatctta    3780
cggatggcat gacagtaaga gaattatgca gtgctgccat aaccatgagt gataacactg    3840
cggccaactt acttctgaca acgatcgag gaccgaagga gctaaccgct ttttgcaca    3900 acatggggga tcatgtaact cgccttgatc gttgggaacc ggagctgaat gaagccatac    3960
caaacgacga gcgtgacacc acgatgcctg cagcaatggc aacaacgttg cgcaaactat    4020
taactggcga actacttact ctagcttccc ggcaacaatt aatagactgg atggaggcgg    4080
```

```
ataaagttgc aggaccactt ctgcgctcgg cccttccggc tggctggttt attgctgata    4140
aatctggagc cggtgagcgt gggtctcgcg gtatcattgc agcactgggg ccagatggta    4200
agccctcccg tatcgtagtt atctacacga cggggagtca ggcaactatg gatgaacgaa    4260
atagacagat cgctgagata ggtgcctcac tgattaagca ttggtaactg tcagaccaag    4320
tttactcata tactttag attgatttac gcgccctgta gcggcgcatt aagcgcggcg      4380
ggtgtggtgg ttacgcgcag cgtgaccgct acacttgcca gcgccctagc gcccgctcct   4440
ttcgctttct tcccttcctt tctcgccacg ttcgccggct ttccccgtca gctctaaat    4500
cgggggctcc ctttagggtt ccgatttagt gctttacggc acctcgaccc caaaaaactt   4560
gatttgggtg atggttcacg tagtgggcca tcgccctgat agacggtttt cgcccttig    4620
acgttggagt ccacgttctt taatagtgga ctcttgttcc aaactggaac aacactcaac   4680
cctatctcgg gctattcttt tgatttataa gggattttgc cgatttcggc ctattggtta   4740
aaaaatgagc tgatttaaca aaaatttaac gcgaatttta acaaaatatt aacgtttaca   4800
atttaaaagg atctaggtga agatccttttt tgataatctc atgaccaaaa tcccttaacg  4860
tgagttttcg ttccactgag cgtcagaccc cgtagaaaag atcaaaggat cttcttgaga   4920
tccttttttt ctgcgcgtaa tctgctgctt gcaaacaaaa aaaccaccgc taccagcggt   4980
ggtttgtttg ccggatcaag agctaccaac tcttttccg aaggtaactg gcttcagcag    5040
agcgcagata ccaaatactg tccttctagt gtagccgtag ttaggccacc acttcaagaa   5100
ctctgtagca ccgcctacat acctcgctct gctaatcctg ttaccagtgg ctgctgccag   5160
tggcgataag tcgtgtctta ccgggttgga ctcaagacga tagttaccgg ataaggcgca   5220
gcggtcgggc tgaacggggg gttcgtgcac acagcccagc ttggagcgaa cgacctacac   5280
cgaactgaga tacctacagc gtgagcattg agaaagcgcc acgcttcccg aagggagaaa   5340
ggcggacagg tatccggtaa gcggcagggt cggaacagga gagcgcacga gggagcttcc   5400
agggggaaac gcctggtatc tttatagtcc tgtcgggttt cgccacctct gacttgagcg   5460
tcgatttttg tgatgctcgt caggggggcg gagcctatgg aaaaacgcca gcaacgcggc   5520
cttttacgg ttcctggcct tttgctggcc tttgctcac atgttctttc ctgcgttatc     5580
ccctgattct gtggataacc gtattaccgc ctttgagtga gctgataccg ctcgccgcag   5640
ccgaacgacc gagcgcagcg agtcagtgag cgaggaagcg gaagagcgcc tgatgcggta   5700
ttttctcctt acgcatctgt gcggtatttc acaccgcata tggtgcactc tcagtacaat   5760
ctgctctgat gccgcatagt taagccagta tacactccgc tatcgctacg tgactgggtc   5820
atggctgcgc cccgacaccc gccaacaccc gctgacgcgc cctgacgggc ttgtctgctc   5880
ccggcatccg cttacagaca agctgtgacc gtctccggga gctgcatgtg tcagaggttt   5940
tcaccgtcat caccgaaacg cgcgaggcag caaggagatg gcgcccaaca gtccccggc    6000
cacgggcct gccaccatac ccacgccgaa acaagcgctc atgagcccga agtggcgagc    6060
ccgatcttcc ccatcggtga tgtcggcgat ataggcgcca gcaaccgcac ctgtggcgcc   6120
ggtgatgccg gccacgatgc gtccggcgta gaggatctaa ttctcatgtt tgacagctta   6180
tc                                                                   6182
```

<210> SEQ ID NO 32
<211> LENGTH: 355
<212> TYPE: PRT
<213> ORGANISM: Artificial Sequence
<220> FEATURE:
<223> OTHER INFORMATION: PON1-G3C9 amino acid sequence

<400> SEQUENCE: 32

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Pro Lys Val Thr Val Val
305                 310                 315                 320

Tyr Ala Glu Asn Gly Thr Val Leu Gln Gly Ser Thr Val Ala Ala Val
                325                 330                 335

Tyr Lys Gly Lys Leu Leu Ile Gly Thr Val Phe His Lys Ala Leu Tyr
            340                 345                 350

Cys Glu Leu
        355
```

<210> SEQ ID NO 33
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 33
tgctatggag gtcaggtatg attttatacc agattgcgca gttcg                45

<210> SEQ ID NO 34
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 34
gttcttctcc tttgctagcc atatgtatat ctccttgcta ttttc                45

<210> SEQ ID NO 35
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 35
atggctagca aaggagaaga ac                                         22

<210> SEQ ID NO 36
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 36
gaggctcgtc ctgaatgata tcttacctag gtgtgaattc agaac                45

<210> SEQ ID NO 37
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 37
gatatcattc aggacgagcc tcagactcc                                  29

<210> SEQ ID NO 38
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 38
aatcatacct gacctccata gcagaaagtc aaaag                           35

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 39
agtcgaattc tcacaccccg cgttaacgca ac                              32

<210> SEQ ID NO 40

```
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 40
agtccctagg ttagtacaac ggtgacgccg g                              31

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 41
acaaaacgtt ttgaacagca g                                        21

<210> SEQ ID NO 42
<211> LENGTH: 54
<212> TYPE: DNA
<213> ORGANISM: Artificial Sequence
<220> FEATURE:
<223> OTHER INFORMATION: Olignonucleotide primer

<400> SEQUENCE: 42
ctgctgttca aaacgttttg tcayggaatc ctscagcaac agccagtcga gcag    54

<210> SEQ ID NO 43
<211> LENGTH: 54
<212> TYPE: DNA
<213> ORGANISM: Artificial Sequence
<220> FEATURE:
<223> OTHER INFORMATION: Oligonucleotide primer

<400> SEQUENCE: 43
ctgctgttca aaacgttttg tcatggaatc ctccgccaac agccagtcga gcag    54

<210> SEQ ID NO 44
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 44
gccacggttc accatcggca catamcaaaa yttcchttaa ccagtaacga gactctttcg   60

<210> SEQ ID NO 45
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 45
ccgatggtga accgtggctt gccrgtcgtr ccgtcgttcc tgtgtcaacg tta       53

<210> SEQ ID NO 46
<211> LENGTH: 44
<212> TYPE: DNA
<213> ORGANISM: Artificial Sequence
<220> FEATURE:
<223> OTHER INFORMATION: Oligonucleotide primer

<400> SEQUENCE: 46
```

```
gatgtgaaca gatagcgtcc tamcggcgtt ttacccaatt tttg        44
```

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 47

```
ggacgctatc tgttcacatc                                  20
```

<210> SEQ ID NO 48
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 48

```
agtccctagg ttagtgatgg tgatggtgat ggccaccgta caacggtgac gccgg    55
```

<210> SEQ ID NO 49
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 49

```
ggcatcatcg cgacgacatc gtcgaaa                          27
```

<210> SEQ ID NO 50
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 50

```
tatcgagctg gccggcatgg aggcg                            25
```

<210> SEQ ID NO 51
<211> LENGTH: 11
<212> TYPE: PRT
<213> ORGANISM: Artificial Sequence
<220> FEATURE:
<223> OTHER INFORMATION: Mutational library 1 K70

<400> SEQUENCE: 51

Tyr His Asn Asp Gln Lys Glu Phe Leu Ile Val
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Mutational library 1 Y71

<400> SEQUENCE: 52

Arg Asn Asp Cys Gly His Ile Leu Phe Ser Tyr Val
1               5                   10

<210> SEQ ID NO 53

-continued

```
<211> LENGTH: 4
<212> TYPE: PRT
<213> ORGANISM: Artificial Sequence
<220> FEATURE:
<223> OTHER INFORMATION: Mutational library 1 P72

<400> SEQUENCE: 53

Ser Pro Thr Ala
1

<210> SEQ ID NO 54
<211> LENGTH: 4
<212> TYPE: PRT
<213> ORGANISM: Artificial Sequence
<220> FEATURE:
<223> OTHER INFORMATION: Mutational library 1 G73/Mutational library 2
      G116

<400> SEQUENCE: 54

Thr Ser Ala Gly
1

<210> SEQ ID NO 55
<211> LENGTH: 4
<212> TYPE: PRT
<213> ORGANISM: Artificial Sequence
<220> FEATURE:
<223> OTHER INFORMATION: Mutational library 2 F222

<400> SEQUENCE: 55

Ile Asn Tyr Phe
1

<210> SEQ ID NO 56
<211> LENGTH: 278
<212> TYPE: PRT
<213> ORGANISM: Acinetobacter baylyi ADP1

<400> SEQUENCE: 56

Met Trp Ser Asn Met Asp Asp Lys Lys Val Lys Glu Glu Lys Ile Leu
1               5                   10                  15

His Asn Ser Thr Asn Lys Lys Ile Ile Arg His Glu Asp Phe Val Ala
            20                  25                  30

Gly Ile Ser Lys Gly Met Ala Ile Leu Asp Ser Phe Gly Thr Asp Arg
        35                  40                  45

His Arg Leu Asn Ile Thr Met Ala Ala Glu Lys Thr Gly Met Thr Arg
    50                  55                  60

Ala Ala Ala Arg Arg His Leu Leu Thr Leu Glu Tyr Leu Gly Tyr Leu
65                  70                  75                  80

Glu Ser Asp Gly His Tyr Phe Tyr Leu Thr Pro Lys Ile Leu Lys Phe
                85                  90                  95

Ser Gly Ser Tyr Leu Gly Gly Ala Gln Leu Pro Lys Ile Ser Gln Pro
            100                 105                 110

Leu Leu Asn Leu Leu Thr Thr Gln Thr Ser Leu Ile Tyr Ser Val Met
        115                 120                 125

Val Leu Asp Gly Tyr Glu Ala Ile Thr Ile Ala Arg Ser Ala Ala His
    130                 135                 140

Gln Gln Thr Asp Arg Val Asn Pro Tyr Gly Leu His Leu Gly Asn Arg
145                 150                 155                 160

Leu Pro Ala His Ala Thr Ser Ala Gly Lys Ile Leu Leu Ala Tyr Leu
                165                 170                 175
```

-continued

```
Asp Asp His Ala Gln Gln Glu Trp Leu Asn Gln Tyr Pro Leu Gln Arg
            180                 185                 190

Leu Thr Lys Tyr Thr Tyr Thr Asn Asn Ile Asp Phe Leu Arg Leu Leu
        195                 200                 205

Ser Glu Ile Lys Glu Gln Gly Trp Cys Tyr Ser Ser Glu Glu His Glu
        210                 215                 220

Leu Gly Val His Ala Leu Ala Val Pro Ile Tyr Gly Gln Gln Ser Arg
225                 230                 235                 240

Val Val Ala Ala Leu Asn Ile Val Ser Pro Thr Met Arg Thr Thr Lys
                245                 250                 255

Glu Tyr Leu Ile Gln His Ile Leu Pro Leu Leu Gln Glu Thr Ala Arg
            260                 265                 270

Glu Leu Arg Asn Ile Leu
            275
```